US010544449B2

(12) United States Patent
Shen et al.

(10) Patent No.: US 10,544,449 B2
(45) Date of Patent: *Jan. 28, 2020

(54) BIS-BIOTINYLATION TAGS

(71) Applicant: Pacific Biosciences of California, Inc., Menlo Park, CA (US)

(72) Inventors: Gene Shen, Santa Clara, CA (US); Natasha Popovich, Belmont, CA (US); Erik Miller, San Francisco, CA (US); Satwik Kamtekar, Mountain View, CA (US); Keith Bjornson, Fremont, CA (US); Jeremiah Hanes, Woodside, CA (US); Stephen Yue, Eugene, OR (US); Lubomir Sebo, Hayward, CA (US); Zhong Wang, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 15/399,931

(22) Filed: Jan. 6, 2017

(65) Prior Publication Data

US 2017/0184580 A1    Jun. 29, 2017

Related U.S. Application Data

(63) Continuation-in-part of application No. 14/303,296, filed on Jun. 12, 2014, now Pat. No. 9,678,080.

(60) Provisional application No. 61/835,311, filed on Jun. 14, 2013, provisional application No. 62/276,444, filed on Jan. 8, 2016.

(51) Int. Cl.
| | |
|---|---|
| *C07D 495/04* | (2006.01) |
| *C07D 403/14* | (2006.01) |
| *C07D 401/14* | (2006.01) |
| *C12Q 1/6844* | (2018.01) |
| *C08G 65/334* | (2006.01) |
| *C07F 7/18* | (2006.01) |

(52) U.S. Cl.
CPC ......... *C12Q 1/6844* (2013.01); *C07D 401/14* (2013.01); *C07D 403/14* (2013.01); *C07D 495/04* (2013.01); *C07F 7/1804* (2013.01); *C08G 65/3348* (2013.01); *C07B 2200/11* (2013.01); *C08G 2650/04* (2013.01)

(58) Field of Classification Search
CPC ... C07D 495/04; C07D 401/14; C07D 403/14
USPC ................ 544/198; 548/303.7; 514/245, 387
See application file for complete search history.

(56) References Cited

U.S. PATENT DOCUMENTS

| | | | |
|---|---|---|---|
| 5,143,854 A | 9/1992 | Pirrung et al. | |
| 5,723,584 A | 3/1998 | Schatz | |
| 5,874,239 A | 2/1999 | Schatz | |
| 5,932,433 A | 8/1999 | Schatz | |
| 6,153,442 A | 11/2000 | Pirio et al. | |
| 6,265,552 B1 | 7/2001 | Schatz | |
| 7,033,775 B2 * | 4/2006 | Ullman ............ | G01N 33/54386 435/7.91 |
| 7,056,661 B2 | 6/2006 | Korlach et al. | |
| 7,141,676 B1 | 11/2006 | Wilbur et al. | |
| 7,315,019 B2 | 1/2008 | Turner et al. | |
| 7,763,423 B2 | 7/2010 | Roitman et al. | |
| 7,842,475 B2 | 11/2010 | Zheng et al. | |
| 7,981,632 B2 | 7/2011 | Schmidt | |
| 7,993,891 B2 | 8/2011 | Roitman et al. | |
| 8,133,672 B2 | 3/2012 | Bjornson et al. | |
| 8,137,942 B2 | 3/2012 | Roitman et al. | |
| 8,193,123 B2 | 6/2012 | Rank et al. | |
| 8,252,910 B2 | 8/2012 | Korlach et al. | |
| 8,389,676 B2 | 3/2013 | Christians | |
| 8,501,406 B1 | 8/2013 | Gray et al. | |
| 8,759,488 B2 | 6/2014 | Howarth | |
| 8,906,831 B2 | 12/2014 | Eid et al. | |
| 9,678,080 B2 * | 6/2017 | Miller .................... | C07K 14/36 |
| 2001/0055766 A1 | 12/2001 | Aristarhov et al. | |
| 2002/0128234 A1 | 9/2002 | Hubbell et al. | |
| 2008/0199932 A1 | 8/2008 | Henzel et al. | |
| 2009/0005264 A1 | 1/2009 | Rakestraw et al. | |
| 2009/0233291 A1 | 9/2009 | Chen et al. | |
| 2010/0035254 A1 | 2/2010 | Williams | |
| 2011/0014151 A1 | 1/2011 | Nilsson et al. | |
| 2012/0052490 A1 | 3/2012 | Eid et al. | |
| 2013/0052130 A1 | 2/2013 | Davis et al. | |
| 2013/0316912 A1 | 11/2013 | Bjornson | |
| 2015/0307933 A1 | 10/2015 | Shen et al. | |
| 2016/0310926 A1 | 10/2016 | Sun et al. | |
| 2017/0145495 A1 | 5/2017 | Sebo et al. | |
| 2017/0145496 A1 | 5/2017 | Sebo et al. | |
| 2017/0145502 A1 | 5/2017 | Shen et al. | |
| 2017/0321268 A1 | 11/2017 | Shen et al. | |

FOREIGN PATENT DOCUMENTS

| | | | |
|---|---|---|---|
| EP | 1963530 B1 | 7/2011 | |
| WO | 1991007087 A1 | 5/1991 | |
| WO | 1999060400 A1 | 11/1999 | |
| WO | 2012065043 A2 | 5/2012 | |
| WO | 2013036826 A2 | 3/2013 | |
| WO | WO-2013036826 A2 * | 3/2013 | ........... C12Q 1/6816 |
| WO | 2013123258 A1 | 8/2013 | |

OTHER PUBLICATIONS

First Exam Report dated Sep. 30, 2018 for related CN 201480033832.1.

(Continued)

*Primary Examiner* — Venkataraman Balasubramanian
(74) *Attorney, Agent, or Firm* — Pacific Biosciences of California, Inc.

(57) ABSTRACT

Multi-biotinylated reactants are provided which can be used in divalent complexes for various applications such as colocalization, labeling, immobilization, and purification. Methods for constructing, purifying, and using the bis-biotinylated reactants are also provided. In certain embodiments, two bis-biotinylated reactants are bound to a single streptavidin tetramer to provide a complex having a 1:1 stoichiometry with respect to the bis-biotinylated reactants.

8 Claims, 16 Drawing Sheets

(56) References Cited

OTHER PUBLICATIONS

Aime, et al., "High Sensitivity Lanthanide (III) Based Probes for MR-Medical Imaging," Coordination Chemistry Reviews (2006) 250:1562-1579.

Beckett, et al., "A Minimal Peptide Substrate in Biotin Holoenzyme Synthetase-Catalyzed Biotinylation," Protein Science (1999) 8:921-929.

Chivers, et al.,"A Streptavidin Variant with Slower Biotin Dissocation and Increased Mechanostability," Nat. Methods (2010) 7(5):391-393.

Eid et al., "Real-Time DNA Sequencing From Single Polymerase Molecules," Science (2009) 323:133-138.

Farah, et al., "Point Mutagenesis and Cocrystallization of Wild-Type and Mutant Proteins: A Study of Solid-Phase Coexistence in Two-Dimensional Protein Arrays," Langmuir (2001) 17:5731-5735.

Fierer, et al., "SpyLigase Peptide-Peptide Ligation Polymerizes Affibodies to Enhance Magnetic Cancer Cell Capture," Proc. Natl. Acad. USA (2014) E1176-E1181.

Furukawa, et al., "Development of Novel Yeast Cell Surface Display System for Homo-Oligomeric Protein by Coexpression of Native and Anchored Subunits," Biotechnol. Prog. (2006) 22:994-997.

Green, "Avidin," Adv. Protein Res. (1975) 29:85-133.

Holmberg, et al., "The Biotin-Streptavidin Interaction can be Reversibly Broken Using Water at Elevated Temperatures," Electrophoresis (2005) 26:501-510.

Horton, et al., "Engineering Hybrid Genes Without the Use of Restriction Enzymes: Gene Splicing by Overlap Extension," Gene (1989) 77(1):61-8.

Howarth et al., "Imaging Proteins in Live Mammalian Cells with Biotin Ligase and Monovalent Streptavidin," Nature Protocols (2008) 3(3):534-545.

Howarth, et al., "A Monovalent Streptavidin with Single Femtomolar Biotin Binding Site," Nature Methods (2006) 3(4):267-73.

Levene et al., "Zero-mode Waveguides for Single-molecule Analysis at High Concentration" Science (2003) 299:682-686.

Ringler and Schulz, "Self-Assembly of Proteins into Designed Networks," Science (2003) 302:106-109.

Sattely, et al., "Total Biosynthesis: In Vitro Reconstitution of Polyketide and Nonribosomal Peptide Pathways," Natural Product Reports (2008) 25:757-793.

Schechter, et al., "Renal Accumulation of Streptavidin: Potential Use for Targeted Therapy to the Kidney," Kidney International (1995) 47:1327-1335.

Schoene, et al., "SpyTag/SpyCatcher Cyclization Confers Resilience to Boiling on a Mesophilic Enzyme," Agnew. Chem. Int. Ed. (2014) 53: 1-5.

Shimoboji, et al., "Mechanistic Investigation of Smart Polymer-Protein Conjugates," Bioconjugate Chemistry (2001) 12:314-319.

Tahiri-Alaoui, et al., "High Affinity Nucleic Acid Aptamers for Streptavidin Incorporated into Bi-Specific Capture Ligands," Nuc. Ac. Res (2002) 30(10):e45.

Takakura, et al., "Tamavidins—Novel Avidin-Like Biotin-Binding Proteins from the Tamogitake Mushroom," FEBS Journal (2009) 276(5):1383-97.

Thompson, et al., "Engineering and Identifying Supercharged Proteins for Macromolecule Delivery into Mammalian Cells," Methods in Enzymology (2012) 503:293-318.

Wei, et al., "Bacterial Virulence Proteins as Tools to Rewire Kinase Pathways in Yeast and Immune Cells," Nature (2012) 488:384-388.

Wilbur et al., "Design and Synthesis of Bis-Biotin-Containing Reagents for Applications Utilizing Monoclonal Antibody-Based Pretargeting Systems and Streptavidin Mutants," Bioconjugate Chem. 21(7):1225-1238.

Wilbur, et al., "Biotin Reagents for Antibody Pretargeting. 2. Synthesis and in Vitro Evaluation of Biotin Dimers and Trimers for Cross-Linking of Streptavidin," Bioconjugate Chemistry (1997) 8(6):819-32.

Wilbur, et al., "Biotin Reagents for Antibody Pretargeting. 3. Synthesis, Radioiodination, and Evaluation of Biotinylated Starburst Dendrimers," Bioconjugate Chemistry (1998) 9:813-825.

Wilson, et al., "The Use of mRNA Display to Select High-Affinity Protein-Binding Peptides," Proc. Natl. Acad. Sci. USA (2001) 98:3750-3755.

Xia, et al., "Quantifying the Kinetic Stability of Hyperstable Proteins Via Time Dependent SDS Trapping," Biochemistry (2012) 51:100-107.

Zakeri, et al., "Peptide Tag Forming a Rapid Covalent Bond to a Protein, Through Engineering a Bacterial Adhesin," PNAS (2012) 109(12):E690-7.

Zareh, et al., "Single-Molecule Imaging of Protein Adsorption Mechanisms to Surfaces," Microscopy Research and Technique (2011) 74:682-687.

Zhang, et al., "Controlling Macromolecular Topology with Genetically Encoded SpyTag-SpyCatcher Chemistry," J. Am. Chem. Soc. (2013) 135: 13988-13997.

Dressman, et al., "Transforming Single DNA Molecules Into Fluorescent Magnetic Particles for Detection and Enumeration of Genetic Variations," PNAS (2003) 100(15):8817-8822.

International Search Report and Written Opinion dated Oct. 1, 2014 for related PCT/US2014/042149.

International Preliminary Report on Patentability dated Dec. 23, 2015 for related PCT/US2014/042149.

Extended Search Report dated Mar. 10, 2017 for related case EP14810199.1.

Janssen, et al., "Nucleic Acids for Ultra-Sensitive Protein Detection," Sensors (2013) 13(1):1353-1384.

Niemeyer, et al., "Hapten-Functionalized DNA-Streptavidin Nanocircles as Supramolecular Reagents in a Compatitive Immuno-PCR Assay," Angewandte Chemie International Edition (2001) 40(17):3169-3172.

Niemeyer, et al., "Self-Assembly of DNA-Streptavidin Nanostructures and Their Use as Reagents in Immuno-PCR," Nucl. Acids. Res. Informational Retrieval Ltd., (1999) 27(23):4553-4561.

Niemeyer, et al., "Supramolecular DNA-Streptavidin Nanocricles with a Covalently Attached Oligonucleotide Moiety," Journ of Biomolecular Structure & Dynamics, Adenine Press (2002) 20(2):223-230.

Garlick and Giese, "Dissociative Binding of Alpha- and Beta-Sulphoxides of Biotinylamidoethyl-3-(4-Hydroxy-3-[125I] iodophenyl)Propionamide to Avidin," Biochemical Journal (1990) 268(3):611-613.

Wormser et al., "Synthesis and Growth-Promoting Activity of dl-cis-Hexahydro-4-(4-Carboxybutyl)-2-Cyclopentimidazolone: Carbobiotin," Journal of Pharmaceutical Sciences (1972) 61(7):1168-1170.

DeTitta et al., "Carboxybiotin Translocation Mechanisms Suggested by Diffraction Studies in Biotin and Its Vitamers," Proc. Natl. Acad. Sci USA (1980) 77(1):333-7.

Stallings and DeTitta, "Crystallographic Investigations of Biotin and Carboxybiotin Derivatives," Ann N Y Acad. Sci. (1985) 447:152-68.

Hytonen et al., "Structure and Characterization of a Novel Chicken Biotin-Binding Protein A (BBP-A)" BMC Structural Biology (2007) 7:8.

Huang et al., "Biotin-Derivatized Poly(L-lysine)-g-Poly(Ethylene Glycol): A Novel Plymeric Interface for Bioaffinity Sensing," Langmuir (2002) 18(1):220-230.

Korlach et al., "Selective Aluminum Passivation for Targeted Immobilization of Single DNA Polymerase Molecules in Zero-Mode Waveguide Nanostructures," (2008) PNAS 105(4):1176-1181.

First Exam Report dated Nov. 6, 2017 for related case EP 14810199.1.

Second Exam Report dated Mar. 2, 2018 for related case EP 14810199.1.

Second Exam Report dated Feb. 27, 2019 for related CN 201480033832.1.

* cited by examiner

BIS-BIOTINYLATION TAGS

CROSS-REFERENCE TO RELATED APPLICATIONS

This application is a non-provisional utility patent application claiming priority to and benefit of provisional patent application U.S. Ser. No. 62/276,444, filed Jan. 8, 2016, entitled "BIS-BIOTINYLATION TAGS" by Gene Shen et al., and is a continuation-in-part of U.S. Ser. No. 14/303,296, filed Jun. 12, 2014, entitled "BIS-BIOTINYLATION TAGS" by Erik Miller et al., which claims priority to and benefit of provisional application U.S. Ser. No. 61/835,311, filed Jun. 14, 2013, entitled "BIS-BIOTINYLATION TAGS" by Erik Miller et al. Each of these applications is incorporated herein by reference in its entirety for all purposes.

STATEMENT REGARDING FEDERALLY SPONSORED RESEARCH

Not Applicable.

DESCRIPTION OF THE BACKGROUND ART

A common task in molecular biology is to identify and quantify the presence of a protein in a complex mixture. For example, to identify the level of expression of a protein of interest, a western blot can be performed in which a protein extract is run on a gel and stained with antibodies against a defined epitope of the protein of interest. The defined epitope can be a particular sequence or structure found in the native protein, or can be a tag introduced during cloning, e.g., a "FLAG tag" for which specific antibodies are commercially available. A secondary peroxidase-conjugated antibody specific for the primary antibody bound to the protein is used to generate a detectable signal. This process is cumbersome and more streamlined methods for purification of proteins from cell extracts are desirable.

Attaching optical labels to proteins can be an alternate strategy for detection and quantification, however, this typically requires chemical modification of residues within the protein. Attaching dyes through lysine or cysteine residues often modifies activity or reduces solubility making purification of the labeled protein difficult or impossible. Fluorescent protein tags are available with a wide variety of spectral properties, e.g., as described in Shaner, et al. (2005) Nature Methods 2(12):905-909, incorporated by reference herein in its entirety for all purposes, but these tags are suboptimal for single-molecule experimentation.

The ability to synthesize DNA chemically has made possible the construction of peptides and proteins not otherwise found in nature and useful in a wide variety of methods that would otherwise be very difficult or impossible to perform. The patent literature, for instance, is replete with publications describing the recombinant expression of receptor proteins. See, e.g., PCT Patent Pub. No. 91/18982 and U.S. Pat. Nos. 5,081,228 and 4,968,607, which describe recombinant DNA molecules encoding the IL-1 receptor; U.S. Pat. Nos. 4,816,565; 4,578,335; and 4,845,198, which describe recombinant DNA and proteins relating to the IL-2 receptor; PCT Patent Pub. No. 91/08214, which describes EGF receptor gene related nucleic acids; PCT Patent Pub. No. 91/16431 and U.S. Pat. No. 4,897,264, which describe the interferon gamma receptor and related proteins and nucleic acids; European Patent Office (EPO) Pub. No. 377,489, which describes the C5a receptor protein; PCT Patent Pub. No. 90/08822, which describes the EPO receptor and related nucleic acids; PCT Patent Pub. No. 92/01715, which describes MHC receptors; and U.S. patent application Ser. No. 947,339, filed on Sep. 18, 1992, which describes how HPAP-containing receptors can be cleaved from the cell surface and how the anchoring sequences that remain can serve as recognition sequences for antibodies that are used to immobilize the receptor. Several of these publications, each of which is incorporated herein by reference for all purposes, describe both how to isolate a particular receptor protein (or the gene encoding the protein) and variants of the receptor that may be useful in ways the natural or native receptor is not.

The advances made with respect to receptor cloning and expression have been accompanied by advances in technology relating to methods for screening a receptor against compounds that may interact with the receptor in a desired fashion. One such advance relates to the generation of large numbers of compounds, or potential ligands, in a variety of random and semi-random "peptide diversity" generation systems. These systems include the "peptides on plasmids" system described in U.S. Pat. No. 5,338,665, which is a continuation-in-part of U.S. Pat. No. 5,270,170; the "peptides on phage" system described in U.S. patent application Ser. No. 718,577, filed Jun. 20, 1991, which is a continuation-in-part of Ser. No. 541,108, filed Jun. 20, 1990; Cwirla et al., August 1990, Proc. Natl. Acad. Sci. USA 87: 6378-6382; Barrett et al., 1992, Analyt. Biochem. 204: 357-364; and PCT Patent Pub. Nos. 91/18980 and 91/19818; the phage-based antibody display systems described in U.S. patent application Ser. No. 517,659, filed May 11, 1990, and PCT Patent Pub. No. 91/17271; the bead-based systems for generating and screening nucleic acid ligands described in PCT Pub. Nos. 91/19813, 92/05258, and 92/14843; the bead-based system described in U.S. patent application Ser. No. 946,239, filed Sep. 16, 1992, which is a continuation-in-part of Ser. No. 762,522, filed Sep. 18, 1991; and the "very large scaled immobilized polymer synthesis" system described in U.S. Pat. No. 5,143,854; PCT Patent Pub. Nos. 90/15070 and 92/10092, U.S. patent application Ser. No. 624,120, filed Dec. 6, 1990; Fodor et al., Feb. 15, 1991, Science 251: 767-773; Dower and Fodor, 1991, Ann. Rep. Med. Chem. 26:271-180; and U.S. patent application Ser. No. 805,727, filed Dec. 6, 1991. Each of the above references is incorporated herein by reference for all purposes.

Other developments relate to how the receptor is used in such screening methods. One important advance relates to the development of reagents and methods for immobilizing one or more receptors in a spatially defined array, as described in PCT Patent Pub. No. 91/07087, which describes attachment of a receptor to avidin and subsequent immobilization on a surface that bears biotin groups. Once the avidinylated receptor is bound to the biotin groups on the surface, the surface can be used in screening compounds against the receptor.

Biotin is a cofactor that is covalently attached to several enzymes involved in the transfer of activated carboxyl groups. Biotin labeling of molecules not normally biotinylated can be used to label, detect, purify, and/or immobilize such molecules. These methods also rely upon the proteins avidin and/or streptavidin, which bind very tightly and specifically to biotin. Typically, the biotinylated molecules used in such methods are prepared by an in vitro biotinylation process. Alternatively, methods for biotinylating proteins synthesized by recombinant DNA techniques in vivo eliminates the need to chemically biotinylate these proteins after purification and greatly simplifies the purification process, due to the ability to use the biotin as an affinity tag (see Green, 1975, Adv. Protein Res. 29:85-133, incorporated herein by reference).

Biotin-streptavidin interactions can also be used for linking different molecules together to form useful complexes. For example, since streptavidin has four binding sites for biotin, four biotin-labeled molecules can be linked to a single streptavidin molecule. Certain specific examples of methods comprising linkage of biotin-labeled molecules through a streptavidin molecule are described in detail in the art, e.g., in U.S. patent application Ser. No. 13/767,619, filed Feb. 14, 2013; U.S. Pat. Nos. 8,389,676; and 8,252,910, all of which are incorporated herein by reference in their entireties for all purposes. However, for some applications it is useful to generate a strong 1:1 complex of two molecules, and this can be difficult with streptavidin due to its tetravalent nature. Many different stoichiometries can be generated, e.g., 1:3 and 3:1. Methods have been previously described for creating streptavidin tetramers with reduced numbers of active sites, e.g., in Howarth, et al. (2006) Nature Methods 3(4):267-73, which is incorporated herein by reference in its entirety for all purposes. However, the methods of Howarth involve mixing of two species of recombinant streptavidin and are cumbersome.

SUMMARY OF THE INVENTION

The present invention provides useful compounds, reagents, methods, and kits for biotinylating molecules and linking biotinylated molecules together via biotin-binding agents, such as streptavidin. The invention provides compositions comprising bis-biotinylated reactants, as well as such bis-biotinylated reactants bound to a biotin-binding agent, e.g., streptavidin. In preferred embodiments, the bis-biotin tag is bound to a streptavidin or other biotin-binding agent such that the bis-biotin tag binds to two biotin-binding sites on a dimer of the streptavidin tetramer.

One aspect of the invention provides a solid support whose surface comprises multiple bis-biotin moieties. Each of the bis-biotin moieties includes two covalently linked biotin groups. In one class of embodiments, the bis-biotin moieties are noncovalently associated with the surface. In another class of embodiments, the bis-biotin moieties are covalently coupled to the surface, e.g., through siloxane bonds. The solid support can be essentially any suitable support, including, e.g., beads, microspheres, pellets, disks, chips, wafers, microparticles, and planar surfaces comprising nanoscale wells, e.g., zero-mode waveguides. In one class of embodiments, the solid support comprises nanoscale wells, the bottom surface of which comprise the bis-biotin moieties. For example, the solid support can comprise zero-mode waveguides, the bottom surface of which comprise the bis-biotin moieties. The bis-biotin moieties are optionally free.

The supports are particularly useful for immobilization of reactants of interest, e.g., through binding of the bis-biotin moiety to an agent which is in turn bound to the reactant. Thus, a biotin-binding agent is optionally bound to the bis-biotin moieties on the surface, e.g., a tetravalent biotin-binding agent (e.g., streptavidin, tamavidin, NeutrAvidin, traptavidin, or the like). A molecule or molecular complex of interest can be bound to the biotin-binding agent. In one exemplary class of embodiments, a bis-biotin tag is covalently coupled to the molecule or molecular complex of interest, and the bis-biotin tag is bound to the tetravalent biotin-binding agent that is in turn bound to one of the bis-biotin moieties on the surface. Essentially any desired molecule or complex can be immobilized in this way, including, but not limited to, a biomolecule, a polypeptide, a protein, an enzyme (e.g., a polymerase), a polymerase/template/primer complex, a nucleic acid (e.g., an oligonucleotide, DNA, RNA, DNA/RNA hybrid, nucleic acid derivative, etc.), a cofactor, a small molecule (e.g., a drug), a non-reactive component, or a label. In one exemplary class of embodiments, the solid support comprises nanoscale wells, and a biotinylated polymerase is immobilized at the bottom of each of multiple of the nanoscale wells through binding to a tetravalent biotin-binding agent, which tetravalent biotin-binding agent is bound to a bis-biotin moiety on the surface of the support.

Each bis-biotin moiety optionally includes at least two negatively charged groups, for example, sulfonic acid groups (e.g., methylsulfonic acid groups). Exemplary bis-biotin containing compositions that can be employed to modify surfaces to display bis-biotin groups are described herein. In one class of embodiments, the surface comprises a bis-biotin-PEG-silane coating.

Another aspect of the invention provides a compound having the formula

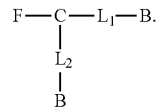

B is a biotin group. $L_1$ and $L_2$ are linking groups, which can but need not be identical, and which comprise a sulfonic acid group (e.g., a methylsulfonic acid group or a 3,4,5-tris(3-sulfopropoxy)benzoic acid group). F is a reactive functional group (e.g., a carboxylic acid, amino, azide, or alkyne group). C is a core group, a multifunctional core with multiple linking sites. In some embodiments, C comprises a six-membered ring, e.g., a tri-substituted cyclohexane ring or a tri-substituted aromatic six-membered ring, e.g., a tri-substituted triazine.

Another aspect of the invention provides a compound having the formula

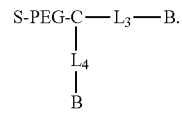

B is a biotin group. $L_3$ is a direct bond or a first linking group, and $L_4$ is a direct bond or a second linking group. $L_3$ and $L_4$ can but need not be identical, and optionally comprise a negatively charged group (e.g., a sulfonic acid moiety, e.g., a methylsulfonic acid group). C is a core group. PEG comprises a polyethylene glycol group. The PEG group typically includes 2-250 ethylene oxide units (inclusive), e.g., 8-250, 8-230, or 50-100. S comprises a silane moiety.

In yet another aspect, the invention provides methods for preparing surfaces. In the methods, a surface is coated with a compound that comprises a bis-biotin moiety, each bis-biotin moiety having two covalently linked biotin moieties. The compound (and thus the bis-biotin) can be noncovalently associated with the surface. In other embodiments, the bis-biotin moiety is covalently coupled to the surface, e.g., through reaction of the compound with the surface. In one class of embodiments, the surface comprises the bottom surface of at least one nanoscale well (e.g., zero-mode waveguide). Exemplary compounds are described herein. In one class of embodiments, the compound comprises a silane, e.g., a bis-biotin-PEG-silane. The bis-biotin moiety optionally includes at least two negatively charged groups, e.g., sulfonic acid groups (e.g., methylsulfonic acid groups).

The methods are particularly useful for preparing surfaces for immobilization of reactants of interest, e.g., through binding of the bis-biotin moiety to streptavidin or the like, which is in turn bound to the reactant. Thus, the methods optionally include binding a biotin-binding agent to the bis-biotin moieties on the surface, e.g., a tetravalent biotin-binding agent (e.g., streptavidin, tamavidin, NeutrAvidin, traptavidin, or the like). The methods can also include binding a molecule or molecular complex of interest to the biotin-binding agent. Binding the molecule or molecular complex of interest to the tetravalent biotin-binding agent can be performed before, after, or simultaneously with binding of the tetravalent biotin-binding agent to the bis-biotin moiety on the surface. In one class of embodiments, a bis-biotin tag is covalently coupled to the molecule or molecular complex of interest, and the bis-biotin tag is bound to a tetravalent biotin-binding agent that is in turn bound to one of the bis-biotin moieties on the surface. Essentially any desired molecule or complex can be immobilized in this way, including, but not limited to, a biomolecule, a polypeptide, a protein, an enzyme (e.g., a polymerase), a polymerase/template/primer complex, a nucleic acid (e.g., an oligonucleotide, DNA, RNA, DNA/RNA hybrid, nucleic acid derivative, etc.), a cofactor, a small molecule (e.g., a drug), a non-reactive component, or a label.

In certain aspects, the invention provides a composition comprising a first reactant coupled, preferably covalently coupled, to a first bis-biotin tag. In various alternative embodiments, the first reactant is a protein, label, immobilization tag, purification tag, barcode, or a solid support. In more specific embodiments, the protein is an enzyme, e.g., a polymerase; the label is a fluorescent label, spin label, or magnetic label; and the solid support is a bead or planar support, e.g., an arrayed support. The bis-biotin tag is optionally tandemly oriented or configured on a branched linker. In some preferred embodiments, biotins in a bis-biotin tag are separated by 20-60 angstroms. Optionally, the composition further comprises a streptavidin tetramer bound to the first bis-biotin tag, e.g., wherein both biotin moieties in the first bis-biotin tag are bound to the streptavidin tetramer, e.g., both are bound to one of the two dimers in the streptavidin tetramer. In some embodiments, the composition further comprises a streptavidin tetramer bound to both the first bis-biotin tag and a second bis-biotin tag. The second bis-biotin tag is typically covalently linked to a second reactant. The two biotin moieties in the second bis-biotin tag are preferably both bound to the dimer of the streptavidin tetramer that is not bound to the first bis-biotin tag.

In some aspects, the invention provides a method for colocalizing two reactants, preferably in a 1:1 stoichiometry. In certain embodiments, such an embodiment comprises (a) linking, preferably covalently linking, a first of the reactants to a first bis-biotin tag; (b) linking, preferably covalently linking, a second of the reactants to a second bis-biotin tag; (c) binding the first reactant to a tetravalent biotin-binding agent, thereby producing a first complex comprising the first reactant bound to the tetravalent biotin-binding agent; and (d) exposing the second reactant to the first complex, thereby producing a second complex comprising the second reactant bound to the first complex. Optionally, the method further comprises isolating the first complex prior to said exposing the second reactant and/or isolating the second complex. In some embodiments, the first reactant is a first member of a divalent binding pair, and the second reactant is a second member of a divalent binding pair, and further wherein production of the second complex increases binding between the first reactant and the second reactant. In specific embodiments, the first reactant is an enzyme and the second reactant is a substrate for the enzyme, and production of the second complex increases catalysis between the enzyme and the substrate. In further specific embodiments, the first reactant is a solid support and the second reactant is a molecule or molecular complex of interest, and production of the second complex immobilizes the molecule or molecular complex of interest. In yet further embodiments, the first reactant is a detectable label for detecting the second reactant, and the complex serves to link the label to the second reactant for use in a subsequent detection step. In alternative embodiments, the first reactant is an immobilization tag for immobilizing the second reactant, and the complex serves to link the immobilization tag to the second reactant for use in a subsequent immobilization step. In additional embodiments, the first reactant is a purification tag for isolating the second reactant, and the complex serves to link the purification tag to the second reactant for use in a subsequent isolation step.

In other aspects, the invention provides a labeling reagent comprising a multi-biotinylated detectable label and a tetravalent biotin-binding agent. In preferred embodiments, the multi-biotinylated detectable label comprises a bis-biotin tag. Different types of detectable labels can be used, e.g., fluorescent dyes, a spin labels, quantum dots, etc. The tetravalent biotin-binding agent is preferably a streptavidin tetramer.

In yet further aspects, the invention provides a composition comprising a multi-biotinylated reactant comprising multiple biotin moieties, wherein all of the biotin moieties are bound to a single multivalent biotin-binding agent. In certain embodiments, the multivalent biotin-binding agent is a streptavidin tetramer, e.g., having all its biotin-binding sites occupied. The tetramer is optionally bound to a second biotinylated reactant that is not the multi-biotinylated reactant. Preferably, the biotin moieties are covalently bound to one or both of the multi-biotinylated reactant and the second biotinylated reactant. In certain embodiments, each of the multi-biotinylated reactant and the second biotinylated reactant comprise a bis-biotin tag. In specific embodiments, the multivalent biotin-binding agent is a streptavidin tetramer, a first bis-biotin tag on the multi-biotinylated reactant occupies both biotin-binding sites on a first dimer of the streptavidin tetramer, and a second bis-biotin tag on the second biotinylated reactant occupies both biotin-binding sites on a second dimer of the streptavidin tetramer. The multi-biotinylated reactant can optionally be a biotinylated fusion protein having at least two biotinylation peptides, e.g. where the biotinylation peptides are in an N-terminal or C-terminal region of the fusion protein. The biotinylation peptides can be tandemly arranged, or provided in a branched configuration.

In summary, this invention provides compositions and methods for linking reactants together in a preferred stoichiometry, e.g., a one-to-one stoichiometry. The compositions and methods are useful for a variety of purposes, including, e.g., potentially wide commercial utility for research and diagnostic applications. For example, particular utility is found for the linking of labels to reactants, and localizing two reactants together, e.g., to enhance a desired interaction.

DETAILED DESCRIPTION

I. Definitions

Figure 1:
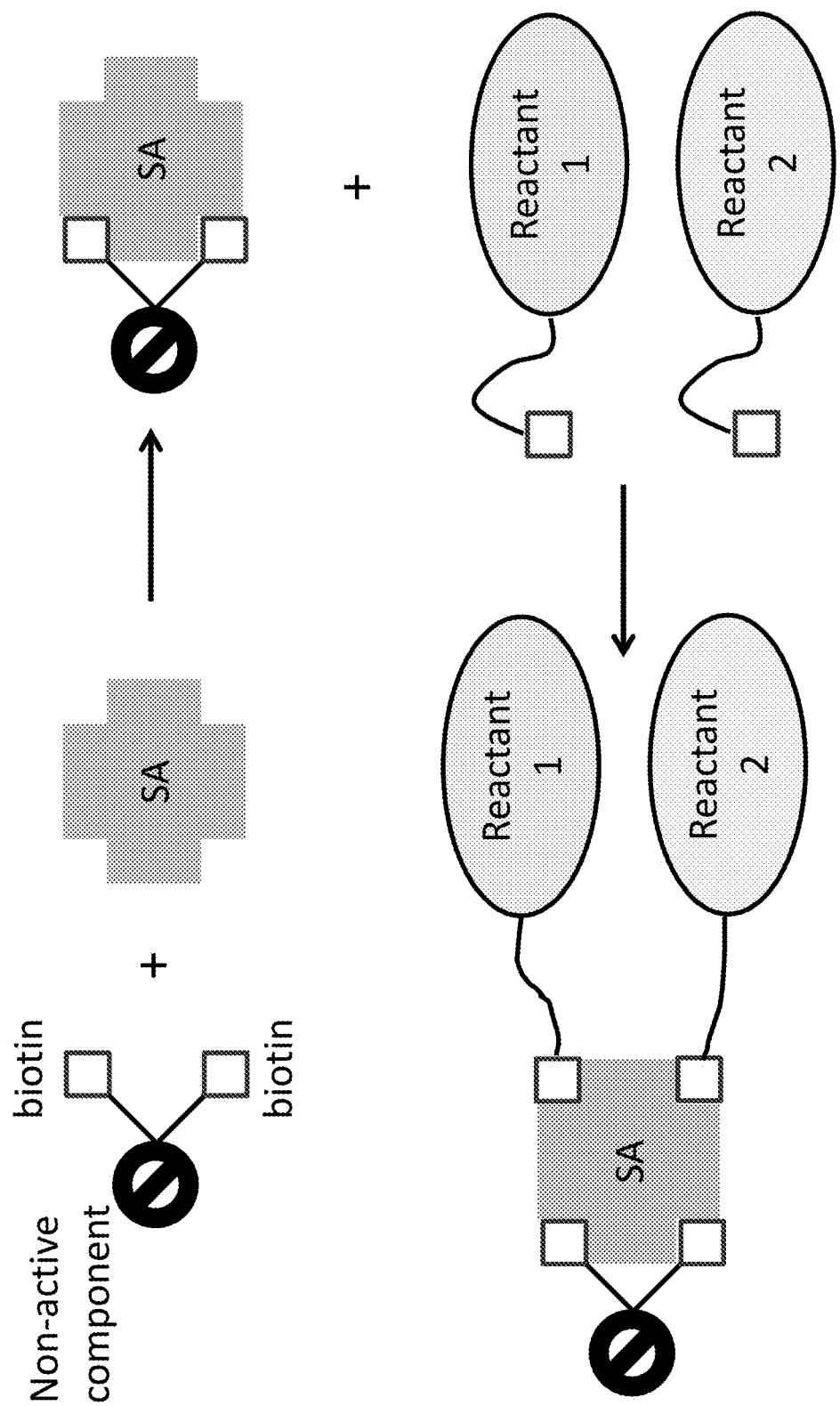
FIG. 1 illustrates a tetrameric complex comprising two binding sites blocked by a bis-biotinylated reactant and two binding sites available for further binding.

For purposes of understanding the present invention, the following terms are defined.

The terms "bis-biotin," "bis-biotin tag," "bis-Btag," and "bis-biotin moiety" can be used interchangeably and generally refer to two covalently-linked biotins linked (optionally, covalently linked) to a reactant of interest. In certain preferred embodiments, a reactant of interest comprises a sequence that is recognized by a biotin ligase, which catalyzes a covalent linkage between the sequence and a biotin molecule. Such a sequence is generally referred to as a biotin ligase recognition sequence. Each biotin ligase recognition sequence in a reactant of interest can be covalently linked to a biotin moiety, so a reactant having multiple biotin ligase recognition sequences can be covalently linked to multiple biotins. A region of a reactant having one or more biotin ligase recognition sequences is generally referred to as a biotinylation region of the reactant. For example, a bis-biotin can refer to two biotins bound to two biotinylation peptides within a fusion protein reactant.

The term "biotinylation peptide" refers to an amino acid sequence which provides a biotinylatable sequence motif. Thus, a biotinylation peptide is a peptide that is capable of being biotinylated.

The term "biotinylation sequence" refers to a nucleic acid sequence that encodes a biotinylation peptide. Thus, transcription and translation of a biotinylation sequence generates a biotinylation peptide.

The term "biotinylation enzyme" refers to the class of enzymes known as biotin protein ligases, or enzymes which biotinylate other proteins or peptides.

The term "fusion protein" generally refers to a protein which is a composite of two separate proteins which are normally not joined together as a single protein. Fusion proteins may be prepared by recombinant nucleic acid methods, i.e., as a result of transcription and translation of a gene fusion comprising a segment which encodes a biotinylation peptide and a segment which encodes one or more heterologous proteins, or by chemical synthesis methods well known in the art.

The term "host cell" refers to a eukaryotic or procaryotic cell or group of cells that can be or has been transformed by a recombinant DNA vector. For purposes of the present invention, procaryotic host cells are preferred.

The term "linker" or "spacer" refers to a molecule or group of molecules (such as a monomer or polymer) that connects two molecules and often serves to place the two molecules in a preferred configuration and/or localization, for example, so that the two molecules can have preferred interactions, e.g., with two different molecules, or two different locations on a single molecule or molecular complex.

The term "multi-biotin tag" generally refers to a tag comprising multiple biotin moieties. For example, a bis-biotin tag is a multi-biotin tag having only two biotin moieties.

The term "peptide" refers to an oligomer in which the monomers are amino acids (usually alpha-amino acids) joined together through amide bonds. Alternatively, a "peptide" can be referred to as a "polypeptide." Peptides are more than two amino acid monomers long, but more often are more than 5 to 10 amino acid monomers long and can be even longer than 20 amino acids, although peptides longer than 20 amino acids are more likely to be called "polypeptides."

The term "protein" is well known in the art and usually refers to a very large polypeptide, or set of associated polypeptides, that has some biological function. For purposes of the present invention the terms "peptide," "polypeptide," and "protein" are largely interchangeable as libraries of all three types can be prepared using substantially similar methodology.

The term "reactant" as used herein is intended to generally indicate a molecule or molecular complex of interest, e.g., a reaction component. For example, a reactant can be a component of a multi-component mixture (e.g., reaction mixture, buffer, etc.), whether or not the component directly or indirectly participates in a chemical or biochemical reaction. In certain preferred embodiments, a reactant of interest is biotinylated to facilitate further manipulation and/or analysis. A reactant can be any molecule or molecular complex, including but not limited to polypeptides, proteins, enzymes, nucleic acids (e.g., oligonucleotides, DNA, RNA, DNA/RNA hybrids, nucleic acid derivatives, etc.), cofactors, small molecules (e.g., drugs), "non-reactive" components, optical labels (e.g., fluorescent dyes), etc.

The term "solid support" refers to a material having a rigid or semi-rigid surface. Such materials will preferably take the form of small beads, pellets, disks, chips, or wafers, although other forms may be used. In some embodiments, at least one surface of the solid support will be substantially flat. In some embodiments, a solid support is a planar surface comprising nano-scale apertures, e.g., zero-mode waveguides, which are described in the art, e.g., see U.S. Pat. Nos. 7,056,661 and 7,315,019, which are incorporated herein by reference in their entireties for all purposes.

The term "surface" refers to any generally two-dimensional structure on a solid substrate and may have steps, ridges, kinks, terraces, nanoscale apertures, and the like without ceasing to be a surface. The "surface" of an object refers to the outside or uppermost layer of the object, e.g., a bead, a wafer, the bottom and/or sidewall of a well or other aperture in an otherwise planar substrate, etc.

The term "synthetic" refers to production by in vitro chemical or enzymatic synthesis.

II. Methods and Reagents of the Invention

The biotin-streptavidin linkage is one of the strongest non-covalent interactions characterized to date. The four streptavidin monomers are arranged as a dimer of dimers. As such, up to four biotin-tagged molecules (e.g., proteins, nucleic acids, small molecules, etc.) can be linked together via interaction of their respective biotin tags with a single streptavidin tetraplex. Where the object is to link multiple identical biotin-tagged molecules together, e.g., for purification purposes, this arrangement is acceptable. However, in some cases it is desired or necessary to have different biotin-tagged molecules bound to the same streptavidin molecule in a specific stoichiometry. For example, where one needs two of each type of biotin-tagged molecule bound to a single streptavidin molecule, simply combining them together in the presence of streptavidin will result in complexes having not only the desired 2:2 stoichiometry, but also 1:3, 3:1, 4:0, and 0:4. If one also takes into account streptavidin complexes that do not have all four binding sites occupied, the simple mixing strategy could also generate complexes having stoichiometries of 0:0, 1:0, 0:1, 1:1, 1:2, 2:1, 2:0, 0:2, 3:0, and 0:3, with the predominant stoichiometries influenced by reagent concentration and time. For example, a complex comprising one singly-biotinylated reactant bound to one streptavidin tetramer can be the predominant product when binding is performed with an excess of the streptavidin. Yet further, the four binding sites complicate applications in which the desired stoichiometry is actually 1:1. The inventors of the instant invention have developed a strategy for utilizing the beneficial high affinity and tight binding of the biotin-streptavidin interaction for creating complexes having a 1:1 stoichiometry.

Becket, et al. (1999, Protein Science 8:921-929), and U.S. Pat. Nos. 5,723,584, 5,874,239, 5,932,433, 6,265,552, and 8,389,676 (incorporated herein by reference in their entireties for all purposes) describe biotinylation peptides, which are peptide sequences linked to a protein of interest to provide sites for biotin labeling. Briefly, a sequence ("biotinylation sequence") encoding a biotinylation peptide is cloned into a DNA sequence encoding a protein of interest such that expression results in a fusion protein comprising the protein of interest linked to the biotinylation peptide, the latter of which is recognizable by a biotinylation enzyme, e.g., E. coli BirA. As such, the fusion protein can be biotinylated in vivo, and addition of the biotin can further facilitate purification of the fusion protein from the cell culture. The short, biotinylation peptides, whether biotinylated in vivo or in vitro, can be used for a wide variety of purposes, including purification, immobilization, labeling, and detection of the fusion proteins. A few illustrative examples include: (1) labeling receptors with biotin at a defined site, so that the labeled receptor could be, for instance, bound to streptavidin to produce a tetravalent receptor to increase the sensitivity of binding assays, such as those described in U.S. Pat. No. 5,143,854, and U.S. patent application Ser. No. 946,239, filed Sep. 16, 1992, each of which is incorporated herein by reference; (2) labeling fusion proteins containing peptide leads from any screening program, so that the labeled fusion proteins can be used to test binding of the peptide to receptors in a monovalent format (by probing with labeled streptavidin after binding occurs) or in a multivalent format (by prebinding the fusions to labeled streptavidin and then testing binding to receptors or so that the peptides can be mobilized on streptavidin-coated beads or in microtiter wells for probing with receptors, such as protease enzymes, in solution; (3) labeling peptides or proteins directly by growing cells in the presence of tritiated biotin—with a biotin auxotrophs the peptides could be labeled at a known specific activity to permit quantitative measurements of binding activity; (4) developing technology for doing enzymatic reactions on surfaces by exposing libraries of variant immobilized sequences to BirA, biotin, and ATP, so that those peptides that were substrates would be biotinylated and could be detected with labeled streptavidin; and (5) attaching biotin specifically to an enzyme such as a polymerase enzyme to allow for binding the enzyme to a surface, for example for single molecule sequencing, e.g., as described in U.S. Pat. Nos. 7,056,661 and 8,133,672, each of which is incorporated herein by reference.

Biotin-binding agents are known in the art and can be used with the methods and compositions provided herein. In certain embodiments, strategies provided herein use multiple biotin tags for linking a single reactant to a single streptavidin molecule. Streptavidin is a biotin-binding agent that has been cloned and studied extensively. See, for example, Argarana, et al. (1986) Nucleic Acids Res. 14(4): 1871-1882; Aslan, et al. (2007) Journal of Biotechnology 128:213-225; Aslan, et al. (2005) J. Proc. Natl. Acad. Sci. USA 102(24):8507-8512; Baugh, et al. (2010) Biochemistry 49:4568-4570; Gitlin, et al. (1988) Biochem. J. 256:279-282; Hendrickson, et al. (1989) Proc. Natl. Acad. Sci. USA 86:2190-2194; Hyster, et al. (2012) Science 338:500-503; Klumb, et al. (1998) Biochemistry 37(21):7657-63; Kurzban, et al. (1991) J. Biol. Chem. 266(22):14470-14477; Matsumoto, et al. (2011) J. Biotechnology 152:37-42; Sano, et al. (1996) Annals of the New York Academy of Sciences 799 (Enzyme Engineering XIII) pp. 383-390; Schmidt, et al. (1994) Journal of Chromatography A 676:337-345; Srisawat, et al. (2001) RNA 7:632-641; Tahiri-Alaoui, et al. (2002) Nucleic Acids Res. 30(10):e45; Voss, et al. (1997) Protein Engineering 10(8):975-982; and Wilbur, et al. (2004) Bioconjugate Chem. 15:1454-1463, all of which are incorporated herein by reference in their entireties for all purposes. Although many of the compositions, methods, examples, and applications described herein comprise the use or inclusion of streptavidin, e.g., for binding to biotinylated reactants, it will be understood that other biotin-binding agents (e.g., nucleic acids or other molecules or molecular complexes) can also be used, e.g., avidin, deglycoslylated avidin (NeutrAvidin), traptavidin, and variants, mutants, or derivatives thereof. For example, U.S. Pat. No. 7,981,632 describes the "strep-tag" peptide, which binds to a modified version of streptavidin, streptactin. The present invention contemplates using the reagents provided herein in combination with streptactin and/or the strep-tag. For example, streptactin can be substituted for streptavidin in applications where bis-biotin moieties can be bound to streptactin instead of single biotin moieties; alternatively, one or more strep-tag peptides can be linked to a reactant which is subsequently bound to streptactin, or to streptavidin where binding is strong enough. Linking of strep-tags to reactants can be accomplished using conventional molecular biology techniques, cloning, chemical synthesis, and the like. Yet further, peptide and nucleic acid aptamers having an affinity for streptavidin have also been developed and described in the art, e.g., in Tahiri-Alaoui, et al. (2002) Nuc. Ac. Res. 30(10):e45; and Wilson, et al. (2001) Proc. Natl. Acad. Sci. USA 98:3750-3755, both of which are incorporated herein by reference in their entireties for all purposes. Such streptavidin-binding aptamers can be linked to reactants to facilitate binding to streptavidin in a manner similar to the biotin tags described herein. For example, two linked aptamers on a single reactant can operate in a manner similar to a bis-biotin tag and provide a means of linking the reactant to two binding sites on a streptavidin molecule. Similarly, analogs or modified forms of biotin capable of binding streptavidin, avidin, or another biotin-binding agent can be employed, e.g., in a multi- or bis-tag, e.g., a biotin sulfoxide (see, e.g., Garlick and Giese (1990) "Dissociative binding of alpha- and beta-sulphoxides of biotinylamido-ethyl-3-(4-hydroxy-3-[125I]liodophenyl)propionamide to avidin" Biochemical Journal 268(3):611-613), iminobiotin, desthiobiotin (also known as dethiobiotin), oxybiotin, carbobiotin (see, e.g., Wormser et al. (1972) "Synthesis and Growth-Promoting Activity of dl-cis-Hexahydro-4-(4-carboxybutyl)-2-cyclopentimidazolone: Carbobiotin" Journal of Pharmaceutical Sciences 61(7):1168-1170), selenobiotin, carboxybiotin, homobiotin, norbiotin, diaminobiotin, biotin sulfone, epibiotin, 5-hydroxybiotin, 2-thiobiotin, azabiotin, methylated derivatives of biotin (e.g., biotin methyl ester), and/or ketone biotin. For crystal structures of various biotin analogs and modified forms, see, e.g., DeTitta et al. (1980) "Carboxybiotin translocation mechanisms suggested by diffraction studies of biotin and its vitamers" Proc Natl Acad Sci USA. 77(1):333-7 and Stallings and DeTitta (1985) "Crystallographic investigations of biotin and carboxybiotin derivatives" Ann N Y Acad Sci. 447:152-68. As such, recitation of streptavidin and biotin in various embodiments herein is merely exemplary and in no way excludes the use of other biotin- or streptavidin-binding reactants or of other biotin forms or analogs, either instead of or in combination with streptavidin and/or biotin, in the various aspects of the invention described herein, e.g., methods, compositions, and kits. As such, embodiments are contemplated that comprise different combinations of binding partners in the same complex, e.g., a reactant having a single biotin tag and a single streptavidin-binding aptamer, where the reactant binds to a streptavidin tetramer, with the aptamer bound to one binding site in one dimer of the tetramer, and the biotin bound to the other binding site in the same dimer.

Further, although various examples herein focus on binding a single multi-biotin tag to a reactant of interest, it will be understood that a plurality of multi-biotin tags can be linked to a single reactant, e.g., where binding to multiple individual biotin-binding agents is desired. For example, where a single reactant comprises two bis-biotin tags, each of the tags can bind to a different streptavidin, which can bind to other biotin-tagged reactants, e.g., other reactants, labels, solid supports, etc. Networks of multi-biotinylated reactants linked to one another through binding to biotin-binding agents is contemplated, e.g., for reconstituting catalytic pathways (e.g. metabolic or synthetic pathways), or for enhancing complex formation between multiple different reactants (e.g., components in a macromolecular complex).

In certain preferred aspects of the instant invention, both biotins in a bis-biotin tag (or the multiple biotins in a multi-biotin tag) are intended to all bind to the same biotin-binding agent, e.g., streptavidin, traptavidin, etc., to provide a stable linkage between a reactant to which the bis-biotin tag is covalently bound and the biotin-binding agent. Whereas "bis-biotin linkers" are described by Ringler and Schulz (2003) Science 302, 106-109 (incorporated herein by reference in its entirety for all purposes), they are used as a linkage between two different molecules, each of which has a biotin-binding site. In other words, the two biotins on the bis-biotin linker are intended to noncovalently bind to two different molecules, thereby connecting them via the linker. As such, neither of the molecules is covalently linked to the bis-biotin linker. Other multi-biotin linkers, termed "biotinylated starburst dendrimers," are described in Wilbur, et al. (1998) Bioconjugate Chem. 9:813-825 and U.S. Pat. No. 7,141,676 (incorporated herein by reference in their entireties for all purposes) for use in cancer pretargeting protocols. Once again, these dendrimers did not comprise a covalent linkage to a reactant of interest, but rather noncovalently connected molecules in vivo. Additional bis-biotin linkers are described by Wilbur, et al. (1997) Bioconjugate Chem. 8:819-832 (incorporated herein by reference in its entirety for all purposes); and although in some embodiments two biotins in a tris-biotinylated linker both bound to the same streptavidin molecule, the third biotin bound to a different streptavidin molecule, e.g., in order to form a molecular network of linkers and streptavidin tetramers. As such, not all biotins in the multi-biotinylate linker are bound to the same streptavidin tetramer. In certain preferred embodiments of the present invention, the bis-biotinylated reactant of the invention is not merely a linker comprising two (or more) biotins, but is instead a molecule that has a specific interaction/reaction with another component in a reaction mixture. In further preferred embodiments of the instant invention, all the biotins on a multi-biotinylated reactant bind to the same biotin-binding agent, e.g., molecular complex such as a streptavidin dimer or tetramer. As such, a preferred complex comprising a multi-biotinylated reactant of the invention further comprises only a single biotin-binding agent.

In certain preferred embodiments, a reactant is modified to add two biotinylation peptides, and two biotin molecules are subsequently bound to the biotinylation peptides (e.g., using a biotin ligase enzyme) to provide a bis-biotin tag on the reactant. Where the reactant of interest is a protein, multiple, preferably tandem sequences encoding biotinylation peptides are cloned into a DNA sequence encoding the protein of interest such that expression results in a fusion protein comprising the protein of interest linked to the multiple biotinylation peptides, which are subsequently biotinylated. In preferred embodiments, the two biotinylation peptides occur within a single "biotinylation region," e.g., at one end of the reactant of interest, preferably tandemly arranged. For example, with a protein of interest, a biotinylation region is preferably at the C-terminal or N-terminal end of the protein. In alternative embodiments, two separate biotinylation regions can be engineered into a reactant of interest, where each comprises a single biotinylation peptide. For example, one could be at the C-terminus of a protein, while the other is at the N-terminus. The location of biotinylation regions within a reactant of interest is not limited to the ends, and can occur internal to the reactant, as well. However, where it is required that the reactant maintain a given activity, the location of the biotinylation peptides, and eventual location of the biotin moieties, cannot interfere with this activity. It is well within the skills of the ordinary artisan to determine which portions of a given reactant are necessary for its activity, and which portions are amenable to such modification.

Preferably the biotinylation occurs in vivo, which provides biotin tags that can be used to purify the fusion protein from a cell extract. In other embodiments, it can be carried out in vitro at some point during the lysis and purification process. Following biotinylation and isolation of the biotin-tagged protein, the two biotin molecules (bis-biotin moiety) that are now bound to the biotinylation peptides can be further bound to two adjacent sites (e.g., on the same dimer) on a streptavidin tetramer. Introduction of streptavidin results in assembly of a protein-biotin-streptavidin complex that has two open binding sites on the streptavidin tetramer, which can be bound to biotins linked to another reactant having at least two biotin tags, or bound to two other biotinylated reactants. Alternatively, the streptavidin introduced may already be bound to another molecule, e.g., a mono-biotin or bis-biotin-tagged reactant. In certain preferred embodiments, the streptavidin is already bound to a single, bis-biotin-tagged label (e.g., fluorescent dye).

Particularly preferred compositions of the invention comprise a single streptavidin molecule having all four binding sites occupied, but bound to only two reactants in a 1:1 stoichiometry, e.g., where each of the two reactants is linked to the streptavidin molecule via two biotin tags. For example, binding of a bis-biotin-tagged protein to a bis-biotin-labeled streptavidin (streptavidin bound to a label (e.g., fluorescent dye molecule) having a bis-biotin tag) results in a complex having a 1:1 stoichiometry with respect to the two bound molecules, i.e., the protein and the label, since only one protein and one label are bound to the streptavidin tetramer. The linkage between the protein of interest and the label, via the streptavidin tetramer, can be subsequently used to identify or otherwise detect the protein during further analysis. Although a label is bound to the streptavidin in this example, the streptavidin can be bound to any molecule that one wishes to link to the protein of interest, e.g., another protein, a nucleic acid or nucleotide, a small molecule or drug, gold or other metallic particle, antibody or antigen, affinity tag, RFID tag, barcode (e.g., nucleic acid or polypeptide barcode), or a different type of label (e.g., mass label, spin label, etc.). Further, the streptavidin can alternatively be linked to a surface, e.g., through a bis-biotin linkage, e.g., for purification or other manipulation of the protein. Surfaces contemplated include, but are not limited to, beads (e.g., magnetic beads), columns (e.g., for chromatography), microarrays, semi-solid surfaces, waveguide substrates, within nanoholes (e.g., at the bottom of zero-mode waveguides) on an array, etc.

A bis-biotin tag can be arranged in a linear or branched orientation, depending on the structure of the reagent to be tagged. A linear orientation is preferred where the reactant is a fusion protein having biotinylation peptides oriented in tandem, with or without spacers in between them, at one end of the fusion protein. Such a fusion protein can be expressed in vivo where biotinylation sequences are added to the gene for a peptide of interest, similar to the method of adding a single biotinylation peptide to a protein of interest described above. A branched orientation can be provided using conventional biochemical methods, e.g., by biochemically synthesizing a branched linker having two biotinylation peptides, each on a separate branch. This synthetic linker is bound to a reactant of interest and, preferably, subsequently biotinylated to provide a branched bis-biotin tag.

Streptavidin is a dimer of dimers. There is a distance of about 19-20 Angstroms between the carboxyl moieties of biotins bound to the two binding sites on one of the two dimers, i.e., "adjacent biotins." (Similar distances are also found for tamavidin and avidin.) As such, a distance or "linker length" between the two biotins of a bis-biotin moiety of about 19-20 Angstroms or greater is able to accommodate binding of both biotins to binding sites on a streptavidin dimer. Since, fully extended, the 15 amino acids of the biotinylation peptides can span over 50 Angstroms, tandemly repeated biotinylation peptides in a fusion protein provide more than enough of a distance between the subsequently bound biotin moieties to allow binding to adjacent binding sites on one of the two streptavidin dimers, as long as the secondary and/or tertiary structure of the polypeptide region between the bound biotin moieties does not shorten the actual distance between them to less than 19-20 Angstroms. Where the linker length is too short to allow binding of both biotins, the construct would favor daisy-chaining of streptavidin tetramers, where one biotin of the bis-biotin would bind to one streptavidin complex and the other biotin would bind to a second streptavidin complex, thereby linking the two streptavidin complexes together. As such, in preferred embodiments the biotinylation region of a reactant provides a distance between bound biotin moieties of at least 20 Angstroms, more preferably at least 25, 30, 35, 40, 45, 50, or 60 Angstroms. Likewise, where the biotins in the bis-biotin tag are too far apart, daisy-chaining of streptavidin molecules once again becomes favored over binding of both biotins to the same streptavidin dimer. More information on daisy-chaining of streptavidin can be found in Ringler and Schulz (2003) Science 302, 106-109, incorporated herein by reference in its entirety for all purposes. As such, in preferred embodiments, the linker length is about 20-70 angstroms, more preferably about 20-60 angstroms. Given a flexible linking portion of the reactant of interest, the linker length can also change as the linking portion bends and flexes, as will be understood by those of skill in the art. Further, secondary and tertiary structure of a polypeptide linker will change the actual distance between two biotin moieties, so the distances provided here refer to the distance that is spanned in order to bind both biotin moieties to desired binding sites, e.g., on a streptavidin complex, and are not necessarily "stretched out" lengths of a linker, e.g., based upon its primary structure.

In other embodiments, a single reactant can be tagged with three biotins, i.e., a "tris-biotin" tag. The tris-biotin-tagged molecule is bound to a streptavidin molecule, leaving a single binding site open for a single mono-biotin-tagged molecule. Similar to the two-bis-biotin-tagged strategy, this strategy also provides for a 1:1 stoichiometry of molecules bound to a single streptavidin molecule. However, the spacing between the bound biotins must be able to accommodate the span from one side of the streptavidin molecule, where two binding sites are occupied, to the other side where the third site will be occupied. The distance between biotin-binding sites on different dimers of the streptavidin complex is 29.6 Angstroms, and that distance goes through the center of the tetramer complex rather than wrapping around the outside as would be required for a tris-biotin complex. In order for a tris-biotin tag to occupy both biotin-binding sites on one dimer and reach to the other side for a biotin-binding site on the other dimer, the linker would need to accommodate a distance of about 70 Angstroms, and would need to be flexible enough to allow the curvature required to wrap around the complex. One disadvantage to using a tris-biotin tag is that it's more likely to bind to two streptavidin molecules rather than three binding sites on a single tetramer, which can cause the daisy-chaining of streptavidin molecules, but the likelihood of this occurring is dependent on the concentration of streptavidin and the tris-biotinylated reactant.

The inventors have recognized the value of using multi-biotinylated reagents to effectively change the valence of a tetravalent binding partner (e.g., streptavidin, traptavidin, avidin, NeutrAvidin, etc.) such that it functions as a divalent binding partner by linking multiple biotin moieties to a single reactant such that multiple binding sites are blocked on the tetravalent binding partner when the reactant is bound. For example, binding these reagents to streptavidin molecules effectively reduces the number of unoccupied binding sites on the tetramer to facilitate the construction of homo- or hetero-dimers of biotinylated reactants. In preferred embodiments, binding of a bis-biotinylated reagent to streptavidin blocks two binding sites on the tetramer while two binding sites remain unoccupied. This bis-biotinylated streptavidin tetramer can subsequently be used to construct a complex having a 1:1 stoichiometry for reactants bound to the streptavidin tetramer by introducing a second reactant that is also bis-biotinylated. A variety of schemes are possible, and certain preferred embodiments are illustrated in FIGS. 1-7. Other uses of bis-biotin binding reagents are described in Wilbur, et al. (1997, Bioconjug. Chem. 8(6): 819-832) and International Patent Publication No. WO 1999/060400, both of which are incorporated herein by reference in their entireties for all purposes.

In a simple embodiment, a bis-biotinylated reactant is a non-reactive component that serves to block two of the sites on a tetrameric complex. This results in a tetrameric complex having only two binding sites available for further binding as illustrated in FIG. 1. The tetrameric complex bound to the bis-biotinylated reactant can be subsequently used as a divalent binding partner to link together two mono-biotinylated reactants in a 1:1 stoichiometry, which can be the same reactant to produce a homodimer, or different reactants to produce a heterodimer. In the latter case, mixtures of products can be obtained (e.g., comprising both homo- and hetero-dimers) and subsequent purification steps are performed to isolate the desired combination. FIG. 1 illustrates a branched, bis-biotin moiety linked to a non-reactive component, which is exposed to a tetrameric streptavidin to produce a complex having only two open biotin-binding sites. Two mono-biotinylated reactants (Reactant 1 and Reactant 2) are introduced, either simultaneously or serially, and each binds to one of the open biotin-binding sites. Reactant 1 and 2 can be different reactants, or can be identical reactants, as noted above. This method is especially beneficial when it is desirable to colocalize Reactant 1 and Reactant 2, e.g., to increase the kinetics of a reaction between them. For example, colocalization of two components of a biochemical reaction will promote the reaction by increasing the likelihood the two components will interact with one another, e.g., an enzyme is likely to react more quickly with a colocalized enzyme substrate that an enzyme substrate free in solution. Similarly, where it is desirable to link two reactants together, colocalizing them will facilitate the linkage by increasing their local concentration with respect to each other. Yet further, colocalizing reactants that act in concert, e.g., in a metabolic pathway or as a cofactor/enzyme pair, is beneficial since the colocalization increases the efficiency of their cooperative functions. (These benefits of colocalization apply equally well to other specific embodiments described herein, such as those in which two bis-biotinylated reactants are bound to the same streptavidin molecule, as further described below.) As noted elsewhere herein, other binding partners can also be used in the compositions and methods described herein. For example, the bis-biotin moiety in FIG. 1 could be replaced with two strep-tag peptides and the streptavidin could be replaced with a streptactin molecule, e.g., as described in U.S. Pat. No. 7,981,632.

Figure 2:
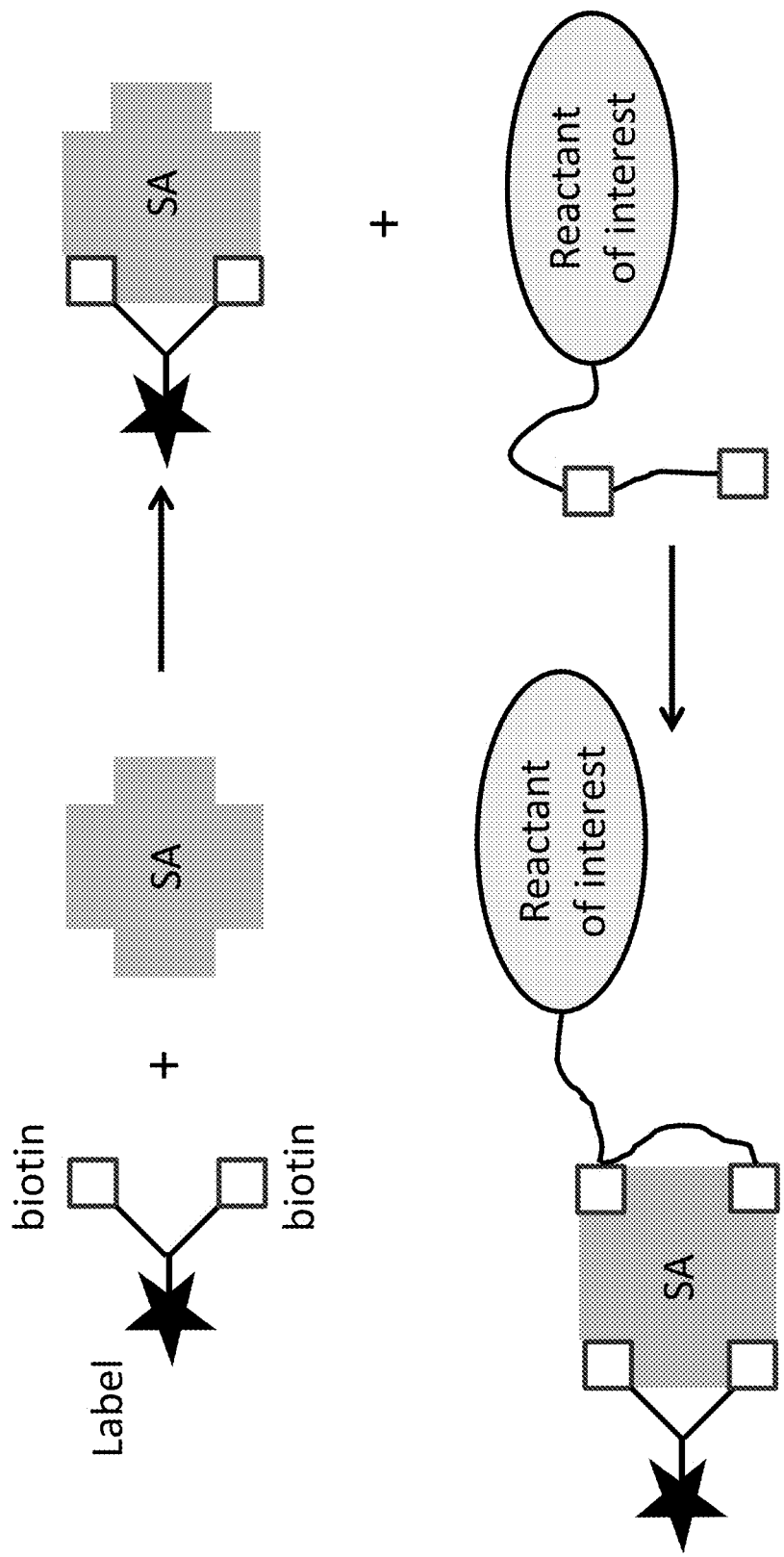
FIG. 2 illustrates a labeling reagent comprising a bis-biotinylated detectable label bound to a tetravalent streptavidin.
Figure 3:
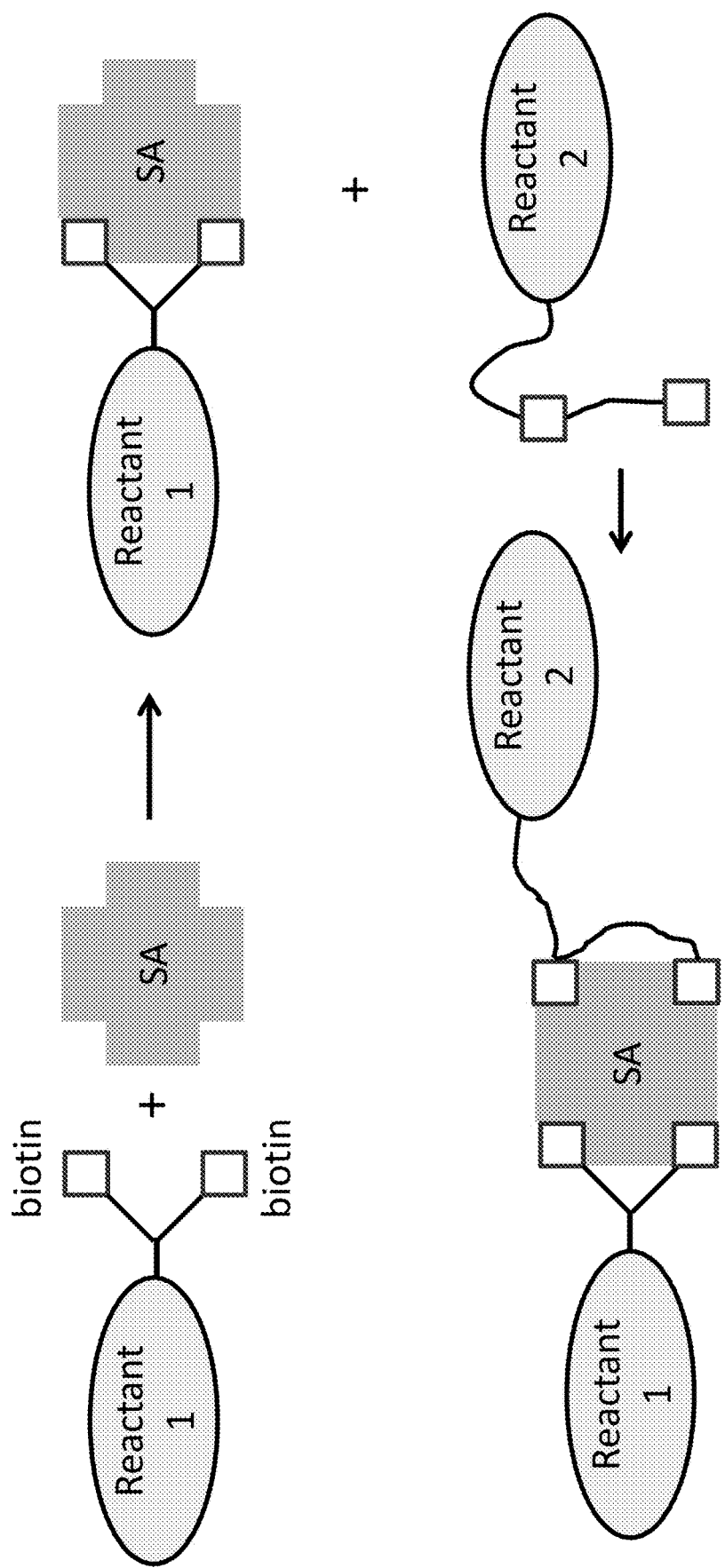
FIG. 3 provides an illustrative embodiment of colocalization of two reactants (Reactant 1 and Reactant 2) by bis-biotinylating both reactants and binding both, either simultaneously or sequentially, to a tetravalent complex.

In another embodiment, a non-reactive component can be a detectable label (e.g., fluorescent dye) is bis-biotinylated and bound to a tetravalent streptavidin to produce a labeling reagent as illustrated in FIG. 2. A bis-biotinylated reactant of interest is combined with this labeling reagent to produce a complex wherein the reactant of interest is linked to the detectable label in a 1:1 stoichiometry. This strategy can be used to differentially label any number of different reactants by exposing them to labeling reagents having different detectable labels. The labeled reactants can be subjected to further analysis that uses the labels, e.g., to track or quantitate the reactant in an experimental system. Although a fluorescent dye is provided as an exemplary detectable label, other detectable labels can also be used in this application, e.g., mass labels, spin labels, quantum dots, metallic particles, and others known in the art and/or described elsewhere herein.

In related embodiments, other bis-biotinylated moieties can be linked to reactants of interest through binding to a tetravalent complex. For example, rather than a detectable label the streptavidin can be bound to a nucleic acid barcode, polypeptide barcode, or RFID tag to form an identification tag, which is then linked to a reactant of interest. In another application, an affinity or "purification" tag is bis-biotinylated and bound to a streptavidin to be used as an affinity reagent useful for capturing biotinylated reactants of interest bound to the streptavidin. In certain preferred embodiments, an affinity tag is a magnetic bead that is immobilized proximal to a magnet or an antibody that binds to an antigen on a surface. Immobilization of the affinity tag, e.g., to a magnet or antigen-coated surface, respectively, allow removal of components of a mixture that are not bound to the streptavidin, i.e., that are not the reactant of interest. Other types of purification tags include, but are not limited to, FLAG tags, reactive moieties (e.g., thiol or SNAP tag labels). In further embodiments, such labeling reagents (or affinity tags or identification tags) comprising two available binding sites are used for dual purposes, e.g., to both colocalize two mono-biotinylated reactants and label that colocalized pair. For example, with reference to FIG. 1, the non-reactive component could be a label (or other tag), in which case the two reactants would not only be colocalized, but also linked to the label or tag, e.g., for tracking, quantitation, isolation, identification, etc. In yet further embodiments, the non-reactive component could be an immobilization tag, e.g., an agent that binds directly or indirectly to a solid surface. In such embodiments, the reactant or reactants of interest can be bound to the complex either prior or subsequent to immobilization of the tetrameric complex.

In another aspect of the invention, colocalization of two reactants is provided by providing bis-biotin tags on both reactants and binding both, either simultaneously or sequentially, to the tetravalent complex. An exemplary illustration is provided in FIG. 3, where Reactant 1 is bound to both binding sites of one of the streptavidin dimers, and Reactant 2 is bound to the two binding sites on the other dimer. This figure depicts Reactant 1 with a branched biotinylation tag, and Reactant 2 with a linear biotinylation tag, but the method is also operable with both having linear tags, or both having branched tags. Where direct interaction between the reactants is an object of the complex, the length of the linkers connecting the reactants to their component tags is designed to provide sufficient movement to allow that interaction. For example, where one reactant is a cofactor or substrate and the other is an enzyme, the linkers are sufficiently long to allow productive interaction between the reactants, e.g., to promote enzyme activity. Similarly, where the reactants are to be directly joined together, e.g., for attachment of a tag (reactant 1) to a molecule of interest (reactant 2), the linkers are sufficiently long to allow the reactants to orient with one another in a configuration that promotes the joining. Since the two reactants use all four binding sites, a biotin- or bis-biotin-tagged label cannot also be bound to the biotin-binding sites on the dimers of the streptavidin, but a label or other tag can be linked to other sites in the complex (e.g., other regions of the streptavidin tetramer) by methods known and routine in the art.

Figure 4:
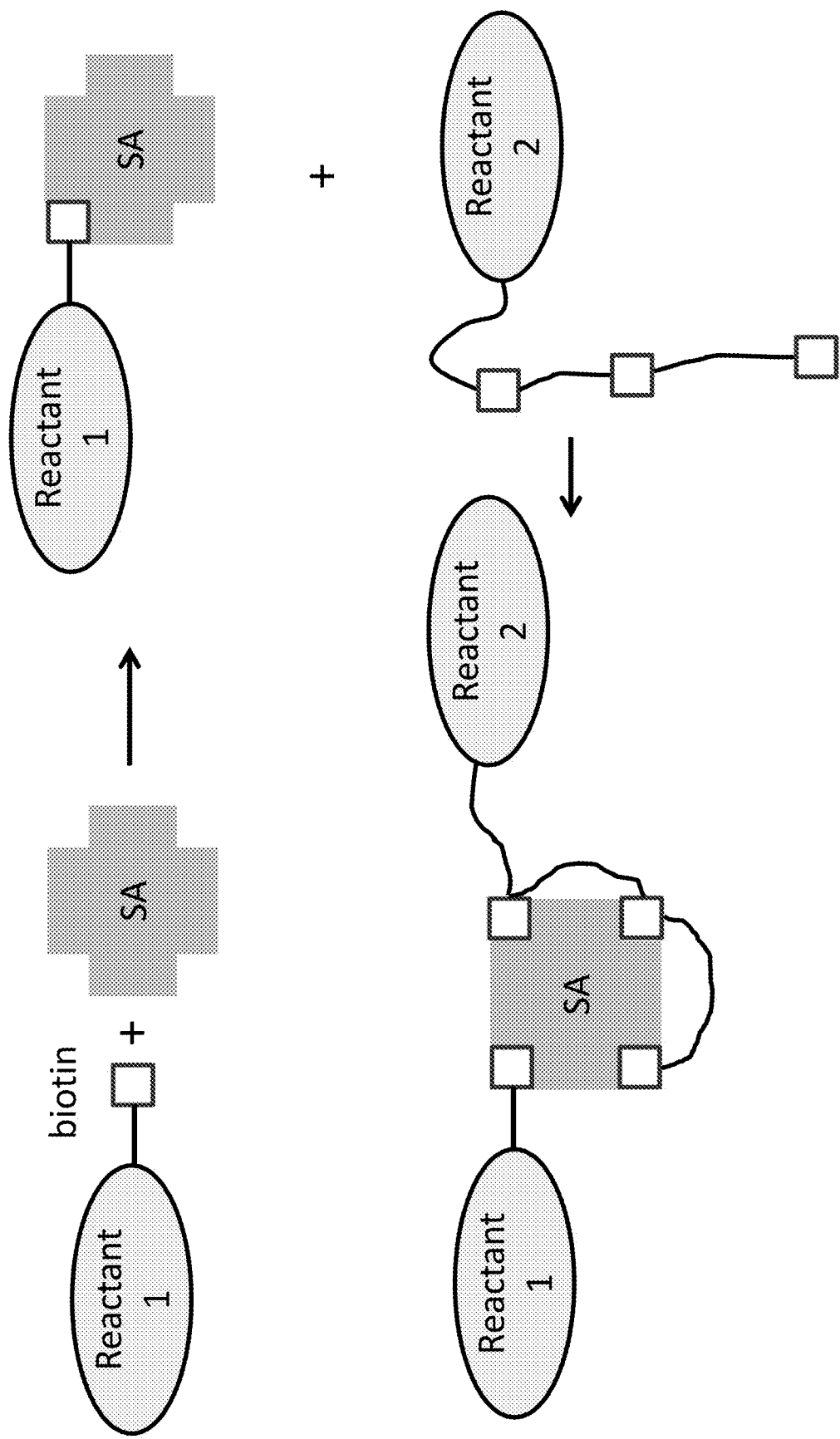
FIG. 4 provides an illustrative example of a method of using a tetravalent complex to link two reactants together with a 1:1 stoichiometry wherein one reactant is tris-biotinylated and the other reactant is mono-biotinylated.

FIG. 4 provides an illustrative example of another method for using the tetravalent complex to link two reactants together with a 1:1 stoichiometry wherein one reactant is tris-biotinylated and the other reactant is mono-biotinylated. Since there are only four binding sites on the streptavidin tetramer, only one of each type of biotinylated reagent can be bound to a single tetramer. Which reagent has the tris-biotin tag and which has the mono-biotin tag depends on the needs of the practitioner and the requirements for strong and stable binding of each. For example, where a subsequent reaction takes place in the presence of one of the reagents, that reagent can be chosen to be the mono-biotin-tagged reagent so that upon dissociation during the reaction another molecule of the reagent is readily available to bind to the open binding site. In preferred embodiments, the tris-biotinylated reagent is bound to the streptavidin first. This order ensures that only a single one of the mono-biotinylated reagents binds because only a single binding site is available after binding of the tris-biotinylated reagent. As in the above-described embodiments, the reactants can be any reactants that are amenable to such biotinylation, e.g., nucleic acids, proteins, drugs, carbohydrates, cofactors, detectable labels, affinity tags, identification tags, immobilization agents, and the like.

Highly negatively or positively charged proteins (also termed "supercharged" proteins; see, e.g., Thompson, et al. (2012, Methods Enzymol. 503: 293-319, incorporated herein by reference in its entirety for all purposes) have superior properties in folding, lack of aggregation, and the being taken up by cells (in the case of the positively charged ones). In certain aspects, the present invention provides "supercharged" macromolecular complexes that have many useful properties similar to those of supercharged proteins. In certain preferred embodiments, a highly charged moiety is bis-biotinylated and bound to a streptavidin tetramer to leave two open binding sites. A reactant of interest, e.g., a protein, nucleic acid, small molecule, label, or any other reagent that the practitioner wishes to link to the highly charged moiety, is also bis-biotinylated and bound to the two open binding sites. This configuration provides a 1:1 stoichiometry between the highly charged moiety and the reactant of interest. In alternative embodiments, the number of biotins on the highly charged moiety and/or the reactant can be varied. Alternatively or in addition, multiple, mono-biotinylated reactants and/or highly charged moieties can be bound to the complex. For example, the highly charged moiety can be bis-biotinylated while two bound reactants each have only a single biotin tag, or vice versa. In certain preferred embodiments, the highly charged moiety is a highly negatively charged moiety, such as a polyphosphate chain. For example, highly negatively charged polyphosphate groups are very stable given a bis-biotin tag linked to streptavidin.

As noted above, although described primarily in terms of a streptavidin tetramer bound to biotinylated reagents, it will be clear to the ordinary practitioner that streptavidin can be replaced with tamavidin, NeutrAvidin, and other multivalent molecules mentioned herein and known in the art that have a high affinity for biotin. See, e.g., Takakura, et al. (2009) FEBS Journal 276:1383-1397, incorporated herein by reference in its entirety for all purposes. Alternatively, other high-affinity binding partners (e.g., streptactin and the strep-tag peptides) can be used in the place of the streptavidin-biotin combination. Further, where the complex is intended to link a detectable label to a single biotinylated reactant, the biotinylated reactant could comprise four biotin tags that occupy all four binding sites of the streptavidin (or other multivalent biotin-binding partner) where the label is linked to the streptavidin at a different location, e.g., through surface lysines such that the linkage does not interfere with the binding of the single tetra-biotinylated reactant.

Figure 5:
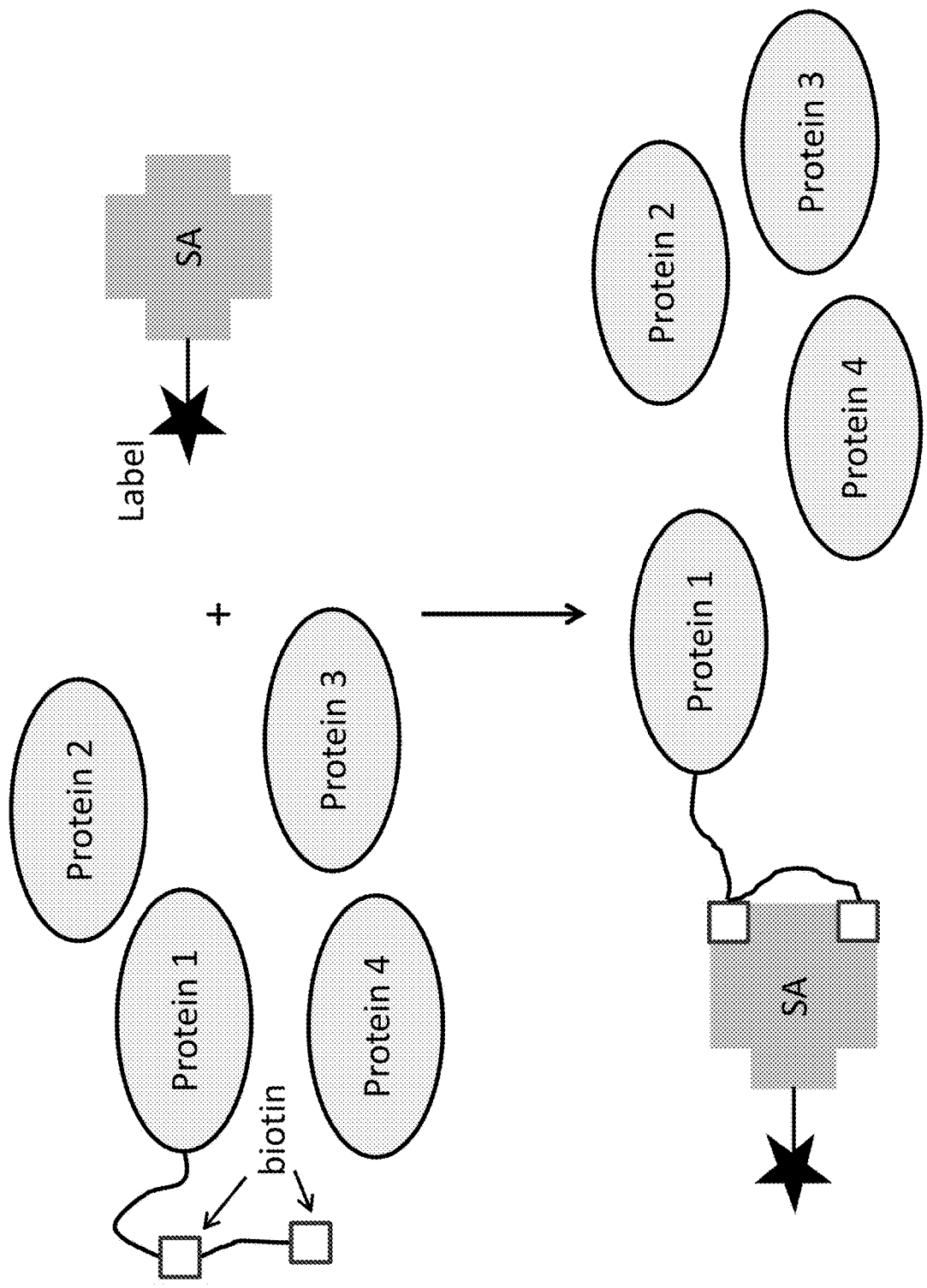
FIG. 5 provides an illustrative example of an embodiment of the invention, wherein a bis-biotinylated protein of interest (Protein 1) binds to a streptavidin bound to a body-linked label while non-specific proteins remain unbound (Proteins 2, 3, and 4).

The methods and compositions provided herein are also useful in identification and quantification of a protein of interest in a complex mixture. As described above, a protein of interest is first cloned with tandem sequences encoding biotinylation peptides. The cells containing the sequences encoding the protein and biotinylation peptides are grown and lysed. The lysate is exposed to biotin and a biotinylation enzyme to add biotin moieties at the biotinylation peptides, and subsequently incubated with a complex comprising a streptavidin linked to a detectable label. The detectable label can be mono-biotinylated and bound to one biotin-binding site on the streptavidin tetramer, or can be linked to the streptavidin in a manner that does not block any of the biotin-binding sites (e.g., "body-labeled"). FIG. 5 provides an illustrative example of the method, showing how a bis-biotinylated protein of interest (Protein 1) binds to a streptavidin bound to a body-linked label (i.e., linked to a portion of the streptavidin tetramer that is not a biotin-binding site) while non-specific proteins remain unbound (Proteins 2, 3, and 4). The lysate is then incubated for 20 minutes at 90° C. in the presence of SDS (sodium dodecyl sulfate) or other appropriate detergent, and subsequently subjected to electrophoresis. Only the streptavidin tetramers that have tandem biotins bound (i.e., a bis-biotin bound to both biotin-binding sites on one of the streptavidin dimers in the tetramer) remain tetrameric. Those streptavidin tetramers with no bis-biotin bound fall apart, mostly into monomers, by the harsh treatment. Although there is some literature on thermal stabilization of streptavidin by biotin, this finding is a surprising result, since the ordinary artisan would not have expected that binding of one bis-biotin tag to one dimer of a streptavidin tetramer to stabilize the entire tetramer under such extreme conditions. For example, Holmberg, et al. reported that biotin-streptavidin interactions can be disrupted in a nonionic aqueous solution at a temperature above 70° C. (Electrophoresis 2005, 26:501-510), and Xia, et al. showed experiments in which about half of streptavidin tetramers in a solution unfolded after only about 9±1 to 11±2 minutes at 70° C., depending on the method of calculation (Biochemistry (2012) 51:100-107), both of which are incorporated herein by reference in their entireties for all purposes. It was unexpected that a single bis-biotinylated reactant could stabilize a streptavidin tetramer in the presence of SDS, for 20 minutes at 90° C., and specific details of the experiments revealing this unexpected result are provided in the Examples herein. The concentration of the remaining streptavidin tetramers is proportional to the amount of the protein of interest in the lysate and can be quantitated through standard scanning techniques that detect the amount of label present in the band corresponding to the tetrameric streptavidin. That is, the amount of label present is proportional to the amount of tetramer present, which is proportional to the amount of the protein of interest present in the lysate. The label present in the other band(s) on the gel represents the label bound to streptavidin that fell apart during the high-heat incubation in SDS. Optionally, to ensure a 1:1 stoichiometry between the body-labeled tetramer and the bis-biotinylated protein (which could bind to both dimers), one or two biotin binding sites on one of the streptavidin dimers can be blocked, e.g. using a mono-biotinylated non-reactive component, prior to exposure to the cell lysate. Alternatively, during gel analysis the complexes having two proteins bound will migrate in a separate band, and the amount of protein in the slower-migrating band will be computed to account for two proteins for each label. In embodiments using a mono-biotinylated label, the label itself can serve to block binding of the bis-biotinylated protein to one of the two dimers, leaving the other dimer available for binding. Optionally, a non-reactive, mono-biotinylated component can be bound to the second binding site of the dimer to which the label is bound. More preferably, purification methods, e.g., mass-based methods, are used to ensure that the labeled streptavidin has only a single mono-biotinylated label bound prior to binding the protein of interest. Yet further, where the existence of two labels detectably changes the migration of the complex, the extra purification step is unnecessary since the amount of protein of interest in the band corresponding to the double-labeled complex is analyzed to take into account that a single protein corresponds to two labels in that band.

Figure 6:
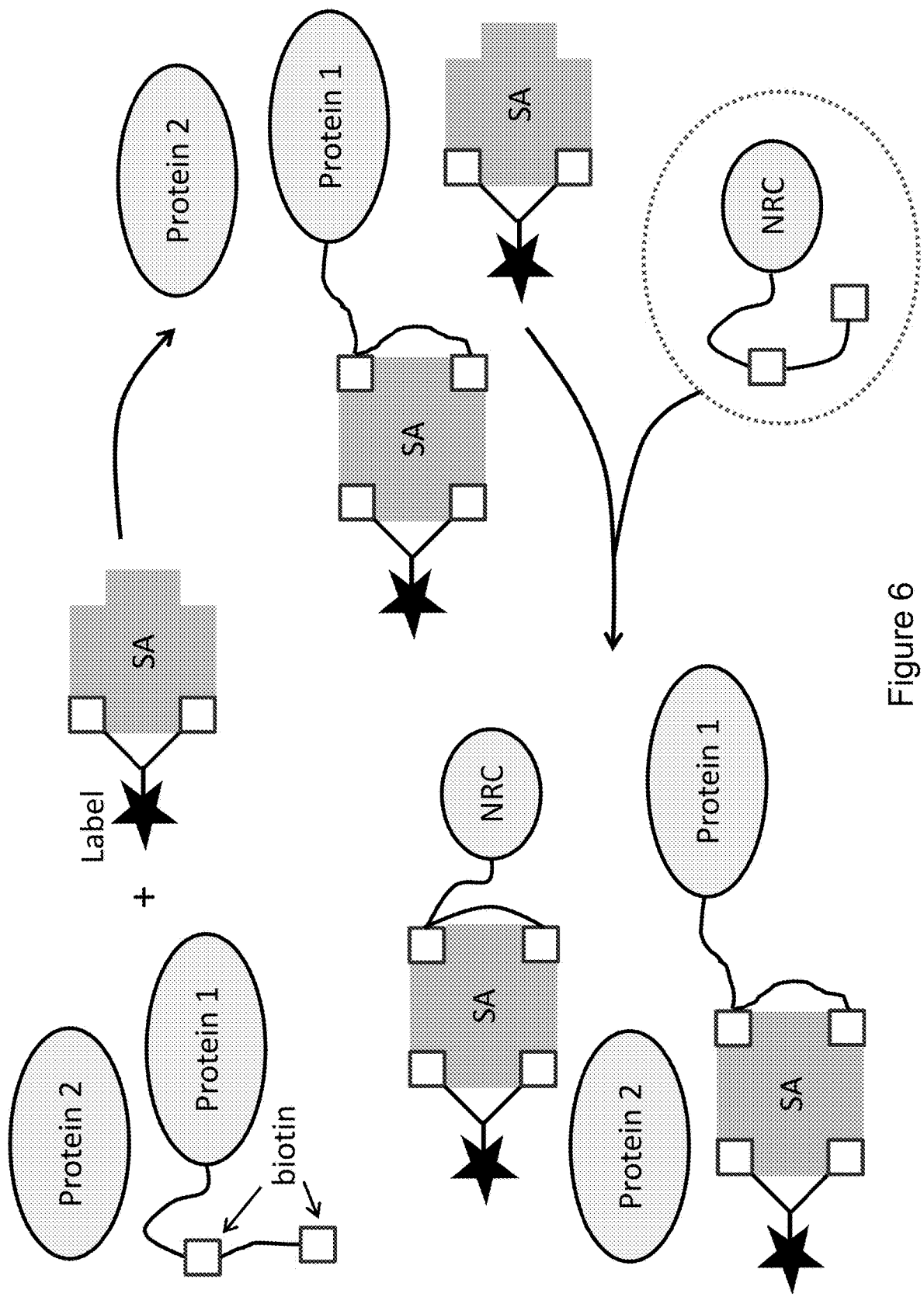
FIG. 6 illustrates an embodiment of a gel separation strategy for separating different streptavidin tetramer complexes.
Figure 7:
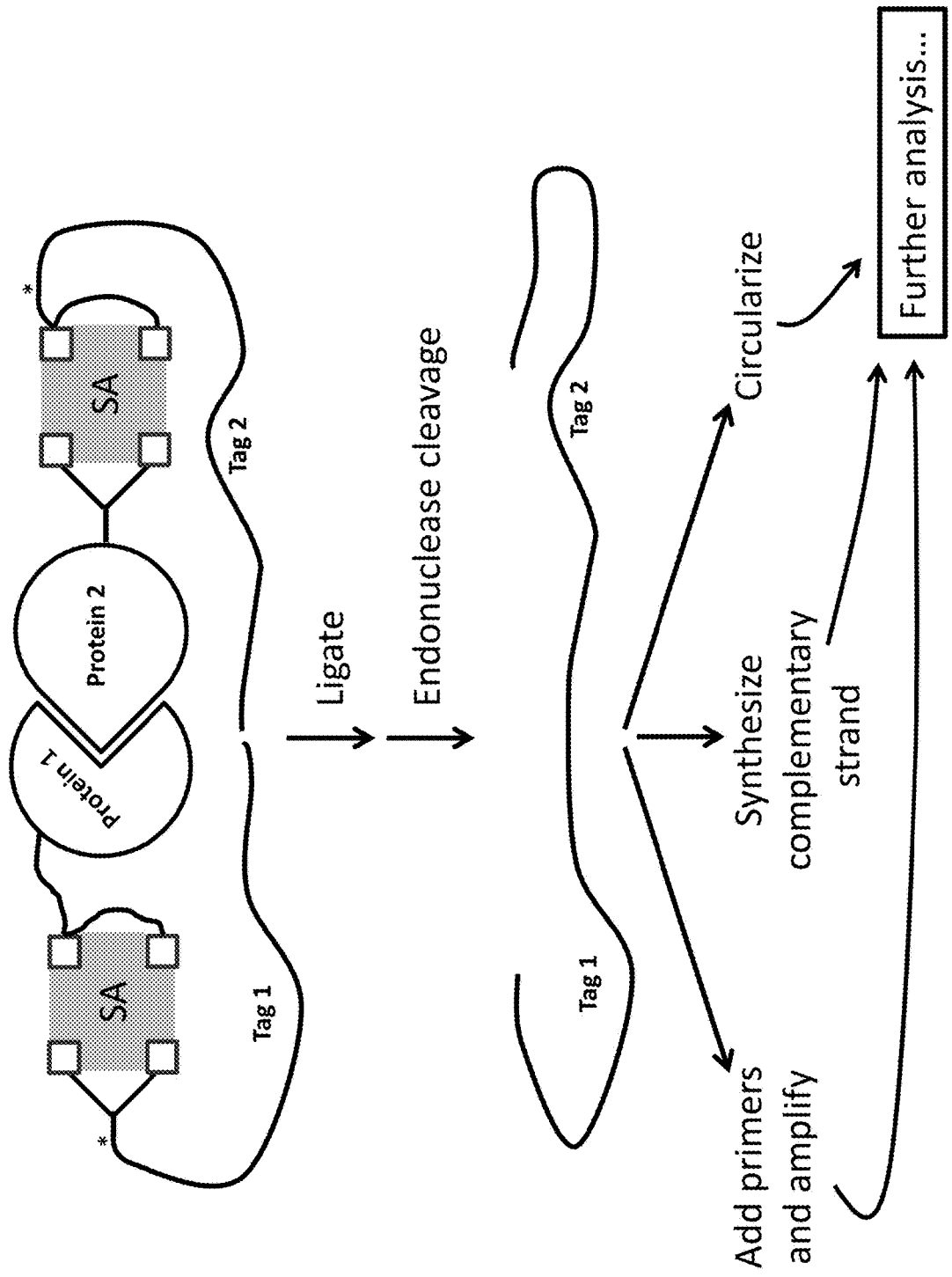
FIG. 7 provides an illustrative embodiment in which Protein 1 and Protein 2 are each bound via a bis-biotin linkage to a different streptavidin tetramer, each comprising a nucleic acid tag, Tag 1 and Tag 2, respectively.

In alternative embodiments, the detectable label bound to the streptavidin is bound at two binding sites via a bis-biotin tag. This mode provides a cleaner 1:1 stoichiometry between the protein of interest and the dye, which improves the calculation of the amount of the protein that is present in the tetramer band because the availability of only two binding sites for the protein of interest ensures that only a single one will bind to the streptavidin tetramer. This strategy requires a slightly more complex gel separation step since the bis-biotinylated label will hold the tetramer together during a high-heat detergent incubation whether or not the protein of interest is bound. An embodiment of an appropriate gel separation strategy is illustrated in FIG. 6, which shows the two streptavidin tetramer complexes: one with only the bis-biotinylated dye bound, and the other with both the bis-biotinylated dye and the bis-biotinylated protein of interest (Protein 1) bound. A non-specific "contaminating" protein (Protein 2) is also shown. Following electrophoresis, the gel will show two bands that correspond to these two dye-labeled complexes. If the complex comprising the protein of interest migrates at a distinctly different position on the gel, the practitioner can readily distinguish which band should be analyzed to measure the quantity of this protein. However, if the two complexes migrate together or very close to one another, an additional binding step can be performed prior to gel electrophoresis to better separate the migration of the two complexes. In certain preferred embodiments, a third bis-biotinylated non-reactive component (NRC) is added to the mixture. Since only the complex lacking the protein of interest has any binding sites available, this third bis-biotinylated NRC will only bind to that complex. The NRC causes the complex lacking Protein 1 to migrate significantly differently than the complex comprising Protein 1, e.g., slower or faster. As a result, the electrophoresis will provide separation of the two complexes, and the complex comprising the protein of interest can be quantified to determine its quantity in the mixture. In alternative embodiments, rather than radically changing the migration of the complex lacking the protein of interest, the NRC can also be a quenching moiety that quenches the signal from the label, rendering the complexes lacking the protein of interest "invisible" to the subsequent detection and analysis. Quenching molecules are well known and readily accessible in the field to which the invention pertains.

In addition to the stoichiometry advantage, another benefit to using multi-biotin-tagged molecules is that the binding to streptavidin is tighter and more stable than that of mono-biotin-tagged molecules, i.e., more than two-fold greater stability. As such, where a high stability binding of two reactants to streptavidin is desired, using bis-biotin-tagged molecules is preferred. Alternatively, where increased stability is more important for a first one of the molecules and a single-biotin-based stability is sufficient for the second, using the tris-biotin tag (as described elsewhere herein) on the first molecule and a mono-biotin-tag on the second is preferred. Without wishing to be bound by theory, one likely reason for the increased stability is the avidity of the binding of a bis-biotin tag to a streptavidin tetramer. In proteins, avidity is the combined strength of multiple bond interactions. Avidity is the combined synergistic strength of bond affinities rather than the sum of bonds. As such, the dissociation of a single biotin moiety from a biotin-binding site on the streptavidin is rapidly followed by reassociation due to close proximity of the released biotin, which is effectively tethered to the streptavidin molecule by the biotin moiety that is still bound. As such, most of the time at least one biotin is bound, and if one is not bound it is very near and likely to rebind quickly. As long as both biotins don't dissociate simultaneously, the binding of the bis-biotin to the streptavidin is maintained.

In certain aspects, methods are provided for creating preparations comprising primarily streptavidin with only a single bis-biotinylated reactant bound and having two free biotin-binding sites. In preferred embodiments, separation of streptavidin complexes comprising a single bis-biotinylated reactant from complexes comprising two bis-biotinylated reactants is accomplished using ion-exchange column purification methods. For example, where the bis-biotinylated reactant is a negatively charged dye molecule, the charge on the dye facilitates preparation on the ion exchange column since complexes having two dyes bound will have a significantly more negative charge associated with them. A linear gradient of an acetonitrile-containing buffer is used to elute the complexes, and the fractions containing the streptavidin complex comprising a single bis-biotinylated reactant are pooled and concentrated. A detailed protocol is provided herein in the Examples section. The fractions that do not contain the desired complex can be saved and reused in future preparations, either directly (as in the case of the streptavidin complexes having no bis-biotinylated reactants bound) or after stripping off any remaining bis-biotinylated reactants.

In another aspect of the invention, kits are provided for labeling reactants using a tetrameric complex comprising a bis-biotinylated label. This invention also embraces kits which are useful for linking two individual reactants, which may be identical or different, via a tetrameric complex at a desired stoichiometry, preferably 1:1. In certain embodiments, such kits comprise streptavidin (or other tetrameric, biotin-binding complex) and a bis-biotinylated label, such as a mass label, spin label, or fluorescent dye. Alternatively, such kits comprise a bis-biotinylated label already bound to the tetrameric complex. Other constituents of the kits may comprise host cells suitable for cloning a biotinylation sequence into the gene of a protein of interest, and, preferably obtaining expression from the protein of interest; and a tetrameric complex coupled to a solid support; a biotinylation enzyme such as purified BirA. Instructions are also optionally included for various aspects of the methods, e.g., instructions for analysis and purification of the proteins expressed using these kits, purification of tetrameric complexes comprising a single, bis-biotinylated label, and analysis of quantities of proteins of interest in a cell lysate. Preferably, the host cells will express a biotinylating enzyme. Optionally, polynucleotides which, when transformed into host cells, cause the production or overproduction of biotinylating enzymes may be supplied in the kits, or the host cells provided with the kits may be already modified to produce or over-produce biotinylating enzymes. However, for some applications the absence of biotinylating enzyme in the host cell may be advantageous. For example, the kit user may prefer to biotinylate the expressed fusion proteins in vitro.

As noted above, bis-biotin coated surfaces can be employed for immobilization of a reactant or reactants of interest. Without limitation to any particular mechanism, the greater avidity of bis-biotin binding to streptavidin or another biotin-binding agent can improve loading of the reactant onto the surface and result in more stable association between the reactant and the surface. Accordingly, one aspect of the invention provides a solid support whose surface comprises multiple bis-biotin moieties. Each of the bis-biotin moieties includes two covalently linked biotin groups.

The bis-biotin moieties can be covalently or noncovalently associated with the surface, e.g., through association of a bis-biotin containing compound with the surface. For example, the bis-biotin moieties can be covalently coupled to the surface by coating the surface with a bis-biotin-PEG-silane, as described in greater detail below, or with another bis-biotin containing silane. In such examples, the bis-biotin moieties are covalently coupled to the surface through siloxane (Si—O—Si) bonds, and the surface is preferably a silica-based surface (for example, $SiO_2$, fused silica, glass, quartz, or the like). In such examples, each individual bis-biotin moiety is covalently attached to one of multiple copies of a group, which copies are covalently coupled to the surface. As another example, charged surfaces can be modified by adsorption of oppositely charged bis-biotin containing compounds. For example, negatively charged surfaces (including, e.g., silica-based surfaces) can be modified by adsorption of copolymers containing positive polyelectrolyte blocks and PEG-ylated (or similar anti-fouling) blocks. The polycationic blocks bind to regions of the surface that are electronegative, and the PEG components provide a nonreactive surface to preclude nonspecific binding. Exemplary polyelectrolyte-PEG copolymers include, e.g., PLL-PEG (poly(L-lysine)-poly(ethylene glycol)). The PEG groups, or a subset thereof, can include bis-biotin (bis-biotin-PLL-PEG). (For similar coatings including biotin, see, e.g., U.S. patent application publication 2002/0128234 "Multifunctional Polymeric Surface Coatings in Analytic and Sensor Devices" by Hubbell et al. and Huang et al. (2002) "Biotin-Derivatized Poly(L-lysine))-g-Poly(ethylene glycol): A Novel Polymeric Interface for Bioaffinity Sensing" Langmuir 18(1): 220-230.) Numerous other surface modification chemistries are known in the art and can be adapted to the practice of the present invention; for example, modification of a gold surface with a bis-biotin containing thiol compound. The bis-biotin moiety optionally includes at least one and, typically, two or at least two negatively charged groups, for example, sulfonic acid groups (e.g., methylsulfonic acid groups), carboxylic acid groups, sulfinic acid groups, phosphate groups, phosphinic acid groups, and/or phosphonic acid groups.

Suitable solid supports are known in the art and include, but are not limited to, beads, microspheres, pellets, disks, chips, wafers, microparticles, and planar surfaces comprising nanoscale wells, e.g., zero-mode waveguides (see, e.g., U.S. Pat. Nos. 7,056,661 and 7,315,019, previously incorporated herein by reference). The top surface of a substrate comprising zero-mode waveguides or other nanoscale wells, the sidewalls of the wells, and/or the bottom of the wells can comprise the bis-biotin moieties. In a preferred class of embodiments, the bis-biotin moieties are substantially only located on the bottom surface of the waveguides or wells (e.g., bis-biotin moieties are present on the bottom surface at a density that is 50 or more times greater, 100 or more times greater, or even 1000 or more times greater than the density of bis-biotin moieties on other surfaces of the substrate, such as the sidewalls of the wells or waveguides and the top surface of the substrate).

The supports are particularly useful for immobilization of reactants of interest, e.g., through binding of the bis-biotin moiety to streptavidin or the like, which is in turn bound to the reactant. Thus, a biotin-binding agent is optionally bound to the bis-biotin moieties on the surface, e.g., a tetravalent biotin-binding agent (e.g., streptavidin, tamavidin, NeutrAvidin, traptavidin, or the like). As detailed above, preferably both biotins in a bis-biotin moiety bind to the same molecule of the biotin-binding agent; multiple copies of the biotin-binding agent can bind to multiple different bis-biotin moieties on the surface, or a single copy of the biotin-binding agent can bind to a single bis-biotin moiety (e.g., located at the bottom of a nanoscale well). A molecule or molecular complex of interest can be bound to the biotin-binding agent. Typically, the molecule or complex is itself biotinylated, singly or multiply. For particularly stable binding, a bis-biotin tag is covalently coupled to the molecule or molecular complex of interest, and the bis-biotin tag is bound to a tetravalent biotin-binding agent that is in turn bound to one of the bis-biotin moieties on the surface. Again, preferably both biotins in the bis-biotin moiety bind to the same molecule of biotin-binding agent. Essentially any desired molecule or complex can be immobilized in this way, including, but not limited to, a biomolecule, a polypeptide, a protein, an enzyme (e.g., a polymerase), a polymerase/template/primer complex, a nucleic acid (e.g., an oligonucleotide, DNA, RNA, DNA/RNA hybrid, nucleic acid derivative, etc.), a cofactor, a small molecule (e.g., a drug), a non-reactive component, or a label. Nanoparticles or other reactants of interest can also be immobilized in this manner. In one class of embodiments, the bis-biotin moieties are free (i.e., not bound; available for binding, e.g., to a biotin-binding agent).

The density of biotin moieties on the surface is optionally varied. For some applications, a high density of biotin moieties (and therefore of bis-biotin moieties) on the surface is desirable. For other applications, a lower density of biotin moieties (and therefore of bis-biotin moieties) on the surface is desirable. For example, a lower biotin density can facilitate maximization of the number of zero-mode waveguides in an array that are singly loaded with a molecule or complex of interest (e.g., a polymerase-template complex). Where biotin is provided for immobilization of molecules or complexes of interest, e.g., at the base of nanoscale wells, controlling the density or number of biotin moieties on the surface can assist in attaining the desired occupancy. For example, density or number of biotin moieties on the surface can be adjusted such that enough biotin is available to readily bind to the first molecule of interest to encounter the base of a nanoscale well, but such that occupancy of the well by that first molecule is sufficient to occlude accessibility of biotin in that well by other molecules. In one embodiment, there is one bis-biotin moiety at the base of a nanoscale well. In some embodiments, the density or number of bis-biotin moieties will be some fraction of the maximum possible density or number of bis-biotin moieties on the surface in a nanoscale well. Thus, in some embodiments, the density of biotin moieties on the surface (e.g., on the bottom surface of zero-mode waveguides or other nanoscale wells) is $5 \times 10^{-3}$ biotins/nm$^2$ or less, e.g., $2.6 \times 10^{-3}$ biotins/nm$^2$ or less, preferably $1.3 \times 10^{-3}$ biotins/nm$^2$ or less, $6.5 \times 10^{-4}$ biotins/nm$^2$ or less, $3.3 \times 10^{-4}$ biotins/nm$^2$ or less, or $1.6 \times 10^{-4}$ biotins/nm$^2$ or less. Accordingly, in such embodiments, the density of bis-biotin moieties on the surface (e.g., on the bottom surface of zero-mode waveguides or other nanoscale wells) is $2.5 \times 10^{-3}$ bis-biotins/nm$^2$ or less, e.g., $1.3 \times 10^{-3}$ bis-biotins/nm$^2$ or less, preferably $6.5 \times 10^{-4}$ bis-biotins/nm$^2$ or less, $3.25 \times 10^{-4}$ bis-biotins/nm$^2$ or less, $1.65 \times 10^{-4}$ bis-biotins/nm$^2$ or less, or $8 \times 10^{-5}$ bis-biotins/nm$^2$ or less. For discussion of various techniques for achieving single loading, see, e.g., U.S. Pat. No. 8,906,831 and U.S. patent application Ser. No. 15/078,915 filed Mar. 23, 2016, each of which is hereby incorporated by reference in its entirety.

Another aspect of the invention provides compounds comprising bis-biotin moieties, including compositions useful for modifying surfaces to present bis-biotin moieties and compounds useful for producing such compositions. A variety of additional applications for the bis-biotin containing compounds are described herein. For example, a bis-biotin compound can be employed in production of a nucleotide analog, e.g., a labeled nucleotide analog, by reacting the compound with a nucleotide component and/or with a dye component (preferably a fluorescent dye) and binding the bis-biotin(s) to a tetravalent biotin-binding agent, as described hereinbelow and in greater detail in U.S. Pat. No. 9,062,091, U.S. patent application Ser. No. 15/357,958 filed Nov. 21, 2016, U.S. patent application Ser. No. 15/357,965 filed Nov. 21, 2016, and U.S. patent application Ser. No. 15/357,966 filed Nov. 21, 2016, each of which is hereby incorporated by reference in its entirety.

One general class of embodiments provides a compound having the formula

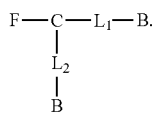

B is a biotin group. The biotin group is conveniently attached as a biotinamide, though other linkages can also be employed, e.g., an ester linkage or other linkages formed through a nucleophilic substitution of a nucleophile with the activated carboxylic acid group of biotin. $L_1$ and $L_2$ are linking groups, which can but need not be identical. $L_1$ and/or $L_2$ can comprise a negatively charged and/or a positively charged substituent or can be uncharged. In one exemplary class of embodiments, $L_1$ and/or $L_2$ comprise a negatively charged substituent, preferably at a position other than alpha to any biotinamide. For example, $L_1$ and/or $L_2$ can include a sulfonic acid group (e.g., a methylsulfonic acid group), a carboxylic acid group, a sulfinic acid group, a phosphate group, a phosphinic acid group, and/or a phosphonic acid group. $L_1$ and/or $L_2$ optionally include two or more charged substituents. For example, $L_1$ and/or $L_2$ can each comprise three sulfonic acid moieties. In one exemplary class of embodiments, $L_1$ and/or $L_2$ comprise a 3,4,5-tris(3-sulfopropoxy)benzoic acid group. Without limitation to any particular mechanism, inclusion of negatively charged groups in the bis-biotin moiety can increase solubility of the compound and/or increase interaction of the bis-biotin moiety with a biotin-binding agent such as streptavidin. As noted, the biotin moiety is conveniently attached to the linker through an amide linkage; the linking groups themselves are optionally also assembled through reaction to form an amide bond, e.g., between cysteic acid (which contributes a negatively charged group) or another amino acid and an amino carboxylic acid (e.g., a branched or linear alkyl amino carboxylic acid, e.g., having from 1-20 carbons, e.g., ω amino caprylic acid). In other embodiments, the linking group is incorporated as a single unit, e.g., an alkyl, ester, ether, amide, etc. group. A linking group optionally comprises or consists of an amino acid residue, e.g., a substituted amino acid residue, e.g., an amino acid residue with charged species substitution groups. Generally, a linking group includes a series of stable covalent bonds incorporating at least one (and typically 2-60, e.g., 2-40, e.g., 10-30) nonhydrogen atoms (e.g., C, N, O, S and/or P). The linking groups covalently attach the biotin moieties to the core group.

F is a reactive functional group. Reactive functional groups are optionally used to attach the compound to a surface, to a moiety that is (or will be) in turn attached to a surface, or to produce another bis-biotin containing compound. Useful reactive functional groups include, for example: carboxyl groups and derivatives thereof, including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides; amine groups, which can be, for example, acylated, alkylated or oxidized; hydroxyl groups, which can be converted to esters, sulfonates, phosphoramidates, ethers, aldehydes, etc.; haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom; dienophile groups, which are capable of participating in Diels-Alder reactions such as, for example, maleimido groups; aldehyde or ketone groups, allowing derivatization via formation of carbonyl derivatives, e.g., imines, hydrazones, semicarbazones or oximes, or via such mechanisms as Grignard addition or alkyllithium addition; sulfonyl halide groups for reaction with amines, for example, to form sulfonamides;

sulfhydryl or thiol groups, which can be converted to disulfides or reacted with acyl halides, for example; alkenes, which can undergo, for example, cycloadditions, acylation, Michael addition, etc.; epoxides, which can react with, for example, amines and hydroxyl compounds; and azides, alkynes, or other groups useful for click reactions. The reactive functional group can be chosen such that it does not participate in, or interfere with, the reactions necessary to assemble or utilize the compound. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., *Protective Groups in Organic Synthesis*, John Wiley & Sons, New York, 1991.

C is a core group, a multifunctional core with multiple linking sites. The core group is at least trifunctional, having at least three linking sites, one covalently attached to the functional group and two covalently attached to the biotin groups via the linking groups. Suitable multifunctional groups are known in the art and include, but are not limited to, a six-membered ring, e.g., a tri-substituted six-membered ring, e.g., a tri-substituted cyclohexane or a tri-substituted six-membered aromatic ring such as, e.g., a benzene or triazine. The aromatic core can be heterocyclic, containing, for example, one nitrogen (pyridine), two nitrogens (diazine), or preferably three nitrogens (triazine). The heterocyclic aromatic core can also comprise, e.g., silicon, germanium, tin, phosphorous, or arsenic. The aromatic core is preferably substituted at the 1, 3, and 5 positions (or the 2, 4, and 6 positions). These substitution patterns result in the substituents radiating from the aromatic ring in a plane at an angle of 120 degrees from one another. Examples of structures based on triazines (e.g., substituted piperidine-substituted triazines) that can be used as core groups are shown in FIG. 1 of U.S. patent application publication 2015/0307933, which is incorporated herein by reference in its entirety for all purposes. A cyclohexane core group is similarly preferably substituted at the 1, 3, and 5 positions (or the 2, 4, and 6 positions), e.g., all-cis. Additional exemplary groups that can be adapted for use as core groups are shown in FIGS. 2-4 and 6 of U.S. patent application publication 2015/0307933; unneeded linking sites are optionally blocked, hydrogenated, or the like. Suitable core groups include, but are not limited to, 1,1',1"-(1,3,5-triazine-2,4,6-triyl)tris(piperidin-4-amine) (T1)

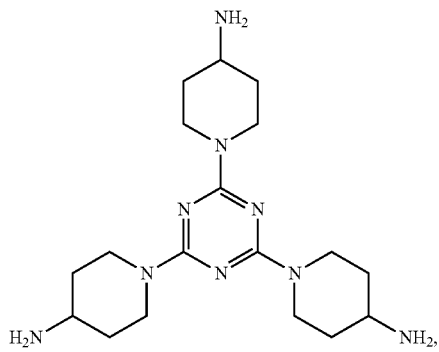 [SMILES: NC1CCN(c2nc(N3CCC(N)CC3)nc(N3CCC(N)CC3)n2)CC1]

1-(4,6-bis(4-aminopiperidin-1-yl)-1,3,5-triazin-2-yl)piperidine-4-carboxylic acid (T2)

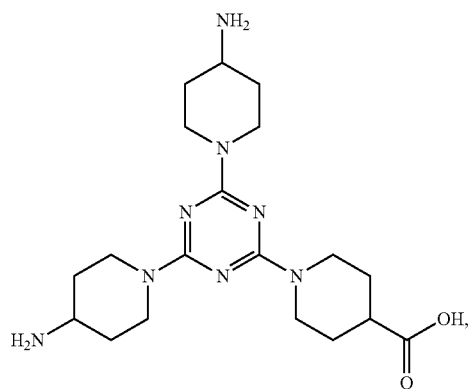 [SMILES: NC1CCN(c2nc(N3CCC(N)CC3)nc(N3CCC(C(=O)O)CC3)n2)CC1]

cyclohexane-1,3,5-triamine

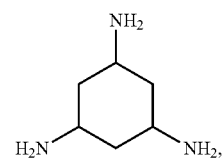

cyclohexane-1,3,5-tricarboxylic acid

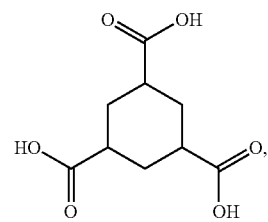 [SMILES: O=C(O)C1CC(C(=O)O)CC(C(=O)O)C1]

tris(2-aminoethyl)amine

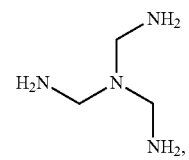

and
(bis-carboxymethyl-amino)-acetic acid

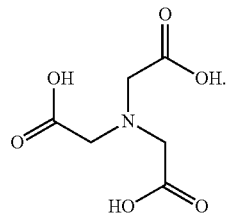 [SMILES: O=C(O)CN(CC(=O)O)CC(=O)O]

Figure 14:
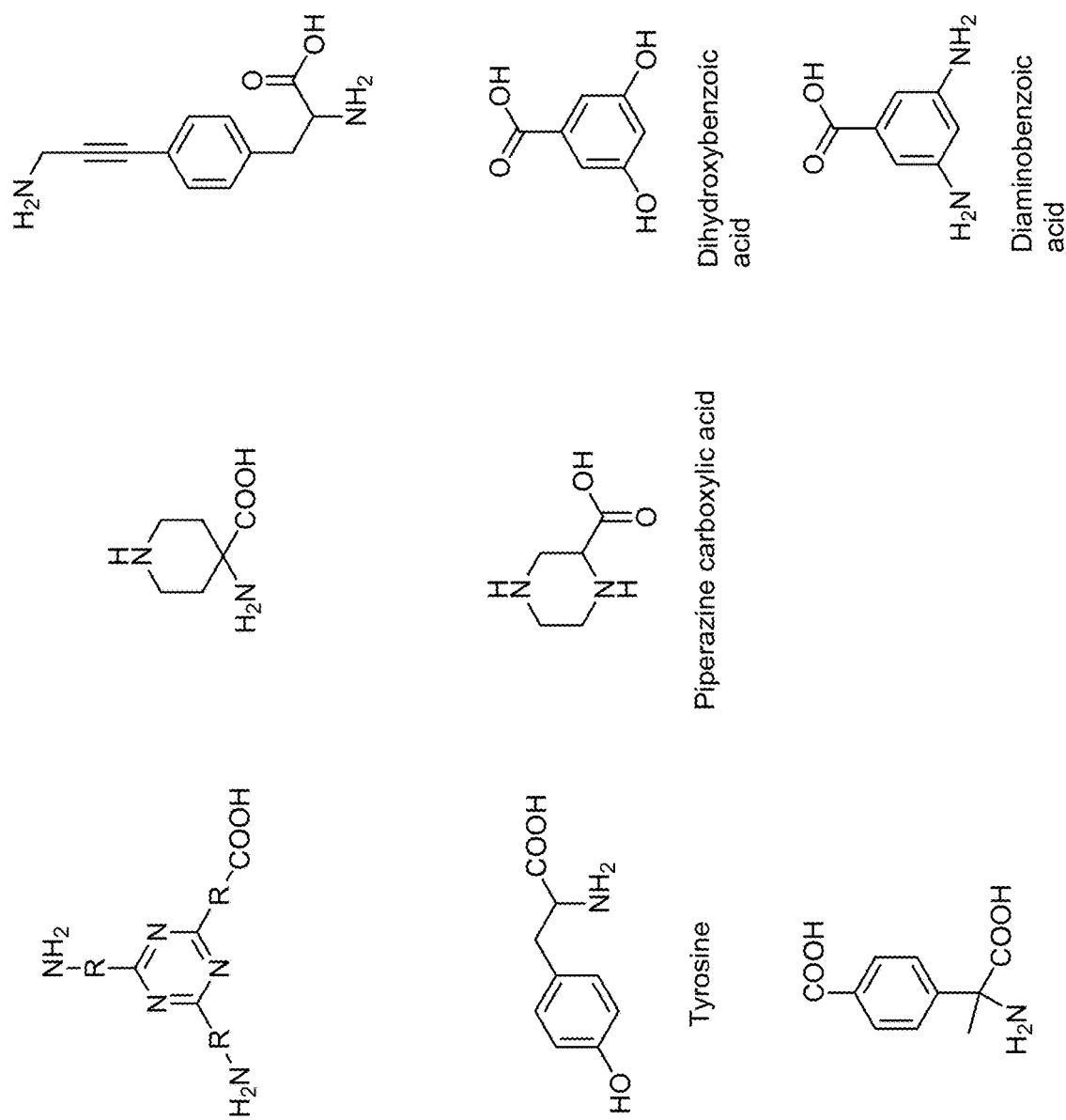
FIG. 14 depicts exemplary rigid tridentate groups that can be employed in synthesis of bis-biotin compounds.
Figure 15:
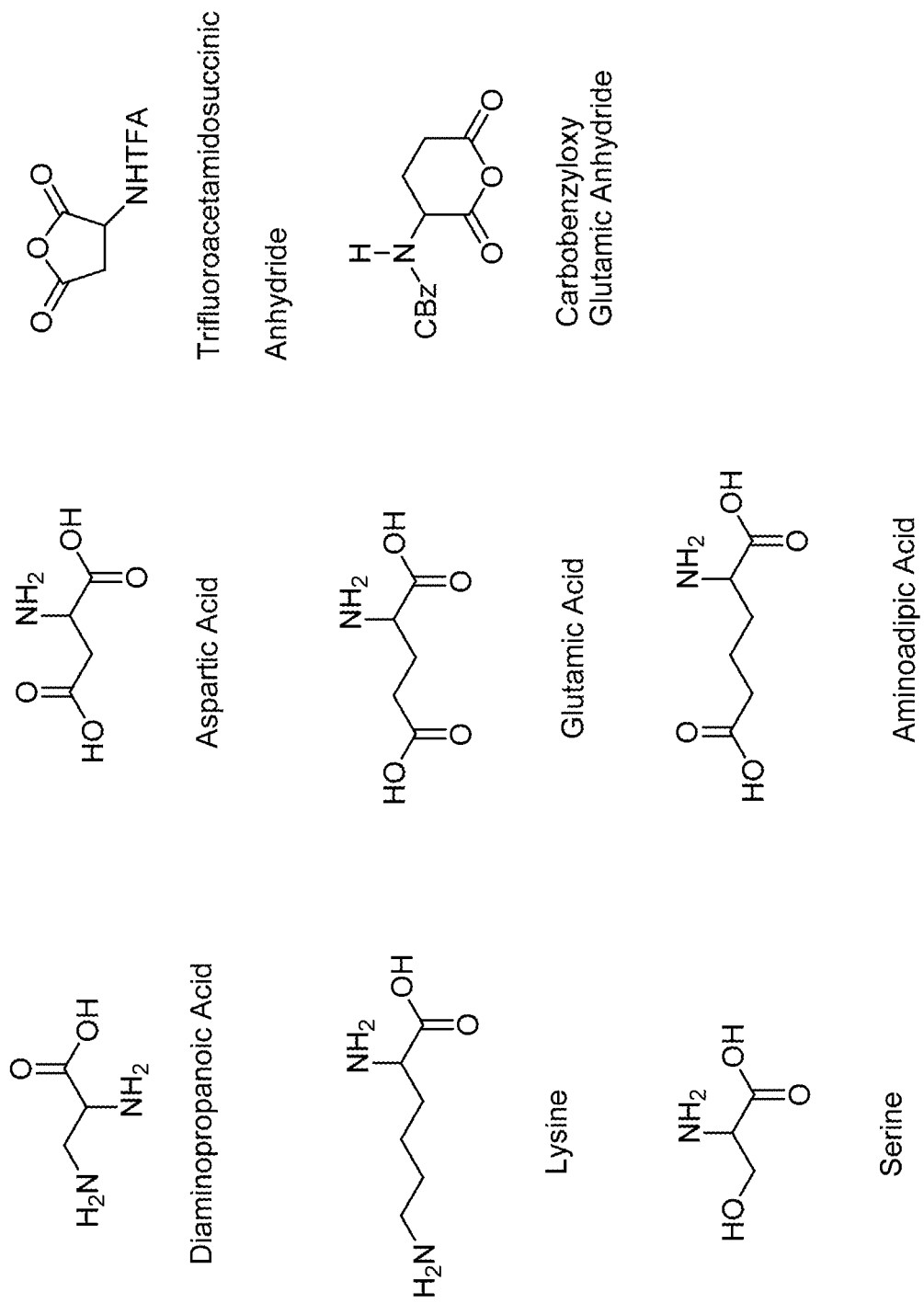
FIG. 15 depicts exemplary flexible tridentate groups that can be employed in synthesis of bis-biotin compounds.

Additional exemplary core groups include, but are not limited to, cyanuric chloride, mesalamine, diaminopropanoic acid, aspartic acid, cysteine, glutamic acid, pyroglutamic acid, S-acetylmercaptosuccinic anhydride, carbobenzoxylysine, histidine, lysine, serine, homoserine, tyrosine, piperidinyl-1,1-amino carboxylic acid, and diaminobenzoic acid, as well as the rigid tridentate linkers shown in FIG. 14 and the flexible tridentate linkers shown in FIG. 15. Amine, ester, amide, or like groups can optionally be used to connect the core structure to other portions of the compound.

Exemplary compounds, e.g., useful for synthesizing bis-biotin-PEG-silanes, synthesizing bis-biotin-PLL-PEG, reacting with functional groups disposed on a surface, reacting with a nucleotide and/or dye component for production of nucleotide analogs, or the like as detailed herein or as evident to one of skill include

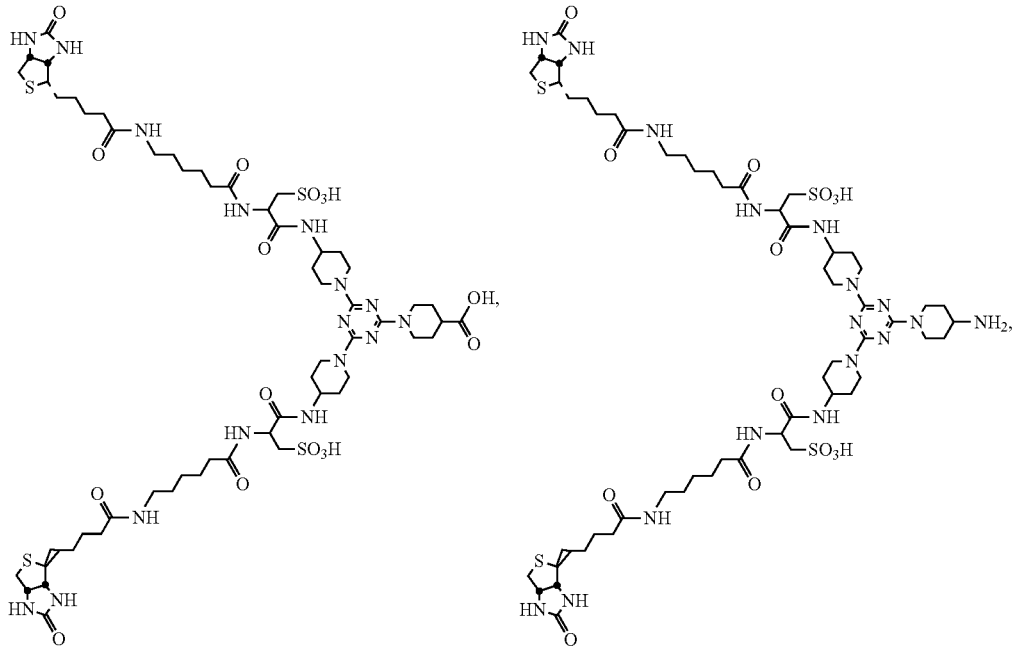

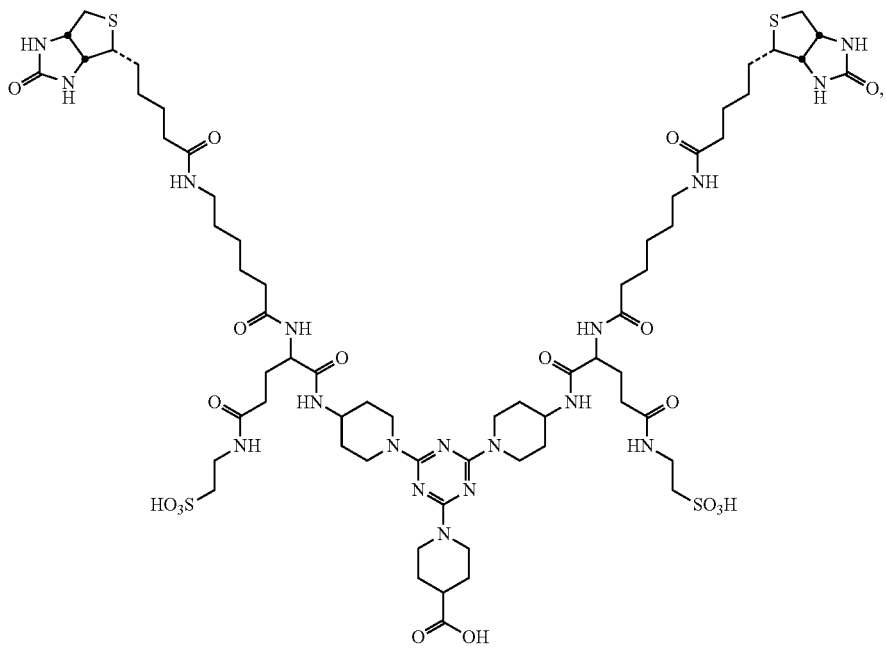

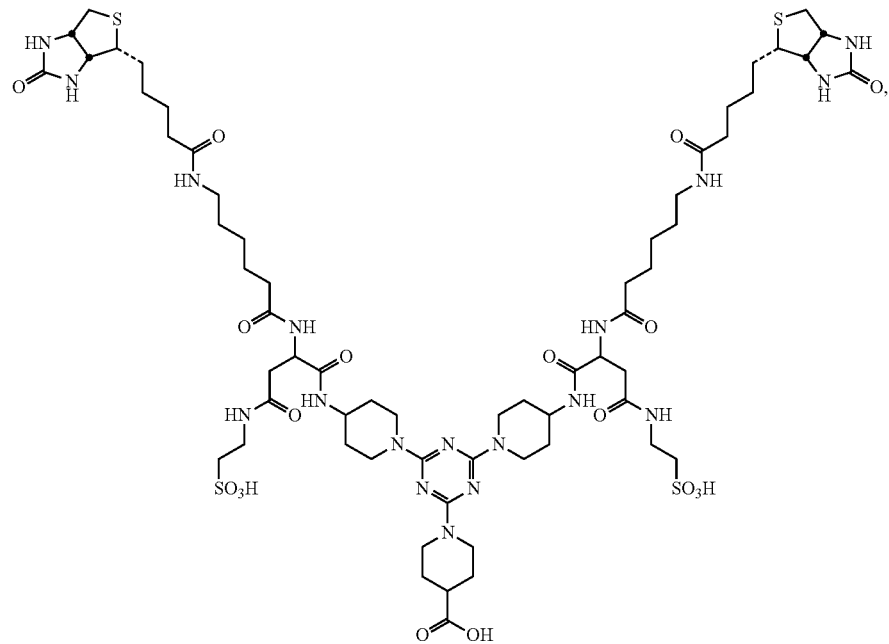
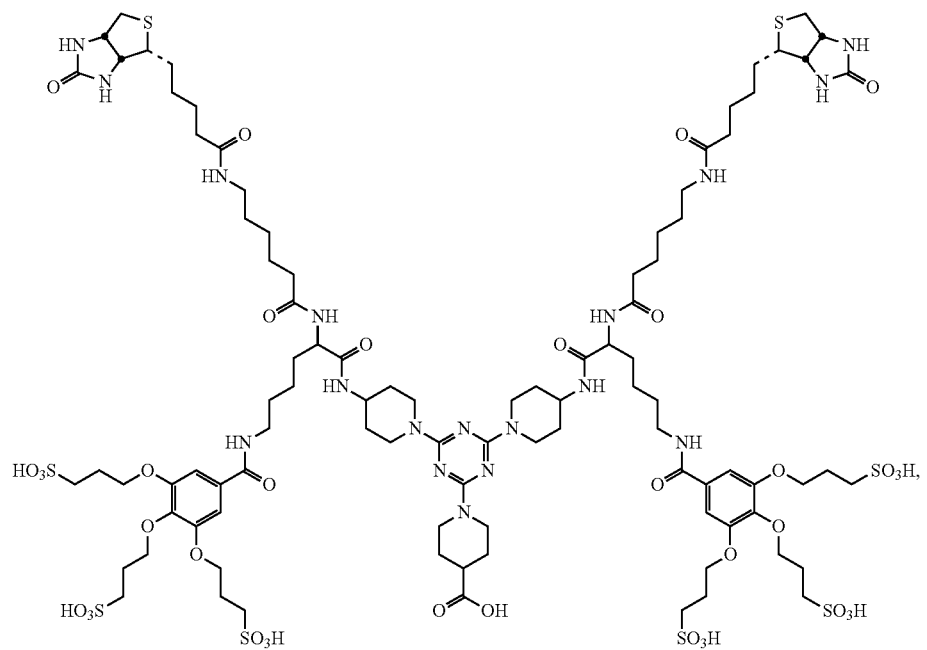

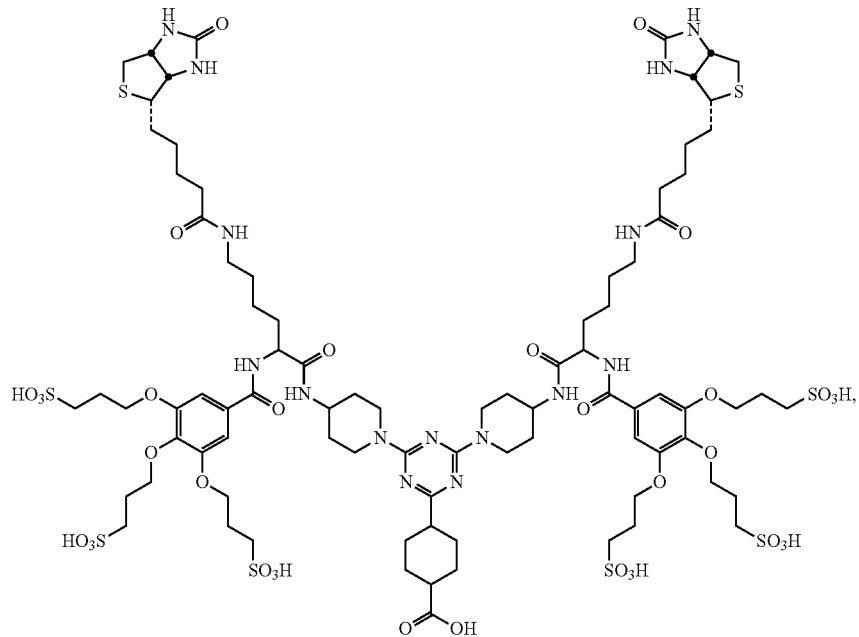
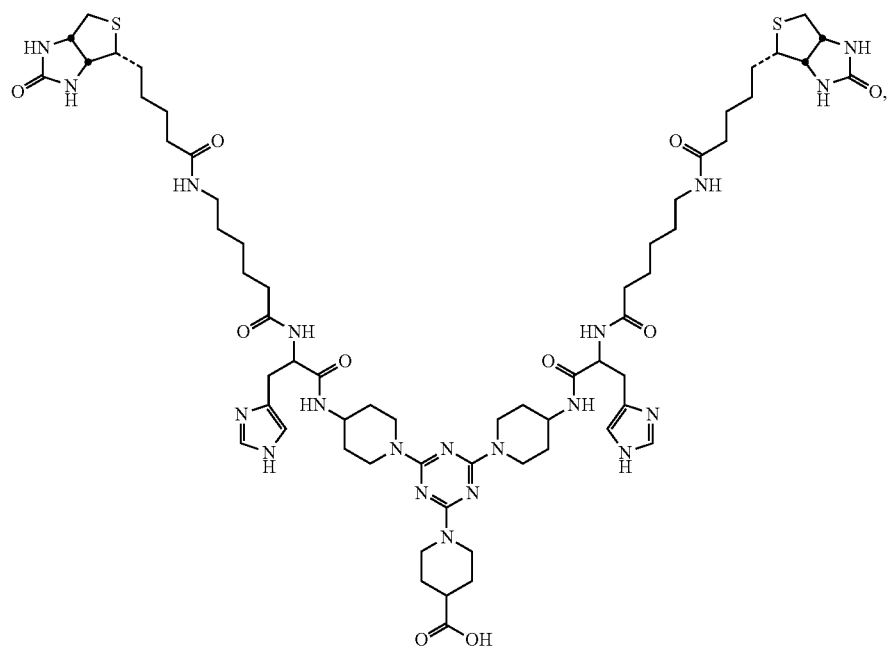

33
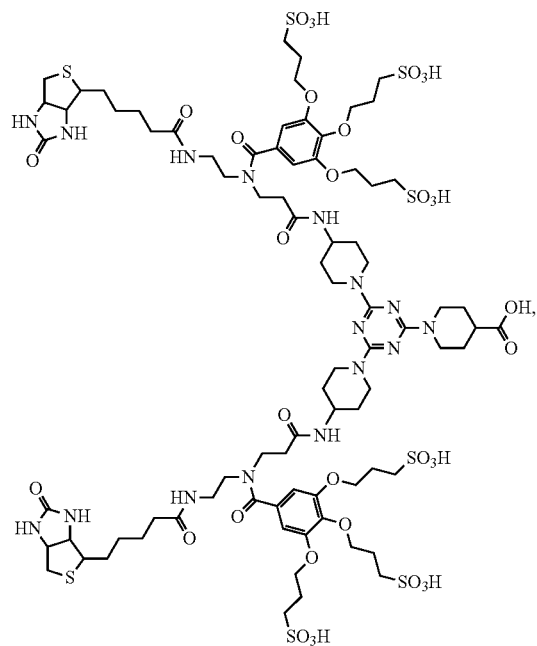
34
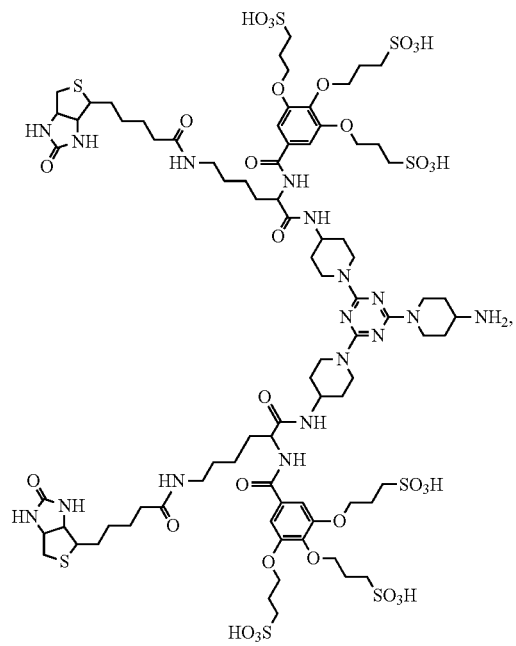
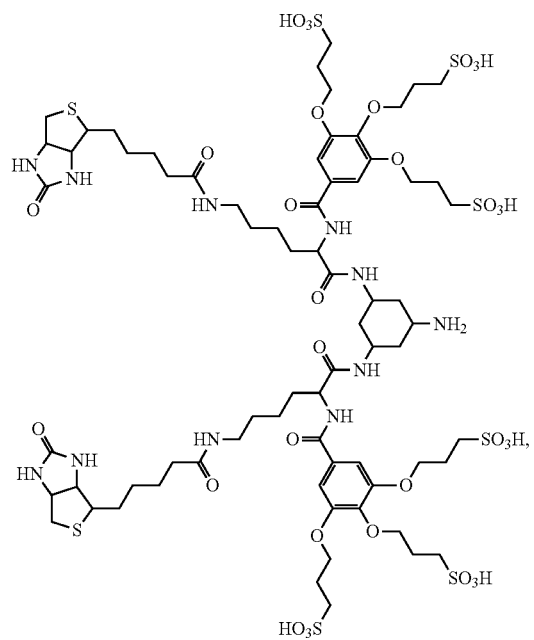

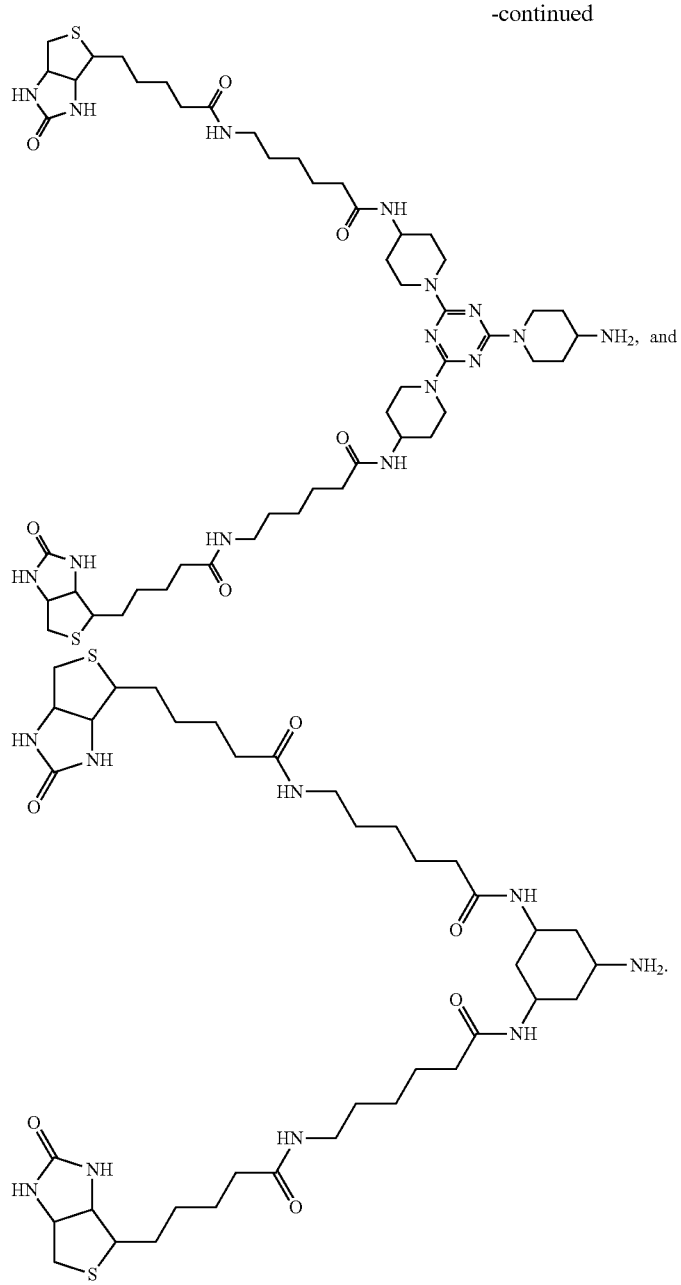

Another aspect of the invention provides bis-biotin-PEG-silanes. These compounds have the formula

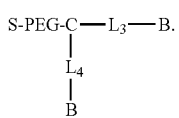

B is a biotin group. $L_3$ is a direct bond or a first linking group, and $L_4$ is a direct bond or a second linking group. $L_3$ and $L_4$ can but need not be identical. C is a core group. Exemplary suitable core and linking groups have been described above. PEG represents a moiety that comprises a polyethylene glycol group. The PEG group typically includes 2-250 ethylene oxide units (inclusive), e.g., 8-250, 8-230, or 50-100. The PEG unit is typically linear but can be branched or otherwise nonlinear (e.g., star or comb). It will be evident that the moiety that includes the PEG group optionally also includes one or more additional atoms (e.g., non-hydrogen atoms) at one or both of its termini, e.g., for ease of covalent connection to the silane and core moieties. S comprises a silane moiety. A "silane group" ("silane moiety") comprises a tetrahedral Si atom. Silane groups of particular interest in the context of the present invention include groups of the form $-SiX_3$, where X is Cl, $NH_2$, OH, or OR (where R is an alkyl group or hydrocarbon group, e.g., a methyl or ethyl group). Optionally, the silane group is a trimethoxysilane or triethoxysilane group. It will be evident that S optionally also includes one or more additional atoms (e.g., non-hydrogen atoms), e.g., for ease of covalent connection to the PEG moiety.

In one exemplary class of embodiments, the compound has the formula
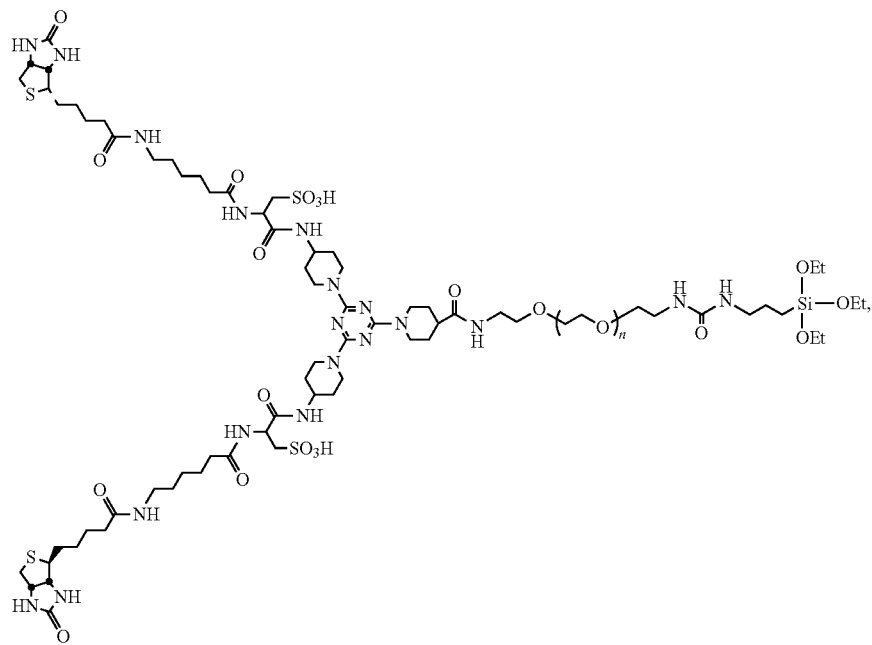
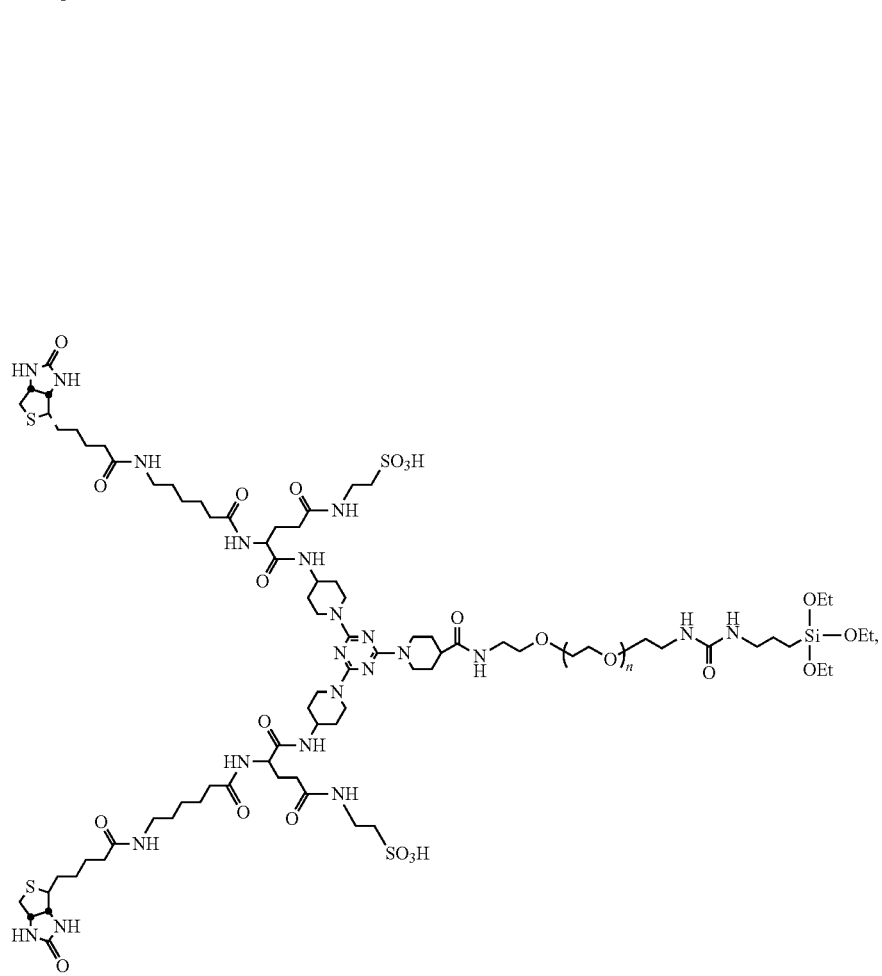

-continued
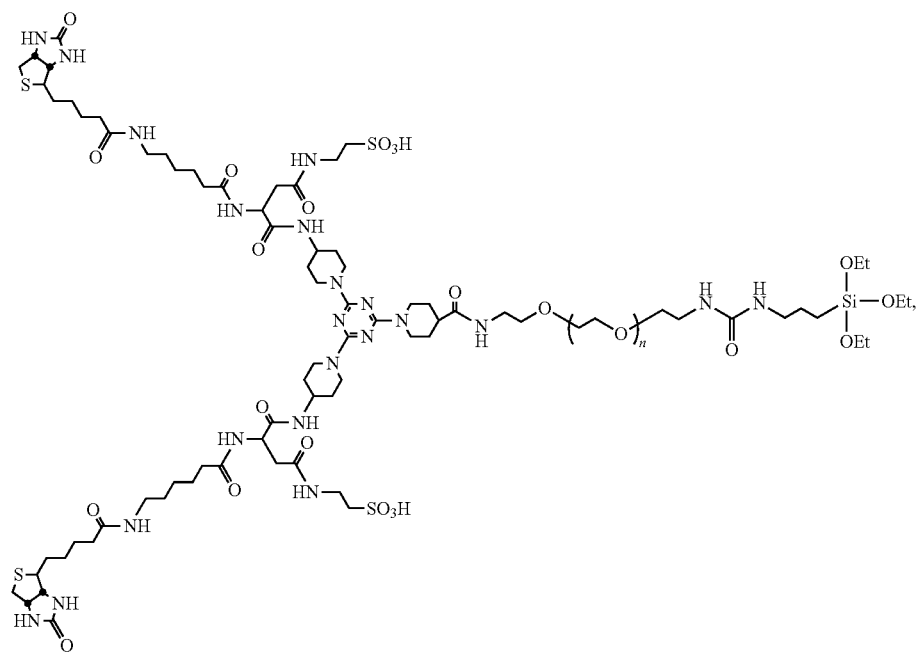
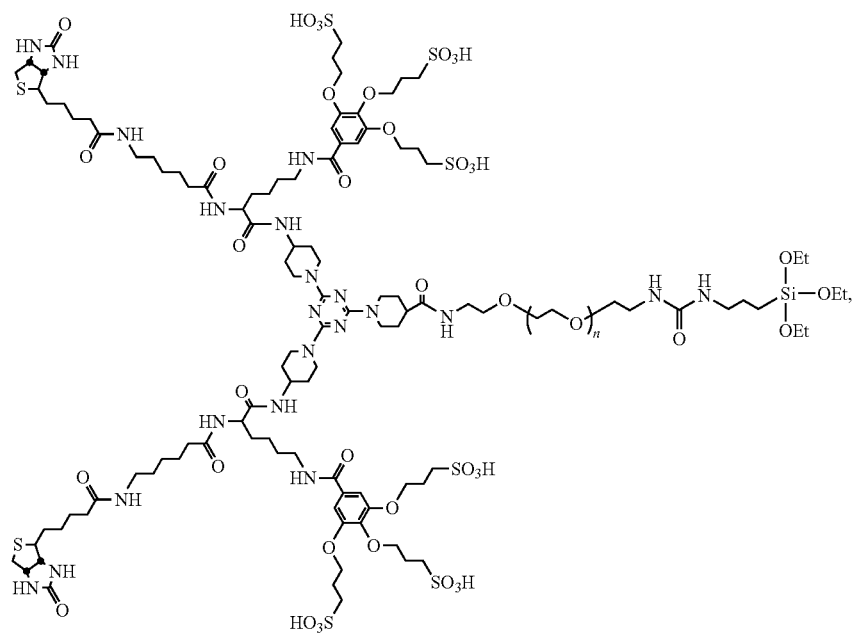

-continued

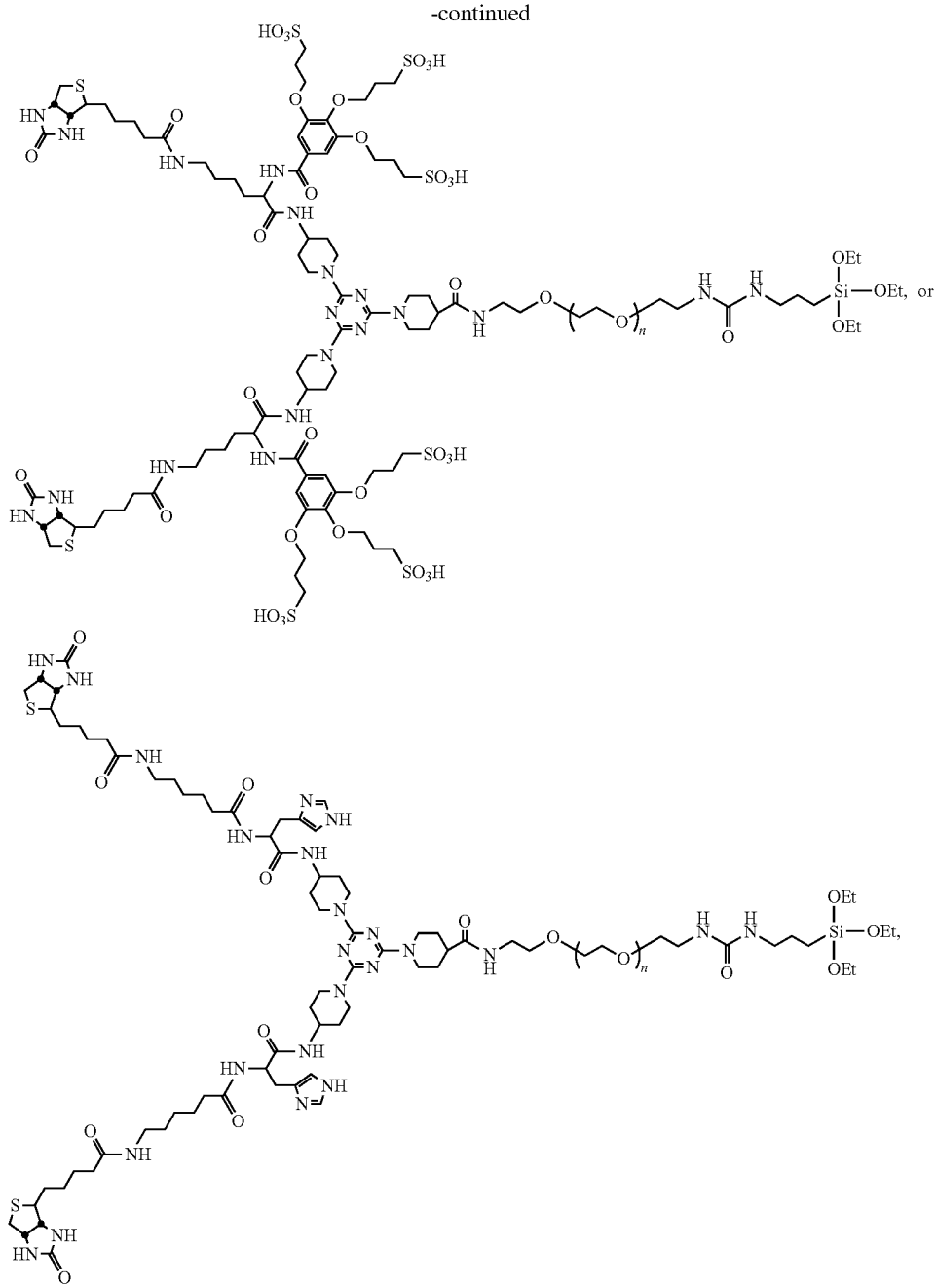

where n is between 2 and 250 (e.g., between 7 and 250, between 7 and 230, or between 50 and 100). Optionally, n=77.

In yet another aspect, the invention provides methods for preparing bis-biotin coated surfaces. In the methods, a surface is coated with a compound that comprises a bis-biotin moiety, each bis-biotin moiety having two covalently linked biotin moieties. To coat the surface, the surface is contacted with the compound, using essentially any convenient technique known in the art (e.g., dipping, spraying, pipetting, painting, printing, wet-coating, flowing, vapor deposition, spin coating, etc.), and the bis-biotin moiety becomes stably associated with the surface. The compound (and thus the bis-biotin) can be noncovalently associated with the surface. In other embodiments, the bis-biotin moiety is covalently coupled to the surface, e.g., through reaction of the compound with the surface (or with another compound that is in turn covalently coupled to the surface, directly or indirectly).

The surface can be the entire surface or a portion thereof of a solid support, for example, a bead, microsphere, pellet, disk, chip, wafer, microparticle, or planar surface comprising nanoscale wells, e.g., zero-mode waveguides (see, e.g., U.S. Pat. Nos. 7,056,661 and 7,315,019, previously incorporated herein by reference). The top surface of a substrate comprising zero-mode waveguides or other nanoscale wells, the sidewalls of the wells, and/or the bottom of the wells can be coated with the compound. In a preferred class of embodiments, substantially only the bottom surface of the waveguide or well is coated with the compound, typically, the bottom surface of each of multiple (e.g., hundreds, thousands, or even a million or more) waveguides or nanoscale wells that are disposed in a substrate (for example, bis-biotin moieties can be present on the bottom surface at a density that is 50 or more times greater, 100 or more times greater, or even 1000 or more times greater than the density of bis-biotin moieties on other surfaces of the substrate, such as the sidewalls of the wells or waveguides and the top surface of the substrate).

Exemplary surface materials and compounds have been described above. In one class of embodiments, the compound comprises a silane, e.g., a bis-biotin-PEG-silane. In such embodiments, the surface is preferably a silica-based surface (for example, $SiO_2$, fused silica, glass, quartz, or the like). The bis-biotin moiety optionally includes at least one and, typically, two or at least two negatively charged groups, for example, sulfonic acid groups (e.g., methylsulfonic acid groups), carboxylic acid groups, sulfinic acid groups, phosphate groups, phosphinic acid groups, and/or phosphonic acid groups. Without limitation to any particular mechanism, inclusion of negatively charged groups in the bis-biotin moiety can increase solubility of the compound and/or increase interaction of the bis-biotin moiety with a biotin-binding agent such as streptavidin.

The methods are particularly useful for preparing surfaces for immobilization of reactants of interest, e.g., through binding of the bis-biotin moiety to streptavidin or the like, which is in turn bound to the reactant. Thus, the methods optionally include binding a biotin-binding agent to the bis-biotin moieties on the surface, e.g., a tetravalent biotin-binding agent (e.g., streptavidin, tamavidin, NeutrAvidin, traptavidin, or the like). As detailed above, preferably both biotins in a bis-biotin moiety bind to the same molecule of the biotin-binding agent; multiple copies of the biotin-binding agent can bind to multiple different bis-biotin moieties on the surface, or a single copy of the biotin-binding agent can bind to a single bis-biotin moiety (e.g., located at the bottom of a nanoscale well). The methods can also include binding a molecule or molecular complex of interest to the biotin-binding agent. Binding the molecule or molecular complex of interest to the tetravalent biotin-binding agent can be performed before, after, or simultaneously with binding of the tetravalent biotin-binding agent to the bis-biotin moiety on the surface. Typically, the molecule or complex is itself biotinylated, singly or multiply. For particularly stable binding, a bis-biotin tag is covalently coupled to the molecule or molecular complex of interest, and the bis-biotin tag is bound to a tetravalent biotin-binding agent that is in turn bound to one of the bis-biotin moieties on the surface. Again, preferably both biotins in the bis-biotin moiety bind to the same molecule of biotin-binding agent. Essentially any desired molecule or complex can be immobilized in this way, including, but not limited to, a biomolecule, a polypeptide, a protein, an enzyme (e.g., a polymerase), a polymerase/template/primer complex, a nucleic acid (e.g., an oligonucleotide, DNA, RNA, DNA/RNA hybrid, nucleic acid derivative, etc.), a cofactor, a small molecule (e.g., a drug), a non-reactive component, or a label. Nanoparticles or other reactants of interest can also be immobilized in this manner.

For additional information on modification of surfaces, including selective modification of the bottom of nanoscale wells, see, e.g., U.S. Pat. Nos. 8,193,123 and 8,501,406 and Korlach et al. (2008) "Selective aluminum passivation for targeted immobilization of single DNA polymerase molecules in zero-mode waveguide nanostructures" PNAS 105 (4):1176-1181, which are incorporated by reference in their entireties for all purposes.

III. Applications

Various applications of the methods and compositions have been described in the embodiments set forth above. For example, the tetrameric complexes comprising a bis-biotinylated label (e.g., fluorescent dye) are very effective labeling reagents for bis-biotinylated reactants of interest. The methods teach how to purify the label-tetramer complexes from doubly-labeled complexes. The purified complexes efficiently bind to the bis-biotinylated reactant of interest, and the resulting complex effectively links the label to the reactant in a highly stable complex.

Also described at length above, colocalization of two reactants (two of the same reactant or two different reactants) is also a highly beneficial application of the invention. The compositions provided herein can provide colocalization of different proteins, such as enzymes that work cooperatively. This can function to provide "pseudo-fusion proteins" that behave similar to traditional fusion proteins, but which can be assembled much more quickly without the need to clone two proteins together. Examples of such enzyme include, but are not limited to, polymerases and nucleic-acid-modifying enzyme (e.g., repair enzymes, topoisomerases, methyltransferases, etc.). Other reactants that are beneficially colocalized are those that participate in the same metabolic pathway, e.g., synthetic biochemical pathways. Yet further, some reactions benefit by having higher local concentrations of components having protective functions, e.g., those that reduce damage to reaction components under excitation illumination. In other embodiments, reactants are colocalized to enhance reaction kinetics between them, e.g., enzymes acting on enzyme substrates, and this can provide a consolidation and/or acceleration of an enzymatic pathway. Binding interactions also benefit by colocalization of binding partners, e.g., antibody-antigen pairs, receptor-ligand pairs, etc. The methods and compositions herein can also be used to enhance the activity of stimuli-responsive polymers used to gate biomolecular reactions by ensuring their colocalization with the active site of proteins with which they interact, e.g., as described in Shimoboji, et al. (2001) Bioconjugate Chem. 12:314-319, which is incorporated herein by reference in its entirety for all purposes.

The compositions can also be used to enrich a nucleic acid mixture for specific sequences of interest by using a bis-biotinylated oligonucleotide (e.g., a probe or primer) to "fish" for the specific sequences in the mixture. The oligonucleotide is designed to be complementary to the sequence or sequences of interest in a nucleic acid mixture. Preferably, the nucleic acid mixture is fragmented prior to exposure to the bis-biotinylated oligonucleotide. In especially preferred embodiments, the fragmentation is specific to ensure that a contiguous sequence in the desired nucleic acid is complementary to the oligonucleotide. In some embodiments, the fragmentation provides a 3' end that is complementary to a portion of the oligonucleotide near or at the 5' end. After exposing the fragmented nucleic acid mixture to the bis-biotinylated oligonucleotide under conditions that promote annealing, a polymerase enzyme is used to extend the oligonucleotide, thereby strengthening the interaction between the oligonucleotide (now extended) and the sample nucleic acid of interest. Immobilization of the extended oligonucleotide/sample nucleic acid allows the other nucleic acids in the mixture to be removed, thereby isolating the sequence(s) of interest and providing mixture enriched for those sequences. Following removal of the non-specific sequences, the remaining nucleic acids can be further analyzed. For example, the duplex between the extended oligonucleotide and sample nucleic acid can be removed from the bis-biotin moiety and subjected to a sequence reaction, amplified, and/or cloned. Alternatively, only one of the extended oligonucleotide or the selected sample nucleic acid is subjected to further analysis, e.g., single-strand sequencing, amplification, etc. In related embodiments, other types of affinity pairs can be used. For example, in certain embodiments, the oligonucleotide comprises two streptavidin-binding aptamers rather than a bis-biotin moiety, e.g., as described elsewhere herein. Like the bis-biotin moiety, the two aptamers are used to immobilize and isolate the sample nucleic acid of interest, optionally after extension of the oligonucleotide.

In certain aspects, the invention provides methods for detecting protein-protein interactions between two biotinylated (preferably bis-biotinylated) proteins using streptavidin molecules having nucleic acid tags or "barcodes." In a preferred embodiment, a first bis-biotinylated protein is bound to a first tag-labeled streptavidin molecule, and a second bis-biotinylated protein is bound to a second tag-labeled streptavidin molecule. The two proteins, now linked to the tagged streptavidin molecules, are combined in a reaction mixture that promotes an interaction between them, e.g., covalent or noncovalent binding, catalytic interactions, or other interaction that causes their permanent or transient colocalization. The reaction mixture also comprises a ligase and promotes ligation of the free ends of the two tags when the proteins are bound to the streptavidin. An illustrative embodiment is provided in FIG. 7, in which Protein 1 and Protein 2 are each bound via a bis-biotin linkage to a different streptavidin. The streptavidin bound to Protein 1 comprises a nucleic acid tag, Tag 1; and the streptavidin bound to Protein 2 comprises a nucleic acid tag, Tag 2. Interaction of these proteins causes localization of the tags, which are ligated together at the ends. Subsequent cleavage of the tags at cleavage sites (each indicated by an asterisk) releases them from the bis-biotin tags, and the ligated tags can be further manipulated, e.g., by amplification, circularization, sequencing, gel-based analysis, etc.

Detection of a ligation event serves as a proxy for the interaction between the two proteins. For example, where each of the tags has a different primer binding site at an end distal to the end of the tag at which ligation occurs, the tags, ligated together, are a template for exponential amplification, e.g., by PCR; tags that are not ligated cannot be exponentially amplified since they have only one primer site. The product of amplification can be detected by gel-based methods, or can be subjected to a nucleic acid sequencing reaction. Determining the actual sequence rather than just the size of the amplification product is preferred since it allows the practitioner to combine multiple different proteins with multiple different tags, and the sequence of the amplified product is used to identify which of the multiple proteins bound to each other. In some embodiments, the nucleic acid tags are single-stranded and the ligation is facilitated by using a "splint" oligo complementary to the ends of the tags, where binding of the oligo to the tags brings the ends of the tags into position for efficient ligation. In other embodiments, the nucleic acid tags are double-stranded and the ligation is facilitated by complementary overhangs of the tags. In certain embodiments, the ligated tags are released from the proteins, e.g., by endonuclease digestion, and circularized prior to further analysis. For a single-stranded construct formed by ligating two single-stranded tags, the circularization is accomplished in various ways, e.g., by ligation of the cut ends, e.g., using a splint oligo as described above; or by synthesizing a complementary strand and attaching stem-loop adaptors to the double-stranded ends produced. Similarly, for double-stranded construct formed by ligating two double-stranded tags, the double-stranded termini formed by the endonuclease reaction can be directly ligated together to form a double-stranded circular construct, or can be ligated to stem-loop adaptors to form a single-stranded circular construct. The tags on different protein can also differ by more than their canonical base sequence. For example, in some embodiments the tags comprise modified bases that can be subsequently detected during a sequencing reaction. Methods for detection of modified bases during sequencing reactions are known in the art and described at length in International Patent Application Publication No. WO2012065043, incorporated herein by reference in its entirety for all purposes.

The bis-biotinylated compounds of the invention also find utility in the medical sciences by providing a very stable connection between a streptavidin and an agent of interest, where the agent is to be retained in the kidney for a number of days, e.g., to treat a kidney disorder. In the body, streptavidin accumulates in the kidney and has been observed to remain in the kidneys of mice, rats, and rabbits for 3-4 days. This accumulation can comprise 15-20% of a dose of injected streptavidin, and is far greater than any accumulation in other tissues tested. (See, e.g., Schechter, et al. (1995) Kidney International 47:1327-1335, incorporated herein by reference in its entirety for all purposes.) As such, streptavidin can be used to deliver agents specifically to the kidneys, and such agents can include drugs, chemotherapeutic agents, radioactive isotopes, and the like. In certain aspects, the present invention provides such ligands linked to streptavidin via a bis-biotin linkage, which provides the benefit of better controlling the dosage of the agents being delivered to the kidney. Further, it provides a means to ensure a 1:1 stoichiometry of two different agents to the kidneys by linking one of each of the two agents to each streptavidin molecule to be introduced, and the higher stability of the bis-biotin linkage ensures that both agents remain bound as they are ferried to the kidneys by the streptavidin molecule.

Another application for the bis-biotinylated compounds of the invention involves delivery of various agents to target locations within an organism, e.g., detectable labels for imaging/theranostics, small molecule therapeutics, cytotoxic agents targeted to tumors, etc. These types of applications have been previously performed using mono-biotinylated compounds, e.g., see U.S. Patent Publications 20110014151 and 20130052130, which are incorporated by reference in their entireties for all purposes. Use of the bis-biotin tags instead of the mono-biotin strategies previously used will increase the stability of these delivery agents, thereby improving various aspects of these applications, including increasing the total amount of the agent that is delivered to the target location and decreasing the amount of potentially hazardous payload (e.g., cytotoxins) that is dissociated from the complex in non-target locations.

The methods and compositions herein can also be used to explore cellular signaling systems. For example, the signaling between two cellular components can be studied on at single-molecular-complex level by linking one of each to a streptavidin molecule, thereby bringing them together and promoting interaction between them. Similarly, interactions between two cellular components that do not naturally interact can also be explored in this way. Further, streptavidin polymers can be used to co-localize even more cellular components, creating a signaling network comprising multiple different components on a single streptavidin scaffold at a single reaction site. Further, the spatial relationship between these components can be tested by changing their location within the scaffold. Introduction of such compounds into a cell allows in vivo testing of the configuration on cell function, growth, division, death, and the like. This also provides an opportunity to engineer cells for specific purposes where an introduced signaling pathway provides a benefit to the cell, or to an organism into which the cell is to be introduced. Such engineered cells can be therapeutic cells, or can be cells engineered for biotechnological purposes, e.g., fuel production, pollution cleanup, production of commercially valuable molecules (e.g., drugs, antibodies, etc.) See, e.g., Wei, et al. (2012) Nature 488:384-388; and Sattely, et al. (2008) Natural Product Reports, 25:757-793, both of which are incorporated herein by reference in their entireties for all purposes.

The methods and compositions herein can also be used to enrich a nucleic acid mixture for loci of interest. In certain preferred embodiments, an oligonucleotide comprising a bis-biotin tag is complementary to a nucleotide sequence within a locus of interest. Specific hybridization of the oligonucleotide to the loci of interest and immobilization of the oligonucleotide via the bis-biotin tag allows for removal of other loci in the nucleic acid mixture, thereby enriching the mixture for the loci of interest. Where the mixture comprises double-stranded fragments, e.g., genomic DNA fragments, the nucleic acids are typically denatured prior to exposure to the bis-biotinylated oligo. Preferably, the location of the bis-biotin tag is selected to ensure the 3' end of the oligonucleotide can serve as a primer after binding to the loci of interest. This allows extension of the primer prior to removal of the non-specific nucleic acids, thereby providing a stronger linkage to the loci of interest. Another benefit is the production of a double-stranded molecule that can be removed from the bis-biotin tag, e.g., by endonuclease digestion, and can be further analyzed. In certain embodiments, the ends of the double-stranded molecule are capped with adaptors, e.g., adaptors having primer binding sites and/or stem-loop adaptors, to allow amplification and/or sequencing of the molecule. The bis-biotin tag can be immobilized to any solid surface comprising a biotin-binding agent, e.g., streptavidin and others noted herein, and such a surface includes beads, arrays, columns, and the like.

The bis-biotin tags described herein can be used to improve assembly of two-dimensional ordered arrays of streptavidin crystals on a surface described by Ringler and Schulz (2003) Science 302, 106-109. The use of bis-biotinylated streptavidin would make such arrays more robust, e.g., to heat, etc. Further, attaching to two points in the streptavidin tetramer would provide better control over where the neighboring molecule is placed by virtue of the two tethers linked to the biotins. Yet further advantages can be achieved by taking advantage of the alternate stoichiometries provided by the bis-biotin linkages.

The bio-biotin linkages are also applicable to the lanthanide-streptavidin labeling methods used for medical imaging applications with metal chelation described in Aime, et al. (2006) Coordination Chemistry Reviews, 250 (11-12), 2006,1562-1579, which is incorporated herein by reference in its entirety for all purposes. They can also be used to improve the methods of Howarth and Ting for imaging proteins in living cells by providing a bis-biotin linkage at the cell surface which can bind to a dimer of streptavidin with a higher stability than the mono-biotin tags they describe. Further, where the streptavidin is further conjugated to a bis-biotin-linked biophysical probe of interest (e.g., a fluorophore or quantum dot), a further aspect of the method is improved as compared to the single-biotin-labeled probe. See, e.g., Nature Protocols (2008) 3(3):534-545, which is incorporated herein by reference in its entirety for all purposes.

Yet further, the bis-biotin linkages described herein are beneficial to the methods described in Chivers, et al. (2010) Nat. Methods 7(5):391-393, which is incorporated herein by reference in its entirety for all purposes. The authors of that paper identified a mutant streptavidin, traptavidin, that shows ~10-fold slower biotin off-rate, increased mechanical strength, and improved thermostability. They further demonstrate that the motor protein FtsK can strip proteins from DNA, rapidly displacing streptavidin from biotinylated DNA; traptavidin resisted displacement and thus indicated the force generated by FtsK translocation. The higher stability of the bis-biotin linkages would further stabilize the binding of DNA (or other reactant) to traptavidin (and also streptavidin). For example, the bis-biotin linkages will increase resistance to displacement by motor proteins traveling along a biotinylated DNA molecule.

In additional aspects, the bis-biotin linkages provided herein can be used in combination with the SpyTag/SpyCatcher system developed by the Howarth lab and described in the literature, e.g., in Zakeri, et al. (2012) "Peptide tag forming a rapid covalent bond to a protein, through engineering a bacterial adhesin," PNAS 109(12):E690-7; Schoene, et al. (2014) Angew. Chem. Int. Ed. 53: 1-5; Zhang, et al. (2013) J. Am. Chem. Soc. 135: 13988-13997; and Fierer, et al. (2014) Proc. Natl. Acad. Sci. USA E1176-E1181, each of which is incorporated herein by reference in its entirety for all purposes. Briefly, the bacteria Streptococcus pyogenes has a fibronectin-binding protein FbaB that contains a domain with a spontaneous isopeptide bond between a lysine residue and an aspartate residue. The Howarth lab split this domain and used the fragments to engineer two peptides, "SpyTag" and "SpyCatcher." These individual peptides are still capable of efficiently forming a covalent amide bond, and were used to create an intermolecular bond between a maltose binding protein fusion comprising the SpyTag peptide and the SpyCatcher peptide.

Figure 10:
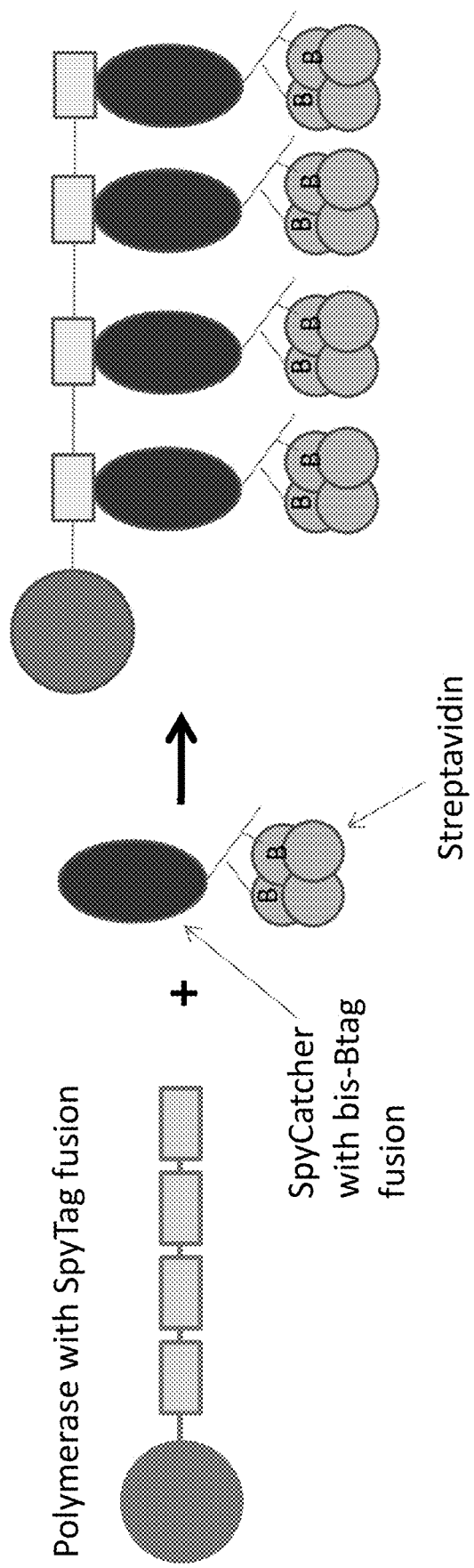
FIG. 10 provides an illustrative embodiment of a bis-biotin tagging strategy in which four SpyTags are fused to a polymerase enzyme.

In certain embodiments of the present invention, a reactant is coupled to multiple bis-biotin tags using the SpyTag/SpyCatcher system in a novel, multiplex strategy. The general mechanism is to couple multiple SpyTags to a single reactant, and then expose this reactant-(SpyTag)$_n$ to SpyCatchers, each of which is coupled to a bis-biotin tag. In doing so, the reactant is provided multiple bis-biotin tags for binding, e.g., to avidin or streptavidin. The streptavidin can be bound to the bis-biotin tags before or after formation of the covalent bond between the SpyTags and the SpyCatchers. For example, in preferred embodiments, the reactant is a protein that is fused to multiple SpyTags. The protein can be enzymatic or non-enzymatic, and in certain preferred embodiments, is a fusion protein comprising a polymerase enzyme and multiple SpyTags. Methods of engineering fusion proteins are conventional in the art and well known to the ordinary practitioner, e.g., as provided in Horton, et al. (1989) Gene 77(1):61-8, which is incorporated herein by reference in its entirety for all purposes. Although the number of SpyTags fused to the reactant is generally determined by the practitioner based upon the intended use for the construct, the number will typically range from 2-10 SpyTags, preferably from 3-8 SpyTags, and in certain preferred embodiments, at least four SpyTags. For example, FIG. 10 provides an illustrative embodiment of the bis-biotin tagging strategy in which four SpyTags are fused to a polymerase enzyme in order to provide an ultimate complex (following covalent amide bond formation between the SpyTags and bis-biotinylated SpyCatchers) having four bis-biotin tags.

The resulting reactant-(SpyTag)$_n$-(SpyCatcher+bis-biotin tag)$_n$ complex is useful for various applications. For example, where each bis-biotin tag in the complex is bound to a streptavidin tetramer, the complex can be immobilized on a surface comprising moieties that can bind to the open binding sites of the tetramer, e.g., biotin or bis-biotin moieties on a surface. As noted elsewhere herein, surfaces contemplated include, but are not limited to, beads, microarrays, columns, semi-solid surfaces, waveguide substrates, within nanoholes (e.g., zero-mode waveguides), etc. In other embodiments, multiple streptavidin tetramers are bound to accessory proteins that are beneficial in close proximity to the reactant. For example, where the reactant is an enzyme, the accessory proteins can serve to provide a substrate to the enzyme, or can further process a product of the catalytic activity. In a specific embodiment, the reactant is a polymerase enzyme and the accessory protein is a single-stranded binding protein that helps to remove secondary structure from a single-stranded template ahead of the polymerase. In alternative embodiments, the reactant is a polymerase enzyme and the accessory protein is a helicase that that helps to unwind a double-stranded template ahead of the polymerase. The availability of multiple streptavidin for binding accessory proteins is especially beneficial in cases where the accessory proteins function as multimers, as in the case of single-stranded DNA binding proteins.

Figure 11:
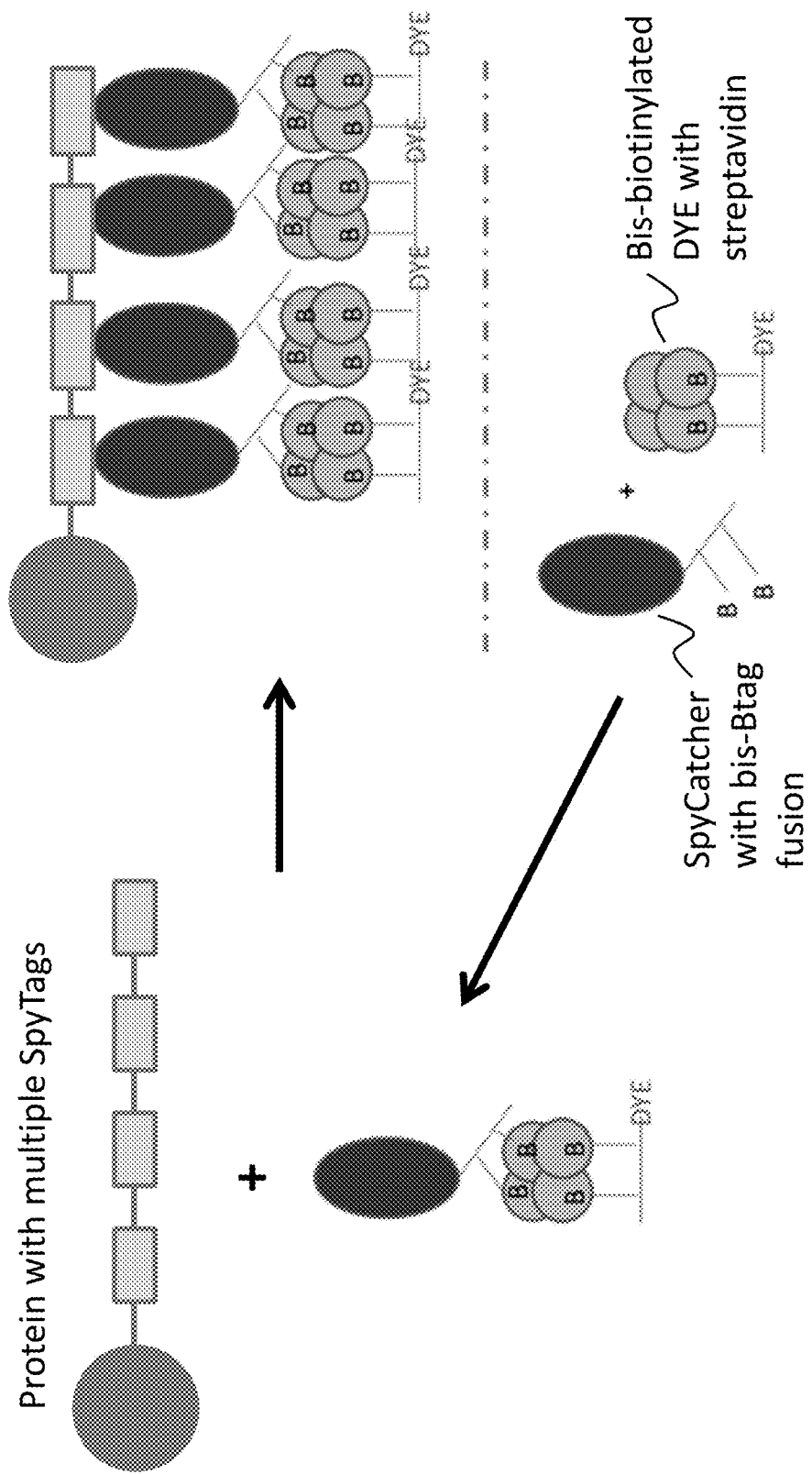
FIG. 11 provides an illustrative embodiment of a method of forming a complex comprising bis-biotinylated dyes bound to streptavidin molecules, which are bound to bis-biotinylated SpyCatcher peptides covalently linked to a protein-SpyTag fusion.

In yet further embodiments, the multiple streptavidin molecules provide binding sites for tags, e.g., affinity tags, detectable tags (e.g., dyes), and the like. In particular, the Applicants provide methods for using the SpyTag/SpyCatcher system for providing polyvalency of labeling while excluding crosslinking of target proteins. For example, where affinity tags are bound to the streptavidin molecules, e.g., preferably via a bis-biotin moiety, the complex can be more efficiently purified a complex having only a single affinity tag. In other embodiments, multiple detectable tags can be associated with the complex via the streptavidin molecules. For example, a bis-biotinylated fluorescent dye can be bound to each of the streptavidin molecules. In some embodiments, the dyes are all the same dye, thereby increasing the total emission from the complex upon illumination with the appropriate excitation wavelength. Alternatively, the dyes can be chosen such that energy transfer occurs between two or more of them, e.g., as in the case of fluorescence resonance energy transfer (FRET). As such, one or more dyes in the complex may be the same dye, and one or more may be different dyes. The complexes can be assembled in various ways. In some embodiments, a bis-biotinylated dye is bound to the streptavidin prior to the streptavidin being bound to a bis-biotinylated SpyCatcher peptide, and the resulting complex is subsequently bound to the protein with multiple SpyTags, as illustrated in FIG. 11. In other embodiments, the bis-biotinylated SpyCatcher peptide is first bound to the protein-SpyTag fusion, and subsequent to covalent bond formation, streptavidin is bound to the bis-biotin. Another bis-biotinylated moiety (e.g., a tag) is bound to the streptavidin either before or after the streptavidin is bound to the bis-biotinylated SpyCatcher peptide. While this disclosure refers primarily to the SpyTag peptide, but proteins related to SpyTag may also be used, and such proteins have been disclosed in the literature. See, e.g., Takakura, et al. (2009) FEBS Journal 276(5):1383-97, which is incorporated herein by reference in its entirety for all purposes.

Additional applications of the methods and compositions described herein include use in single-molecule imaging on surfaces coated with biotin-binding agents, such as streptavidin, avidin, traptavidin, etc. Imaging of such single-molecule assays is described in Zareh, et al. (2011) Microscopy Research and Technique 74:682-687, which is incorporated herein by reference in its entirety for all purposes. The use of bis-biotinylated reactants increase the stability of the binding to the coated surface, thereby facilitating detection of the reactants in the solution.

Still other applications of the methods and compositions described herein include use in single-molecule sequencing, e.g., of a template in a polymerase/template/primer complex immobilized on a surface coated with biotin-binding agent (e.g., streptavidin, avidin, traptavidin, etc.). Single-molecule sequencing in zero-mode waveguides is described, e.g., in U.S. patent application publications 2003/0044781 and 2007/0036511, U.S. Pat. Nos. 6,917,726, 7,056,676, 7,056, 661, 7,052,847, and 7,033,764, and Eid et al. (2009) "Real-time DNA sequencing from single polymerase molecules" Science 323:133-138, which are incorporated herein by reference in their entirety for all purposes. Without limitation to any particular mechanism, the use of bis-biotinylated reactants can improve loading of polymerase/template/primer complex onto the surface (e.g., by increasing density of biotin on the surface, improving loading kinetics, and/or increasing avidity) and can increase the stability of complex binding to the coated surface (e.g., since dissociation of one of the two biotin groups from the biotin-binding agent will not result in dissociation and thus loss of the complex from the surface), thereby facilitating collection of sequence data.

In light of the teachings herein, the benefits of the described methods and compositions will be clear to the ordinary artisan, both in the applications described herein, as well as other applications in the art. For example, bis-biotin tags are also useful in the construction of two-dimensional streptavidin arrays wherein crystals of streptavidin are bound to biotinylated lipid monolayers at the air-water interface, e.g., as described by Farah, et al. (2001) Langmuir 17:5731-5735, which is incorporated herein by reference in its entirety for all purposes. The use of bis-biotinylated lipid monolayers would allow additional control of the formation of such two-dimensional protein arrays by limiting the number of covalent bonds linking the streptavidin to the lipid monolayer. They also provide similar advantages in cell surface display applications, e.g., as described in Furukawa, et al. (2006) Biotechnol. Prog. 22:994-997, which is incorporated herein by reference in its entirety for all purposes, by increasing the stability and longevity of the streptavidin complex on the cell surface.

Those of skill in the art recognize from the description above that the present invention provides many advantages and more application than prior art methods for using bis-biotinylation tags in various applications. The high binding affinity of the bis-biotin interaction provides advantages for labeling, localization, detection, immobilization, and purification methods, as well. As can be appreciated from the disclosure above, the present invention has a wide variety of applications. Accordingly, it is to be understood that the above description and the following examples are offered by way of illustration, and are not intended to be restrictive or limiting.

It should be readily apparent to one skilled in the art that various embodiments and modifications may be made to the invention disclosed in this application, including but not limited to combinations of various aspects of the invention, without departing from the scope and spirit of the invention. The scope of the invention should, therefore, be determined not with reference to the above description, but should instead be determined with reference to the appended claims, along with the full scope of equivalents to which such claims are entitled. Unless otherwise clear from the context or expressly stated, any concentration values provided herein are generally given in terms of admixture values or percentages without regard to any conversion that occurs upon or following addition of the particular component of the mixture. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

IV. Examples

Purification

In certain aspects, a method is provided for purifying a bis-biotinylated streptavidin (i.e., a streptavidin bound to a single, bis-biotinylated molecule such that two binding sites are occupied by the bis-biotin and two binding sites are open) away from both doubly bis-biotinylated streptavidin (i.e., bound to two bis-biotinylated molecules such that all four binding sites are occupied by the bis-biotins and no binding sites are open) and streptavidin having all binding sites unoccupied. In certain preferred embodiments, ion-exchange chromatography provides a way to separate different complexes formed by mixing bis-biotinylated molecules with streptavidin. For example, the method is particularly effective when separating streptavidin complexes comprising charged groups, e.g., negatively charged dye molecules.

Figure 8:
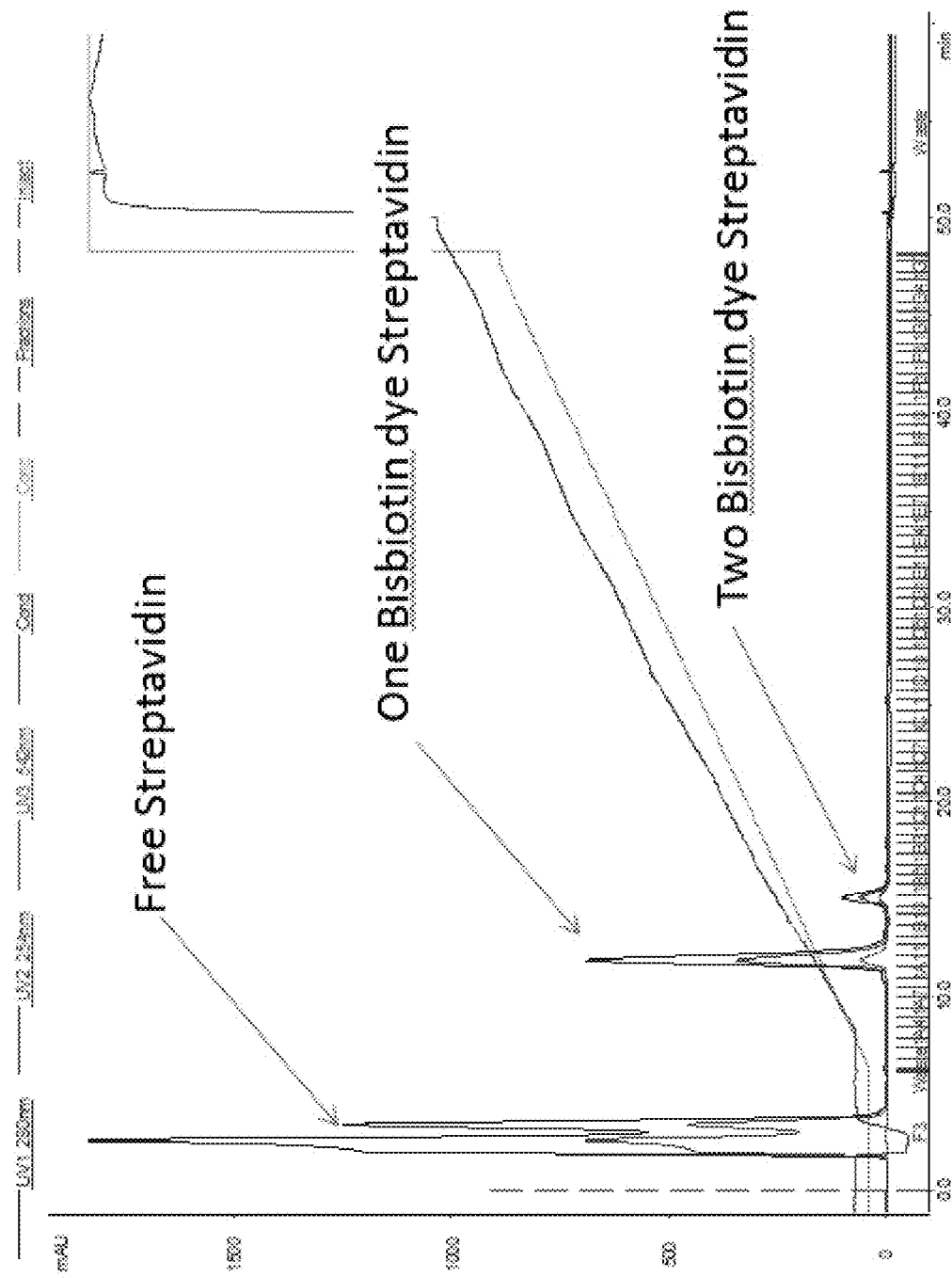
FIG. 8 provides an example of a typical chromatogram for fractions collected from an ion exchange column.

A typical ion-exchange purification of a single bis-biotin dye moiety bound to streptavidin (e.g., the labeling reagent illustrated in FIG. 2) was performed as follows. A 1 ml aliquot of recombinant streptavidin at 10 mg/ml solution (10% glycerol, 50 mM KOAc, 5 mM Tris pH7.4) was thawed and placed in a 5 ml tube. The bis-biotin dye was added to 4 mls of Buffer A (5 mM Tris HCl pH 7.4, 20% acetonitrile) to a final concentration of 18.75 µM. In 250 µl aliquots, the diluted dye was added to the concentrated streptavidin with re-pipetting to mix, using a new pipet tip with each addition until the two solutions were completely combined (adding the diluted dye to the concentrated enzyme favors the formation of the single dye bound species). The resulting 5 ml solution was then loaded into a 5 ml sample loop of an AKTAexplorer® 10 FPLC equipped with a MonoQ_10/100_GL ion exchange column. The sample was purified using a linear gradient of 5% Buffer A to 50% Buffer B (5 mM Tris HCl pH 7.4, 20% acetonitrile, 2 M NaCl) over 20 column volumes. 2 ml fractions were collected while monitoring the wavelengths at 254, 280, and 542 nm. A typical chromatogram is shown in FIG. 8. The fractions containing the streptavidin complexes linked to a single bis-biotin dye were pooled and concentrated using a 4 ml Amicon® Ultra spin concentrator (30K), and the sample was diluted to 4 mls in a solution of 5 mM Tris HCl pH 7.4 and subsequently reconcentrated to exchange the buffer.

Streptavidin Tetramer Stabilization

Figure 9:
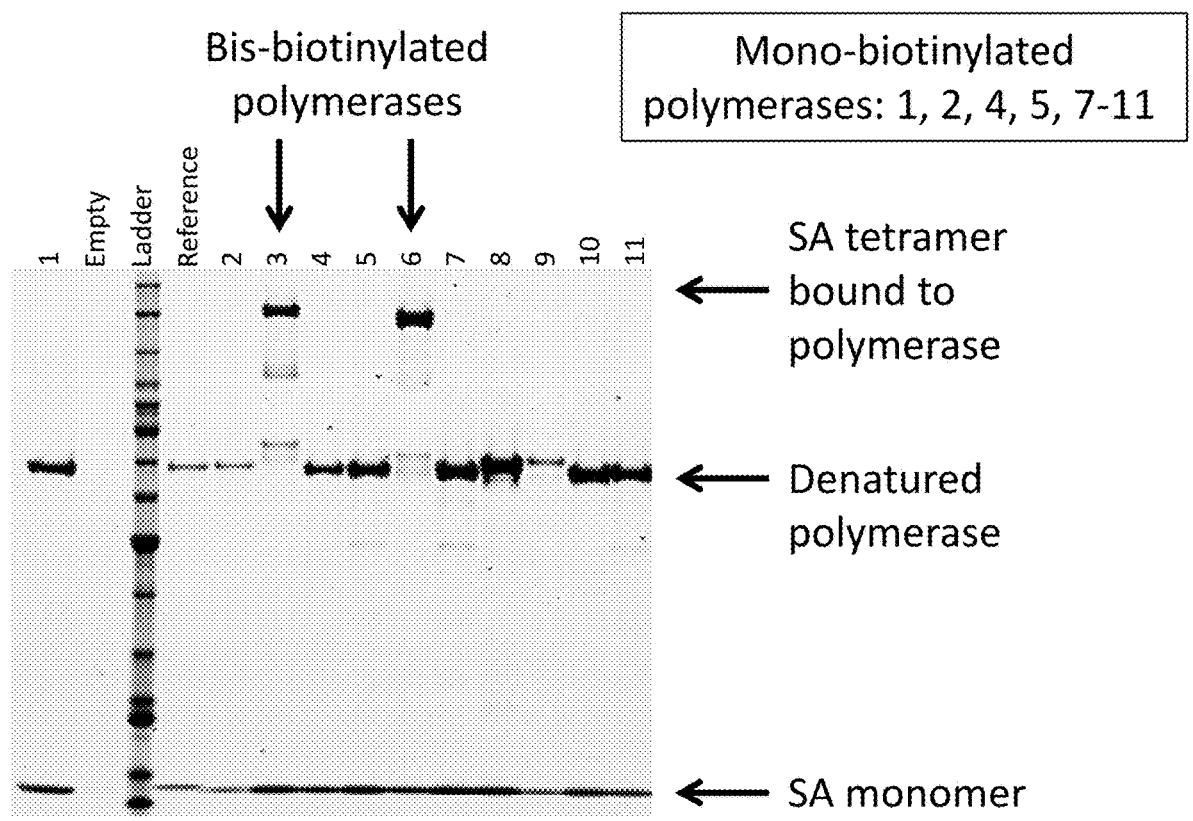
FIG. 9 provides an image of an exemplary high-throughput polymerase screening gel.

It was demonstrated that a single bis-biotin tag bound to a streptavidin tetramer will stabilize the tetramer, even under the extreme conditions of high temperature over an extended period followed by electrophoresis in the presence of a detergent. In one experiment, 27 µl of loading buffer was added to 3 µl of protein sample comprising a biotinylated polymerase bound to a streptavidin tetramer. The mixture was heated at 90° C. for 20 minutes, and 10 µl of each of the resulting mixtures was loaded onto an SDS-PAGE gel, and stained with SyPro® Ruby following standard protocols. FIG. 9 provides an image of one exemplary high-throughput polymerase screening gel. The lanes numbered 1-11 each contain a different polymerase enzyme. Most are linked to a single biotin tag, but the two designated as 3 and 6 have bis-biotin tags. The various bands are identified to the right of the gel. The lowest bands contain only streptavidin monomers that were dissociated from tetramers during the harsh treatment. The middle bands are polymerases that were also dissociated from the streptavidin tetramers. The only two complexes that remained intact are apparent as the two bands that run high on the gel. Each "supershifted" band comprises streptavidin bound to one of the bis-biotinylated polymerases. The fact that the supershifted bands show up only with the bis-biotinylated polymerase-streptavidin complexes indicates the superior stability of the bis-biotin strategy. In all other cases, the streptavidin tetramer and the singly biotinylated polymerase are denatured and separated.

Comparison of a Mono-biotin Linkage to a Bis-biotin Linkage in a Single Streptavidin Complex The higher stability of a bis-biotin linkage to streptavidin as compared to a mono-biotin linkage was demonstrated using a complex comprising a streptavidin molecule having one dimer in the tetramer bound to a bis-biotinylated fluorescent dye, and having the other dimer bound to two individual mono-biotinylated compounds comprising multiple nucleotide polyphosphates, also termed "base clusters." Examples of such base clusters, as well as complexes comprising streptavidin, dye, and base clusters, are described in detail in U.S. patent application Ser. No. 13/767,619, filed Feb. 14, 2013, and incorporated herein by reference in its entirety for all purposes. The complex at a concentration of 57 µM, was incubated with 10× excess of free biotin in 5 mM Tris, pH 7.4. The free biotin served to occupy empty biotin-binding sites on the streptavidin complex when there was dissociation of the biotin moieties linked to the dye or base clusters. The timecourse was run for 900 minutes and 30 µl time points taken at 5, 10, 20, 40, 220, and 900 minutes were flash frozen. After the timecourse was run, the time points were diluted to 500 µl in 5 mM Tris, pH 7.4. The samples were then injected into an analytica MonoQ™ anion-exchange column (1 mM) and analysis was performed according to manufacturer's instructions (GE Healthcare, Uppsala, Sweden) using Buffer A (5 mM Tris, pH 7.4; 20% acetonitrile (ACN)) and Buffer B (5 mM Tris, pH 7.4; 2 M NaCl; 20% ACN). The results showed that one of the mono-biotinylated base clusters dissociates readily, with a half-life of two hours, while the bis-biotinylated dye does not appreciably dissociate from the complex on this timescale. Interestingly, the second base cluster also did not appreciably dissociate, and although not wishing to be bound by theory, this finding implies there is some negative cooperativity of binding of the two mono-biotinylated base clusters to the streptavidin complex, possibly due to charge-based and/or steric interferences.

Preparation of (Biotin-X-Cy)$_2$-T2-COOH

Figure 12:
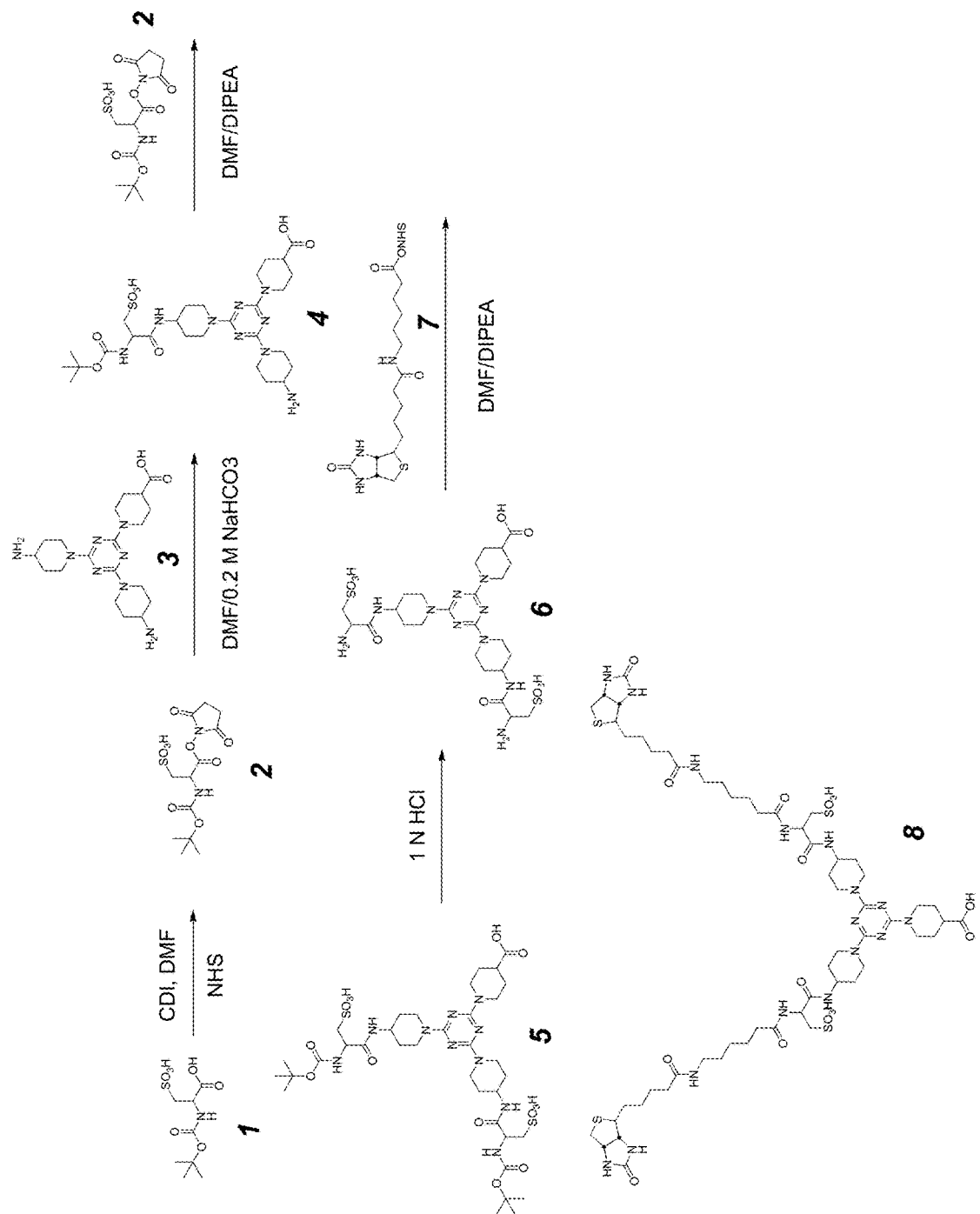
FIG. 12 schematically illustrates an exemplary synthesis of bis-biotin containing compound (Biotin-X-Cy)$_2$-T2-COOH.

Synthesis of bis-biotin containing compound (Biotin-X-Cy)$_2$-T2-COOH including a carboxylic acid reactive functional group is schematically illustrated in FIG. 12. Inclusion of the (L)-cysteic acid increases both water and organic solvent solubility as compared to (Biotin-X)$_2$-T2-COOH.

Activation of Boc-Cysteic Acid

To a solution of Boc-Cysteic acid 1 (5.00 g, 18.58 mmol) in anhydrous DMF (50 mL) was added carbonyldiimidazide (CDI, 3.31 g, 20.4 mmol), N-hydroxysuccinimide (NHS, 20.4 mmol) and stirred for 16 hrs under nitrogen atmosphere.

Preparation of (Boc-Cy)$_2$-T2

To a solution of T2 3 (2.00 g, 4.94 mmol) in 0.2 M NaHCO$_3$ (12 mL) was added a solution of Boc-Cysteic-NHS 2 (8 mmol) in DMF (22 mL) and stirred at room temperature under nitrogen for 2 hrs. Solvents were evaporated off using rotary evaporator under vacuum to a syrup 4. To it was added another solution of Boc-Cysteic-NHS 2 (6 mmol) in DMF (16.5 mL) and DIPEA (0.5 mL) and stirred for 1.5 hrs. Added another solution of Boc-Cysteic-NHS (3 mmol) in DMF (8 mL) and continue the stirring overnight. Concentrated the reaction solution under low vacuum to a residue, re-dissolved the residue in 0.1 M TEAA buffer, filtered and subjected it to the reverse-phase HPLC separation to give the desired product (Boc-Cy)$_2$-T2 5 in quantitative yield.

Preparation of Cy$_2$-T2

To the dried (Boc-Cy)$_2$-T2 5 (~4.94 mmol) was added 1N HCl aqueous solution (50 mL) and stirred overnight. Concentrated the solution under vacuum to dryness and subjected it to a RP-HPLC purification. The fractions of product were pooled together, concentrated under vacuum to give the desired product after drying. There was obtained 2.961 g (4.19 mmol, 85%) of product Cy$_2$-T2 6.

Preparation of (Biotin-X-Cy)$_2$-T2-COOH

To a solution of Cy$_2$-T2 6 (2.961 g, 4.19 mmol) in DMF (40 mL) was added biotin-X-NHS 7 (4.38 g, 9.64 mmol) and DIPEA (1 mL). The solution was stirred at room temperature under nitrogen atmosphere overnight. Solvent was evaporated off under vacuum and the residue was purified by RP-HPLC to give 4.99 g (3.5 mmol, 84% yield) of the desired product (Biotin-X-Cy)$_2$-T2-COOH 8.

Comparison of Immobilization on Bis-biotin and Mono-biotin Coated Surfaces

Zero-mode waveguide (ZMW) chips are coated with either a biotin-PEG-silane or with a bis-biotin-PEG-silane. For each chip, polymerase/template/primer complex including a biotinylated polymerase is bound to streptavidin and loaded onto the chip. Fluorescently labeled nucleotide analogs are provided, and reactions are monitored by single molecule sequencing on a PACBIO™ RS sequencing instrument using standard laser and analysis options, basically as described in Eid et al. (2009) Science 323:133-138 (including supplemental information) and Korlach et al. (2010) Methods in Enzymology 72:431-455. The number of individual ZMWs loaded with a single polymerase/template/primer complex is identified in an initial 10' movie. Additional 10' movies are collected at various time points thereafter after refreshing with new buffer, and the fraction of singly loaded ZMWs identified from the initial movie that are still producing sequence data is determined.

Figure 13:
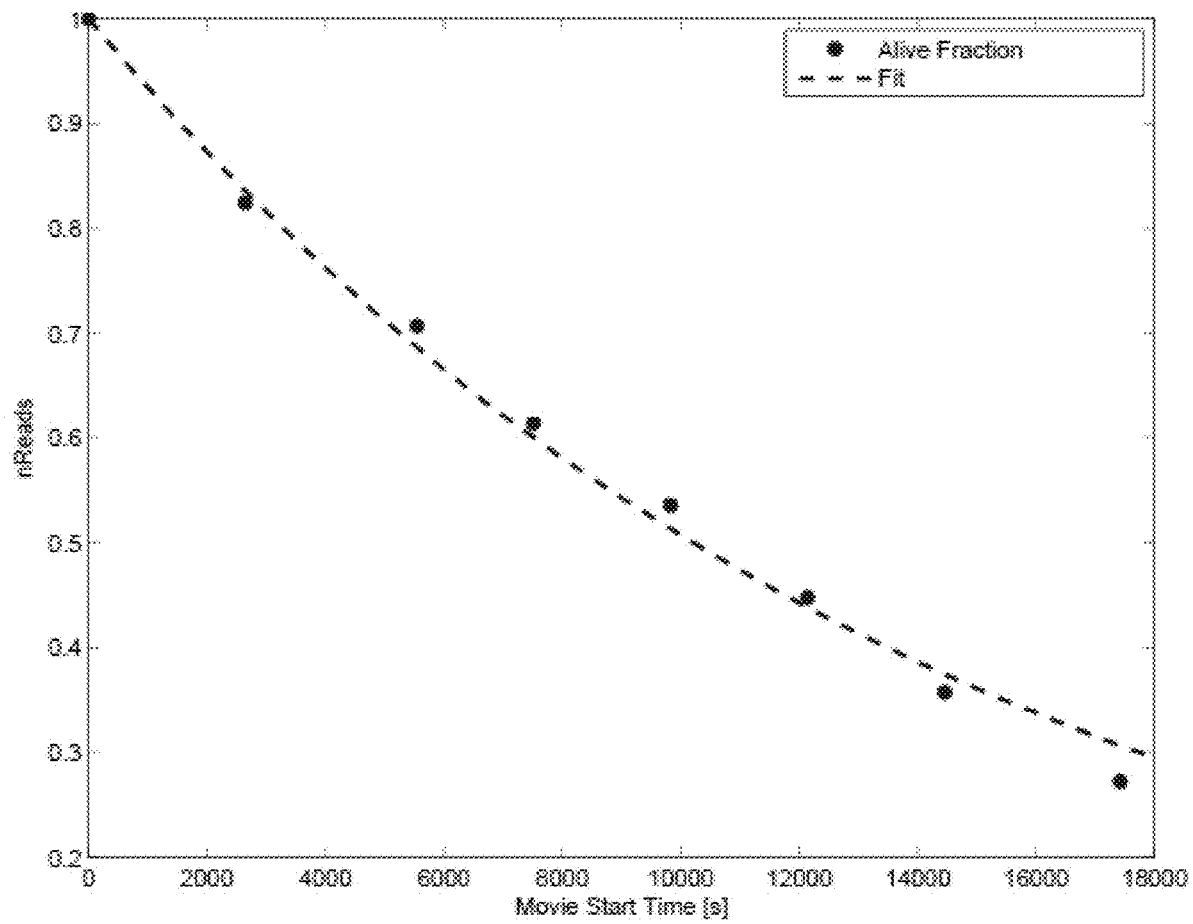
FIG. 13 shows a graph illustrating fitting of a single exponential to sequencing time points to determine rate of sequencing loss.

An example of the resulting graph is shown in FIG. 13. The fraction of ZMW traces remaining active over time (data points indicated by circles) is fit to a single exponential (dashed line) to calculate the rate of sequencing loss over time. The exponential time constant T (the inverse of the decay rate) is calculated. The average sequencing rate (b/s) is multiplied by the T (s) to determine the decay in bases. Since the ZMWs are not illuminated during the intervening periods between movies, loss of sequencing activity is assumed to be due primarily to dissociation of the polymerase from the bottom surface of the ZMW.

Data for an exemplary experiment is presented in Table 1. Polymerases A and B are mutant Φ29 polymerases having two biotinylation sequences separated by a 12 amino acid linker (U.S. patent application No. 62/258,414). Polymerase C includes the same mutations as polymerase A but bears only a single biotinylation sequence. Polymerases D-G include the same mutations as polymerase A and carry two biotinylation sequences separated by shorter amino acid linkers of varying lengths.

TABLE 1

Bis-biotin coated chips display large gains in polymerase binding stability, especially for bis-biotinylated polymerases.

| | Tau (seconds) | | | Tau (bases) | | |
|---|---|---|---|---|---|---|
| Polymerase | mono-biotin | bis-biotin | % change | mono-biotin | bis-biotin | % change |
| A | 56820 | 93612 | 65% | 85271 | 151340 | 77% |
| B | 64579 | 117800 | 82% | 105230 | 209560 | 99% |
| C | 33223 | 38971 | 17% | 42750 | 53639 | 25% |
| D | 64803 | 109075 | 68% | 96610 | 175120 | 81% |
| E | 56904 | 92228 | 62% | 85749 | 147400 | 72% |
| F | 56775 | 98972 | 74% | 81629 | 158350 | 94% |
| G | 55415 | 93706 | 69% | 83347 | 150680 | 81% |

Preparation of [SG1-Lys(Biotin)]$_2$-T1-NH$_2$

Figure 16:
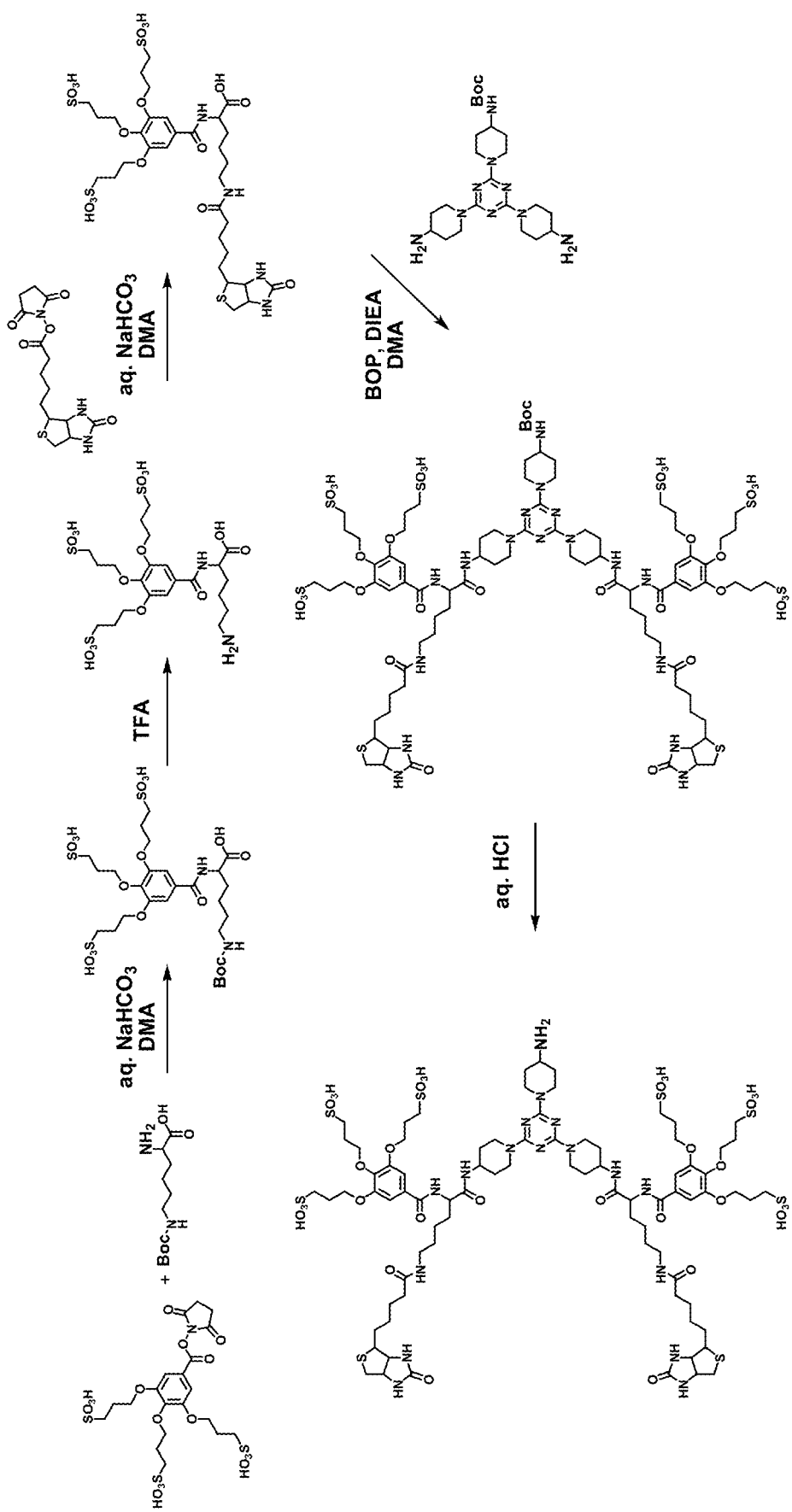
FIG. 16 schematically illustrates an exemplary synthesis of bis-biotin containing compound [SG1-Lys(Biotin)]$_2$-T1-NH$_2$.

Synthesis of bis-biotin containing compound [SG1-Lys(Biotin)]$_2$-T1-NH$_2$ including an amine reactive functional group is schematically illustrated in FIG. 16. Inclusion of the 3,4,5-tris(3-sulfopropoxy)benzoic acid (SG1) increases both water and organic solvent solubility.

Preparation of SG1-Lys(Boc)-COOH

A solution of SG1-NHS (N-hydroxysuccinimide ester of 3,4,5-tris(3-sulfopropoxy)benzoic acid, 100 mM in DMA, 500 µL, 50 µmol) was added to a suspension of NH$_2$-Lys(Boc)-COOH (36.9 mg, 150 µmol) in aq. NaHCO$_3$ (0.4 M, 500 µL) and the mixture was stirred at room temperature for 24 h. The product was purified by a reverse phase HPLC (Waters XTerra C18 RP 50×100 column, 0-26% acetonitrile in 0.1 M TEAB, Akta Purifier) to yield SG1-Lys(Boc)-COOH (32.1 mg, 30 µmol, 60% yield, TEA salt). LCMS: Calculated Mass 764.2, Observed Mass 763.2 (M$^-$).

Preparation of SG1-Lys(Biotin)-COOH (2 steps)

TFA (2 mL) was added to SG1-Lys(Boc)-COOH (32.1 mg, 30 µmol, TEA salt) and the solution was kept at room temperature for 30 min. The mixture was concentrated in vacuo, co-evaporated with acetonitrile (3×), and dried in HV. SG1-Lys(NH$_2$)—COOH*TFA was used for the next step without purification. LCMS: Calculated Mass 664.1, Observed Mass 663.3 (M$^-$).

A solution of Biotin-NHS (20.5 mg, 60 µmol) in DMA (750 µL) was added to a solution of SG1-Lys(NH$_2$)—COOH * TFA (30 µmol) in aq. NaHCO$_3$ (0.4 M, 500 µL) and the mixture was stirred at room temperature for 3 h. The product was purified by a reverse phase HPLC (Waters XTerra C18 RP 50×100 column, 0-20% acetonitrile in 0.1 M TEAB, Akta Purifier) to yield SG1-Lys(Biotin)-COOH (30.8 mg, 25.8 µmol, 86% yield, TEA salt). LCMS: Calculated Mass 890.2, Observed Mass 889.4 (M$^-$).

Preparation of [SG1-Lys(Biotin)]$_2$-T1-Boc

A solution of BOP (200 mM in DMA, 257.8 μL, 51.6 μmol, 5.0 eq) was added to a mixture of SG1-Lys(Biotin)-COOH (100 mM in DMA, 257.8 μL, 25.8 μmol, 2.5 eq), N-Boc-NH-T1-(NH$_2$)2 (40 mM in DMA, 257.8 μL, 10.3 μmol, 1.0 eq, prepared from T1-(NH$_2$)3 and Boc$_2$O), and DIEA (400 mM in DMA, 257.8 μL, 103 μmol, 10 eq) and the solution was kept at room temperature for 3.5 h. The product was purified by a reverse phase HPLC (Waters XTerra C18 RP 50×100 column, 0-36% acetonitrile in 0.1 M TEAB, Akta Purifier) followed by an ion exchange chromatography (GE Q Sepharose HP 25 mL column, 0-60% 1.5 M TEAB with 20% acetonitrile, Akta Purifier) to yield [SG1-Lys(Biotin)]$_2$-T1-Boc (15.8 mg, 5.59 μmol, 54% yield, TEA salt). LCMS: Calculated Mass 2219.7, Observed Mass 1109.8 (M$^{2-}$/2).

Preparation of [SG1-Lys(Biotin)]$_2$-T1-NH$_2$

A solution of [SG1-Lys(Biotin)]$_2$-T1-Boc (15.8 mg, 5.59 μmol) in aq. HCl (3 M, 4 mL) was kept at room temperature for 16 h. Triethylamine (1.67 mL) was added to the chilled mixture followed by aq. TEAB (1.5 M, 3 mL). The product was purified by a reverse phase HPLC (Waters XTerra C18 RP 30×100 column, 0-30% acetonitrile in 0.1 M TEAB, Akta Purifier) to yield [SG1-Lys(Biotin)]$_2$-T1-NH$_2$ (12.8 mg, 4.87 μmol, 87% yield, TEA salt). LCMS: Calculated Mass 2119.7, Observed Mass 1059.7 (M$^{2-}$/2).

What is claimed is:

1. A compound having the formula

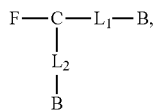

wherein F is a reactive functional group, C is a core group, L$_1$ is a first linking group, L$_2$ is a second linking group, and B is a biotin group, wherein L$_1$ and L$_2$ are identical groups selected from the group consisting of:

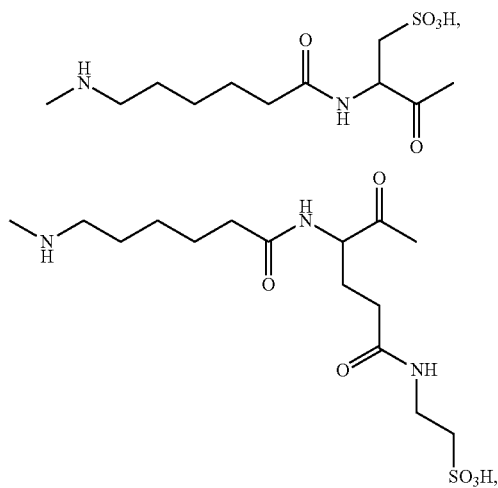

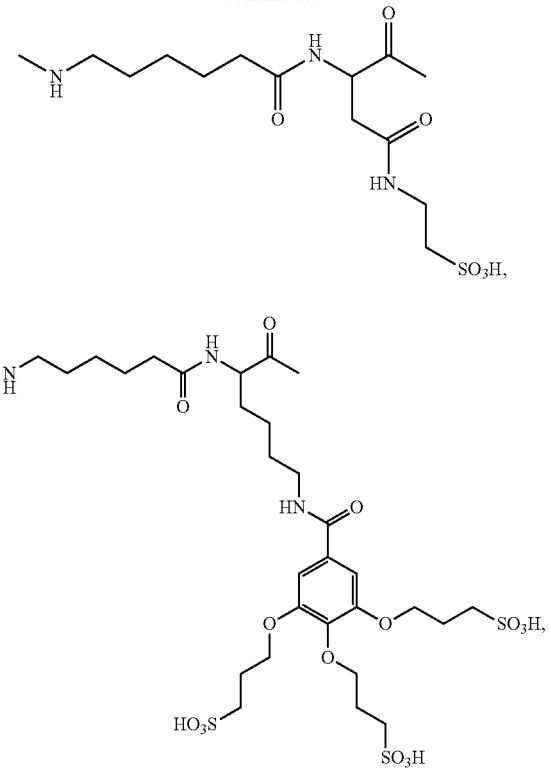

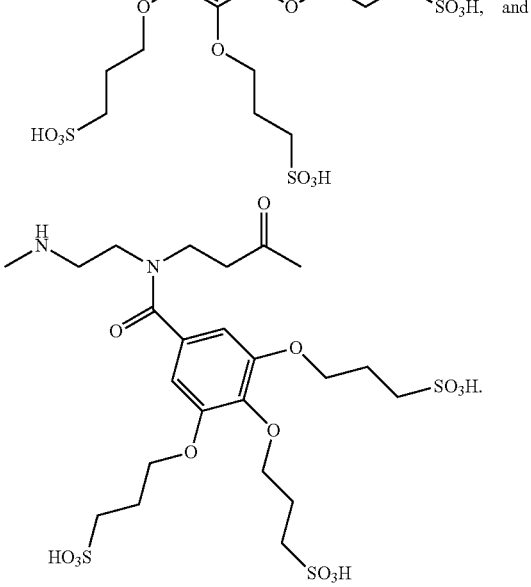

2. The compound of claim 1, wherein F is a carboxylic acid group or an amino group.

3. The compound of claim 1, wherein F is an azide group or an alkyne group.

4. The compound of claim 1, wherein C comprises a six-membered ring.

5. The compound of claim 4, wherein C comprises a tri-substituted aromatic six-membered ring.

6. The compound of claim 4, wherein C comprises a tri-substituted triazine.

7. The compound of claim 4, wherein C comprises a tri-substituted cyclohexane ring.

8. The compound of claim 1, wherein the compound is

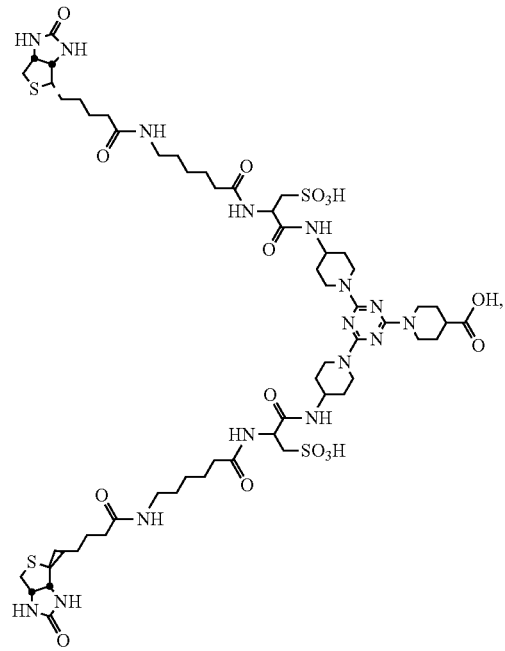

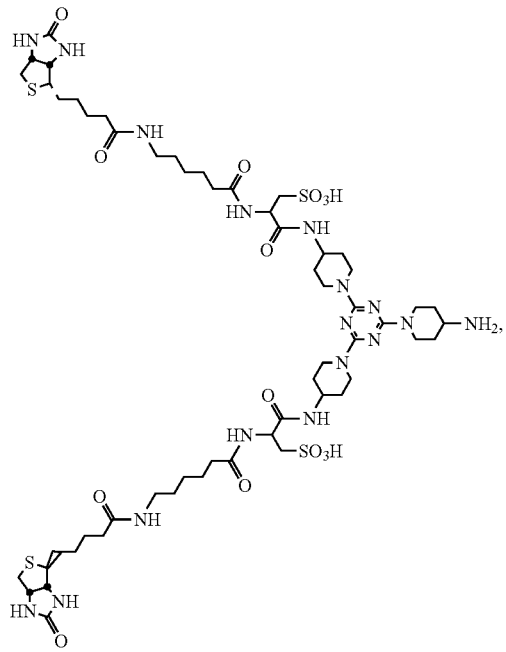

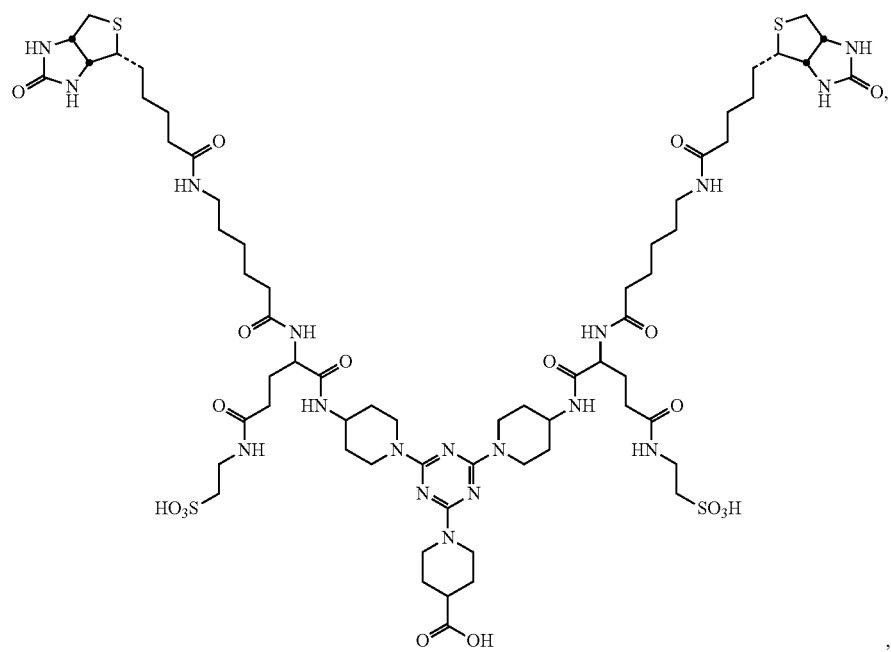

,

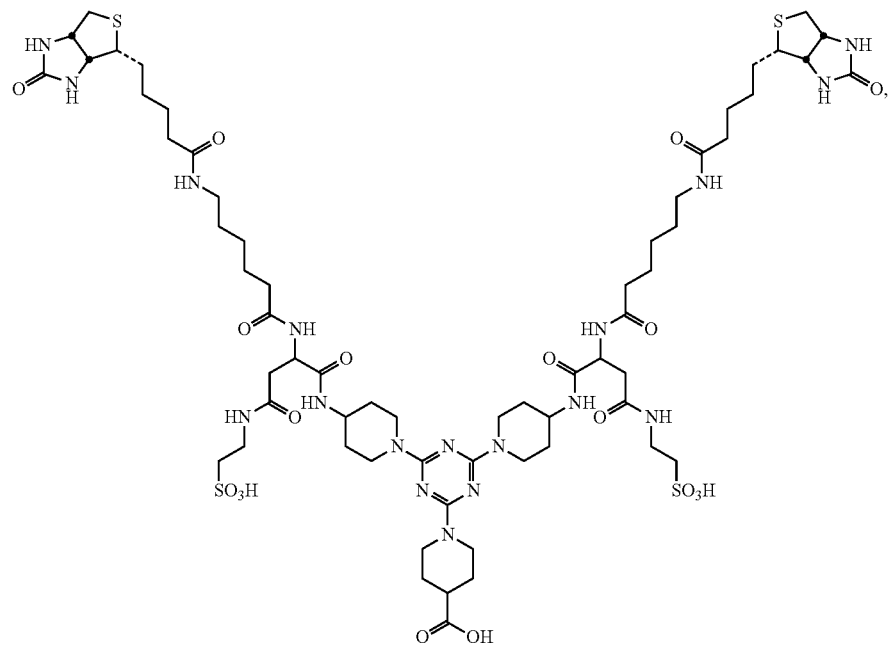
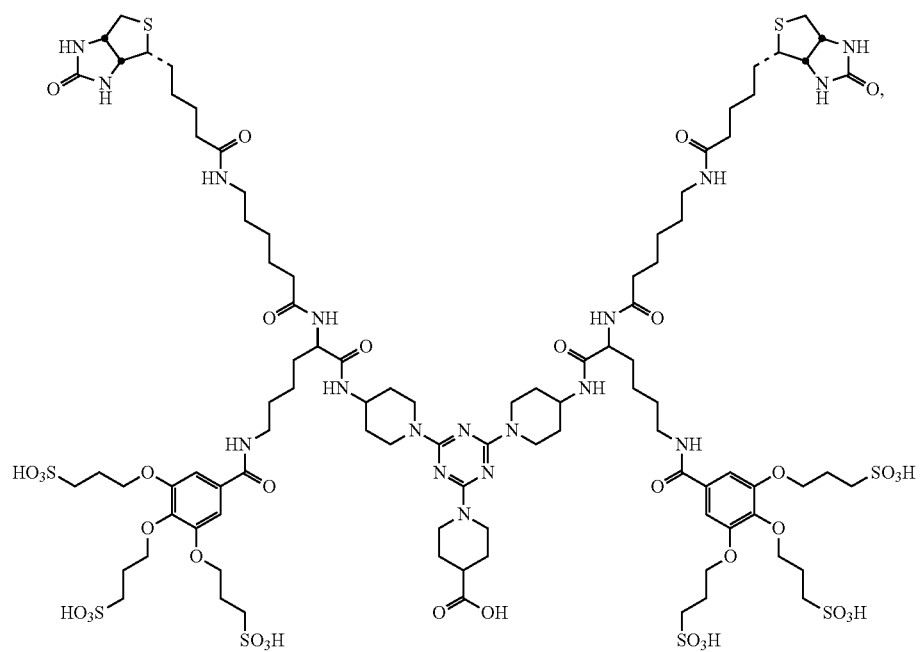

-continued
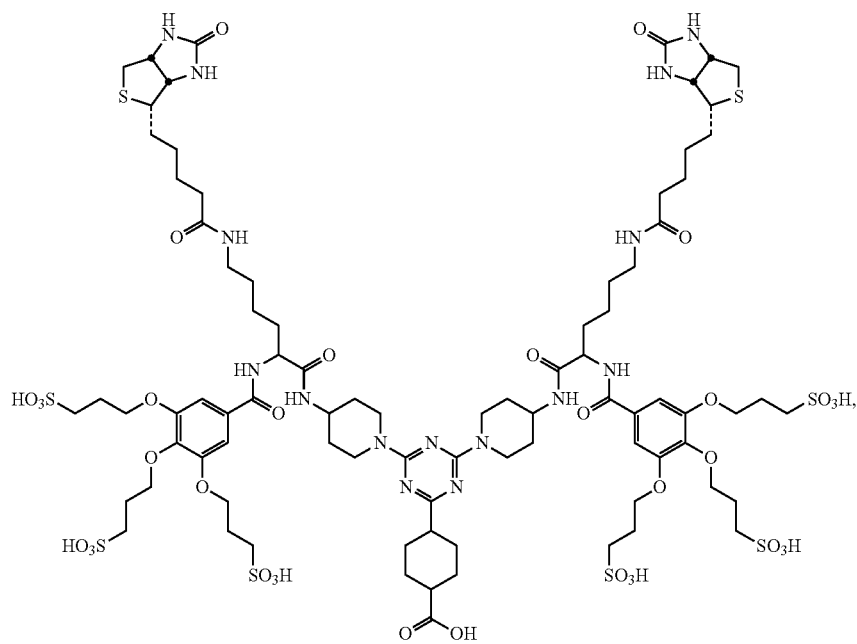
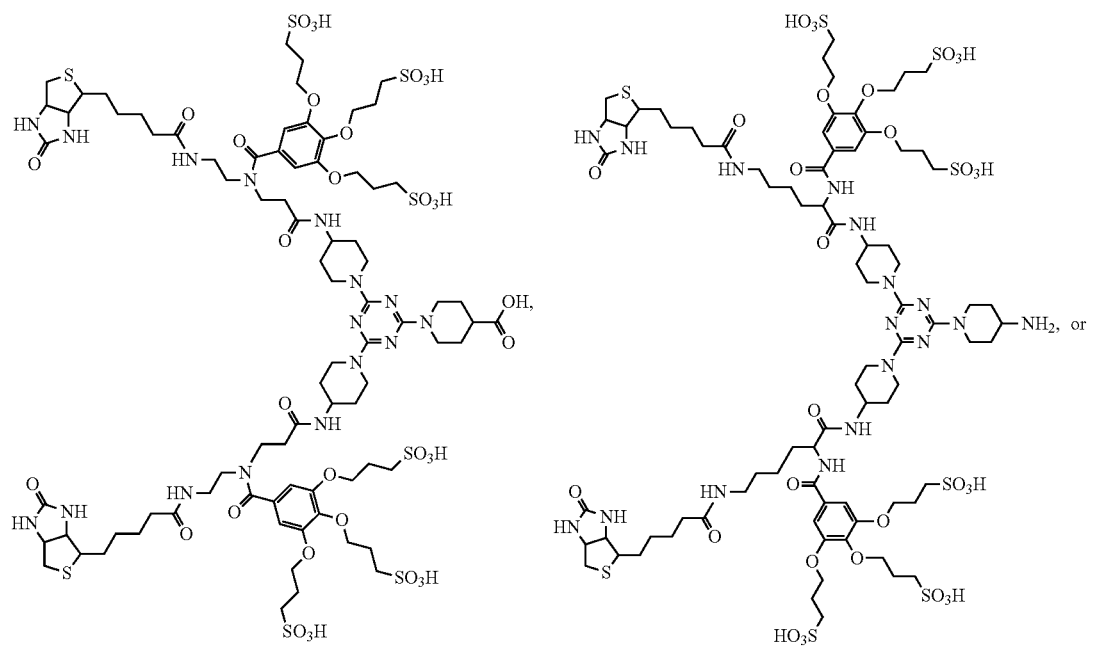

-continued
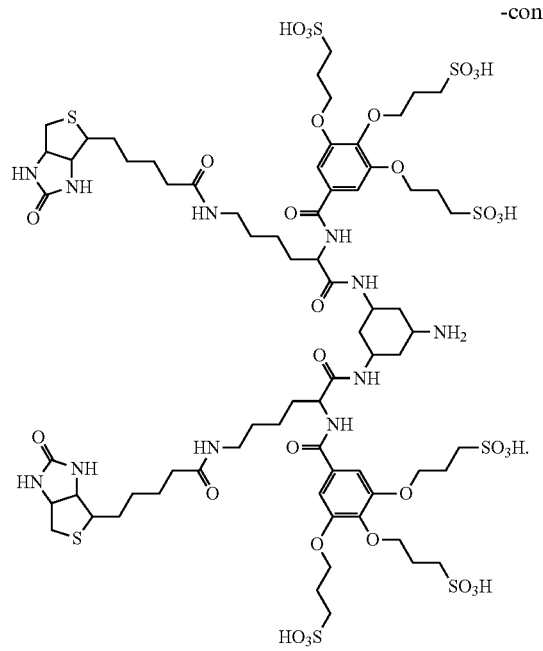
* * * * *